(12) United States Patent
Jinde et al.

(10) Patent No.: US 9,174,938 B2
(45) Date of Patent: Nov. 3, 2015

(54) ORGANIC ELECTROLUMINESCENCE DEVICE

(75) Inventors: Yukitoshi Jinde, Sodegaura (JP);
Hiroyuki Saito, Sodegaura (JP);
Kenichi Fukuoka, Sodegaura (JP);
Hiroshi Yamamoto, Sodegaura (JP);
Yuichiro Kawamura, Sodegaura (JP);
Masahiro Kawamura, Sodegaura (JP);
Takashi Arakane, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 885 days.

(21) Appl. No.: 12/735,175

(22) PCT Filed: Dec. 19, 2008

(86) PCT No.: PCT/JP2008/073180
§ 371 (c)(1),
(2), (4) Date: Jul. 30, 2010

(87) PCT Pub. No.: WO2009/081857
PCT Pub. Date: Jul. 2, 2009

(65) Prior Publication Data
US 2010/0301312 A1 Dec. 2, 2010

(30) Foreign Application Priority Data

Dec. 21, 2007 (JP) ................. 2007-331082
Dec. 22, 2007 (JP) ................. 2007-331224

(51) Int. Cl.
*H01L 51/50* (2006.01)
*C07D 209/86* (2006.01)
*B82Y 10/00* (2011.01)
*C09B 57/00* (2006.01)
*H01L 51/00* (2006.01)

(52) U.S. Cl.
CPC ............. *C07D 209/86* (2013.01); *B82Y 10/00* (2013.01); *C09B 57/008* (2013.01); *H01L 51/0059* (2013.01); *H01L 51/0072* (2013.01); *H01L 51/004* (2013.01); *H01L 51/0046* (2013.01); *H01L 51/0051* (2013.01); *H01L 51/0052* (2013.01); *H01L 51/0054* (2013.01); *H01L 51/0058* (2013.01); *H01L 51/0078* (2013.01); *H01L 51/5048* (2013.01); *H01L 51/5088* (2013.01)

(58) Field of Classification Search
USPC ............... 428/690, 917; 313/504, 505, 506;
257/40, E51.05, E51.026, E51.032;
564/26, 426, 430, 432, 434; 544/234
See application file for complete search history.

(56) References Cited

U.S. PATENT DOCUMENTS

| | | | |
|---|---|---|---|
| 5,061,569 A | 10/1991 | VanSlyke et al. | |
| 6,242,115 B1 | 6/2001 | Thomson et al. | |
| 2005/0227109 A1 | 10/2005 | Cheng et al. | |
| 2005/0227406 A1* | 10/2005 | Shtein et al. | 438/99 |
| 2005/0255334 A1* | 11/2005 | Kang et al. | 428/690 |
| 2006/0134460 A1* | 6/2006 | Kondakova et al. | 428/690 |
| 2006/0154105 A1* | 7/2006 | Yamamoto et al. | 428/690 |
| 2007/0257600 A1* | 11/2007 | Matsuura et al. | 313/498 |

FOREIGN PATENT DOCUMENTS

| | | |
|---|---|---|
| JP | 06-314594 A | 11/1994 |
| JP | 08-291115 A | 11/1996 |
| JP | 11-144873 A | 5/1999 |
| JP | 11-329737 A | 11/1999 |
| JP | 2000-302756 A | 10/2000 |
| JP | 2000-309566 A | 11/2000 |
| JP | 2001-273978 A | 10/2001 |
| JP | 2002-075648 | 3/2002 |
| JP | 2003-267972 A | 9/2003 |
| JP | 2005-044802 | 2/2005 |
| JP | 2006-056841 A | 3/2006 |
| JP | 2007-027092 A | 2/2007 |
| WO | WO 2004/080975 A1 | 9/2004 |
| WO | WO 2007/039952 A1 | 4/2007 |
| WO | WO 2007/125714 A1 | 11/2007 |
| WO | WO 2007/148660 A1 | 12/2007 |

1: Organic EL device
70: Cathode
60: Electron-injecting layer
50: Electron-transporting layer
40: Emitting layer
30: Hole-transporting layer
20: Hole-injecting layer
10: Anode

OTHER PUBLICATIONS

Tang et al., "Organic Electroluminescent Diodes", Applied Physics Letters, 1987, vol. 51(12), pp. 913-915.
International Search Report received in Mar. 24, 2009 for International Application No. PCT/JP2008/073180 with International Preliminary Report on Patentability (11 pgs).
Observations by third party Japanese Patent Application No. 2009 547075 dated Nov. 24, 2012.

* cited by examiner

*Primary Examiner* — Gregory Clark
(74) *Attorney, Agent, or Firm* — Foley & Lardner LLP

(57) ABSTRACT

An organic electroluminescence device including: an anode (10), a cathode (70), an emitting layer (40) including an organic compound, which is between the anode (10) and the cathode (70), two or more layers arranged in a hole injection and transport region which is between the anode (10) and the emitting layer (40), and one or more layers arranged in an electron injection and transport region which is between the emitting layer (40) and the cathode (70), wherein a layer in the hole injection and transport region, which is in contact with the emitting layer (40), includes an aromatic amine derivative having a carbazole skeleton, one of the layers other than the layer in contact with the emitting layer (40) in the hole injection and transport region includes one or more materials selected from the group consisting of thiophene derivatives, tricyclic or more cyclic fused aromatic derivatives, amine derivatives excluding the compound represented by the following formula (A), conductive polymers, $CF_x$, CuPc, transition metal oxides, fullerenes and acceptor materials, and a layer in the electron injection and transport region includes a benzimidazole derivative.

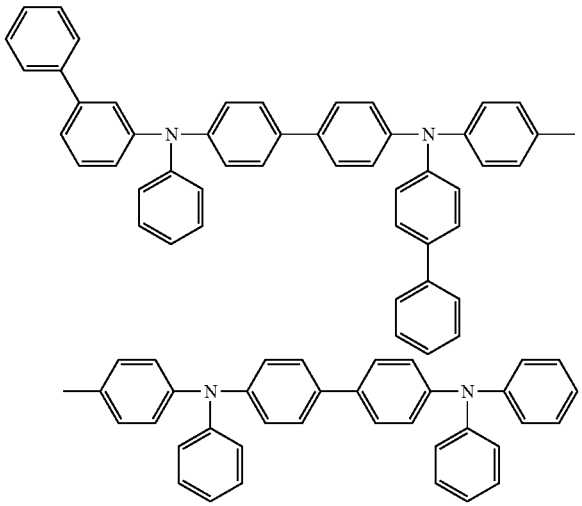

(A)

10 Claims, 1 Drawing Sheet

ORGANIC ELECTROLUMINESCENCE DEVICE

TECHNICAL FIELD

The invention relates to an organic electroluminescence device, particularly to an organic electroluminescence device having longer emission life time and high luminous efficiency. Also, the invention relates to a white light-emitting organic electroluminescence device, particularly to a white light-emitting organic electroluminescence device having longer emission life time and high luminous efficiency.

BACKGROUND ART

An organic electroluminescence device (hereinafter the term "electroluminescence" is often abbreviated as "EL") is a self-emission device utilizing the principle that a fluorescent compound emits light by the recombination energy of holes injected from an anode and electrons injected from a cathode when an electric field is impressed.

Since C. W. Tang et al. of Eastman Kodak Co. reported a low-voltage driven organic EL device in the form of a stacked type device (Non-patent Document 1, or the like), studies on organic EL devices wherein organic materials are used as the constituent materials has actively been conducted.

Tang et al. use tris(8-hydroxyquinolinol aluminum) for the emitting layer and a triphenyldiamine derivative for the hole-transporting layer. The advantages of the stack structure are to increase injection efficiency of holes to the emitting layer, to increase generation efficiency of excitons generated by recombination by blocking electrons injected in the cathode, to confine the generated excitons in the emitting layer, and so on.

Like this example, as the structure of the organic EL device, a two-layered type of a hole-transporting (injecting) layer and an electron-transporting emitting layer, and a three-layered type of a hole-transporting (injecting) layer, an emitting layer and an electron-transporting (injecting) layer are widely known. In such stack structure devices, their device structures and fabrication methods have been contrived to increase recombination efficiency of injected holes and electrons.

Heretofore, as a hole-injecting material used for an organic EL device, materials having a phenylenediamine structure disclosed in Patent Documents 1 and 2 have been known and widely used. Also, arylamine-based materials containing a benzidine skeleton disclosed in Patent Documents 3 and 4 have been used for a hole-transporting material.

On the other hand, Patent Documents 5 to 7 disclose arylamine-based compounds having a carbazole. These materials have the feature that when using these materials as the hole-transporting material, luminous efficiency is improved. However, there are drawbacks that driving voltage becomes significantly high at the same time, and that lifetime of the device becomes extremely short.

Patent Document 8 discloses a device using two or more hole-injecting layers in which the ionization potential values are stepwise set, in order to efficiently inject holes from an anode to an emitting layer. However, use of the material system disclosed in Patent Document 8 was insufficient in both the luminous efficiency and the life time.

[Patent Document 1] JP-A-H08-291115
[Patent Document 2] JP-A-2000-309566
[Patent Document 3] U.S. Pat. No. 5,061,569
[Patent Document 4] JP-A-2001-273978
[Patent Document 5] U.S. Pat. No. 6,242,115
[Patent Document 6] JP-A-2000-302756
[Patent Document 7] JP-A-H11-144873
[Patent Document 8] JP-A-H06-314594
[Non-patent Document 1] C. W. Tang, S. A. Vanslyke, Applied Physics, Letters, 51, 913 (1987)

An object of the invention is to provide an organic EL device having high efficiency and long life time.

An object of the invention is to provide a white light-emitting organic EL device having high efficiency and long life time.

DISCLOSURE OF THE INVENTION

According to the invention, the following organic EL device is provided.

1. An organic electroluminescence device comprising:
    an anode,
    a cathode,
    an emitting layer comprising an organic compound, which is between the anode and the cathode,
    two or more layers arranged in a hole injection and transport region which is between the anode and the emitting layer, and
    one or more layers arranged in an electron injection and transport region which is between the emitting layer and the cathode,
    wherein a layer in the hole injection and transport region, which is in contact with the emitting layer, comprises an aromatic amine derivative having a carbazole skeleton,
    one of the layers other than the layer in contact with the emitting layer in the hole injection and transport region comprises one or more materials selected from the group consisting of thiophene derivatives, tricyclic or more cyclic fused aromatic derivatives, amine derivatives excluding the compound represented by the following formula (A), conductive polymers, $CF_x$, CuPc, transition metal oxides, fullerenes and acceptor materials, and
    a layer in the electron injection and transport region comprises a benzimidazole derivative.

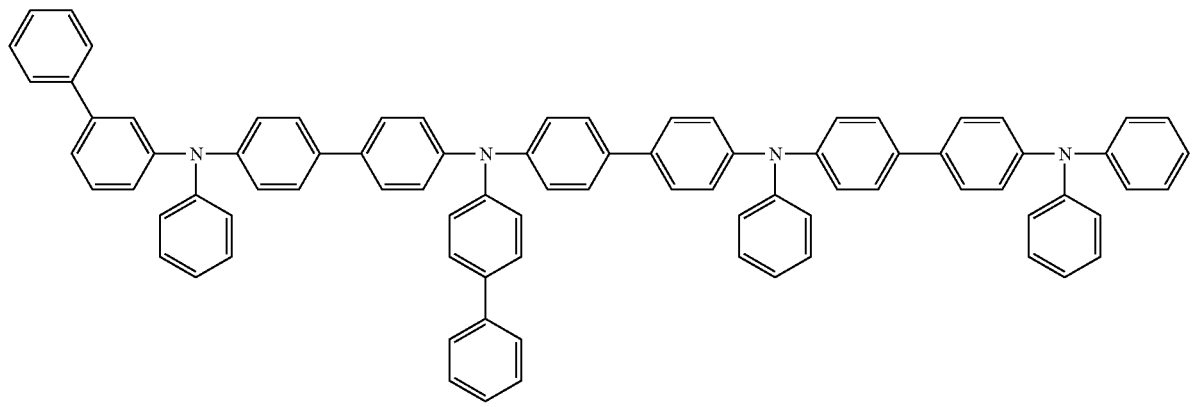

(A)

2. The organic electroluminescence derivative according to 1, wherein the aromatic amine derivative having a carbazole skeleton is a compound represented by the following formula (1):

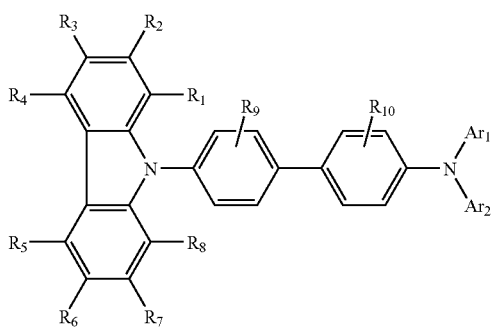

(1)

wherein $Ar_1$ and $Ar_2$ are independently an aromatic hydrocarbon ring group or an aromatic heterocyclic group which may be substituted, $R_1$ to $R_{10}$ are independently a hydrogen atom, a halogen atom, an alkyl group, an aralkyl group, an alkenyl group, a cyano group, an amino group, an acyl group, an alkoxycarbonyl group, a carboxy group, an alkoxy group, an aryloxy group, an alkylsulfonyl group, a hydroxy group, an amido group, an aromatic hydrocarbon ring group or an aromatic heterocyclic group which may be substituted, and adjacent groups of $R_1$ to $R_{10}$ may form a ring.

3. The organic electroluminescence derivative according to 1, wherein the aromatic amine derivative having a carbazole skeleton is a compound represented by the following formula (2):

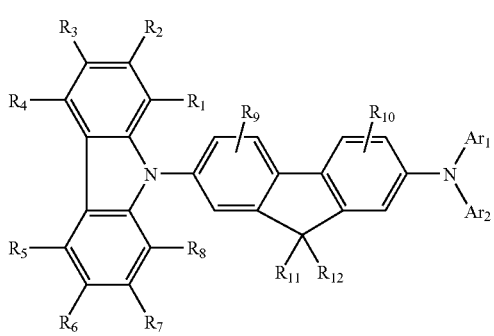

(2)

wherein $Ar_1$ and $Ar_2$ are independently an aromatic hydrocarbon ring group or an aromatic heterocyclic group which may be substituted, $R_1$ to $R_{12}$ are independently a hydrogen atom, a halogen atom, an alkyl group, an aralkyl group, an alkenyl group, a cyano group, an amino group, an acyl group, an alkoxycarbonyl group, a carboxyl group, an alkoxy group, an aryloxy group, alkylsulfonyl group, a hydroxy group, an amido group, an aromatic hydrocarbon ring group or an aromatic heterocyclic group which may be substituted, and adjacent groups of $R_1$ to $R_{12}$ may from a ring.

4. The organic electroluminescence device according to any one of 1 to 3, wherein the carbazole skeleton of the aromatic amine derivative is a monocarbazolyl group.

5. The organic electroluminescence derivative according to any one of 1 to 4, wherein the benzimidazole derivative is a compound represented by the following formula (3) or (4):

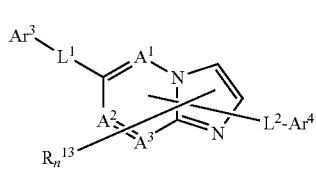

(3)

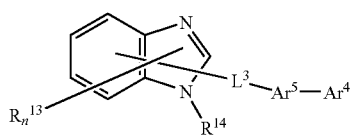

(4)

wherein $A^1$ to $A^3$ are independently a nitrogen atom or a carbon atom, $Ar^3$ is a substituted or unsubstituted aryl group having 6 to 60 carbon atoms that form a ring (hereinafter referred to as "ring carbon atoms") or a substituted or unsubstituted heteroaryl group having 3 to 60 atoms that form a ring (hereinafter referred to as "ring atoms"), and $Ar^4$ is a hydrogen atom, a substituted or unsubstituted aryl group having 6 to 60 ring carbon atoms, a substituted or unsubstituted heteroaryl group having 3 to 60 ring carbon atoms, a substituted or unsubstituted alkyl group having 1 to 20 carbon atoms, or a substituted or unsubstituted alkoxy group having 1 to 20 carbon atoms, provided that $Ar^3$ or $Ar^4$ is a substituted or unsubstituted fused ring group having 10 to 60 ring carbon atoms, or a substituted or unsubstituted monohetero fused ring group, Ar$^5$ is a substituted or unsubstituted arylene group having 6 to 60 carbon atoms, or a substituted or unsubstituted heteroarylene group having 3 to 60 carbon atoms, L$^1$, L$^2$ and L$^3$ are independently a single bond, a substituted or unsubstituted arylene group having 6 to 60 ring carbon atoms, a substituted or unsubstituted heteroarylene group having 3 to 60 ring carbon atoms, or a substituted or unsubstituted fluorenylene group, R$^{13}$ is a hydrogen atom, a substituted or unsubstituted aryl group having 6 to 60 ring carbon atoms, a substituted or unsubstituted heteroaryl group having 3 to 60 ring carbon atoms, a substituted or unsubstituted alkyl group having 1 to 20 carbon atoms, or a substituted or unsubstituted alkoxy group having 1 to 20 carbon atoms, n is an integer of 0 to 5, when n is 2 or more, plural R$^{13}$s may be the same or different, and adjacent R$^{13}$s may bond to each other to form a carbocyclic aliphatic ring or a carbocyclic aromatic ring, and R$^{14}$ is a hydrogen atom, a substituted or unsubstituted aryl group having 6 to 60 ring carbon atoms, a substituted or unsubstituted heteroaryl group having 3 to 60 ring carbon atoms, a substituted or unsubstituted alkyl group having 1 to 20 carbon atoms, a substituted or unsubstituted alkoxy group having 1 to 20 carbon atoms, or -L$^1$-Ar$^5$—Ar$^4$.

6. The organic electroluminescence device according to any one of 1 to 5, wherein the thiophene derivative is a compound represented by the following formula (x):

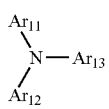

wherein at least one of Ar$_{11}$ to Ar$_{13}$ is a substituent represented by the following formula (y), Ar$_{11}$ to Ar$_{13}$ which are not the substituent represented by the formula (y) are a substituted or unsubstituted aryl group having 6 to 50 ring carbon atoms or a substituent represented by the following formula (z), and Ar$_{11}$ to Ar$_{13}$ are the same or different:

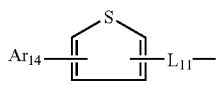

wherein Ar$_{14}$ is an aryl group having 6 to 50 ring carbon atoms, and

L$_{11}$ is a substituted or unsubstituted arylene group having 6 to 50 ring carbon atoms or a substituted or unsubstituted heteroarylene group having 6 to 50 ring atoms, and

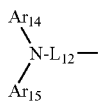

wherein L$_{12}$ is a substituted or unsubstituted arylene group having 6 to 50 ring carbon atoms, and Ar$_{14}$ and Ar$_{15}$ are independently a substituted or unsubstituted aryl group having 6 to 50 ring carbon atoms, a substituent represented by the formula (y) or a substituent represented by the formula (z).

7. The organic electroluminescence device according to any one of 1 to 6, which emits blue light.

8. A display comprising the organic electroluminescence device according to any one of 1 to 7.

9. A white light-emitting organic electroluminescence device comprising:

an anode, a cathode, an emitting layer comprising an organic compound which is between the anode and the cathode, one or more layers arranged in a hole injection and transport region which is between the anode and the emitting layer, and one or more layers arranged in an electron injection and transport region which is between the emitting layer and the cathode, wherein a layer in the hole injection and transport region, which is in contact with the emitting layer, comprises an aromatic amine derivative having a carbazole skeleton, and a layer in the electron injection and transport region comprises a benzimidazole derivative.

10. The white light-emitting organic electroluminescence device according to 9, wherein the aromatic amine derivative having a carbazole skeleton is a compound represented by the following formula (1):

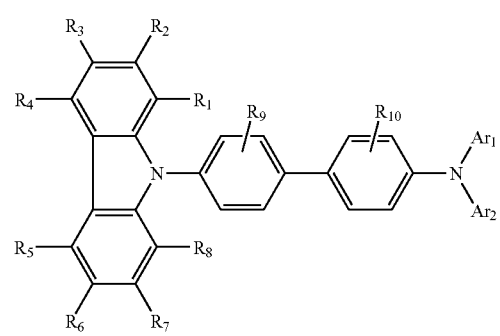

wherein Ar$_1$ and Ar$_2$ are independently an aromatic hydrocarbon ring group or an aromatic heterocyclic group which may be substituted, and R$_1$ to R$_{10}$ are independently a hydrogen atom, a halogen atom, an alkyl group, an aralkyl group, alkenyl group, a cyano group, an amino group, an acyl group, an alkoxycarbonyl group, a carboxy group, an alkoxy group, an aryloxy group, an alkylsulfonyl group, a hydroxy group, an amido group, an aromatic hydrocarbon ring group or an aromatic heterocyclic group which may be substituted, and adjacent groups of R$_1$ to R$_{10}$ may form a ring.

11. The white light-emitting organic electroluminescence device according to 9, wherein the aromatic amine derivative having a carbazole skeleton is a compound represented by the following formula (2):

(2)

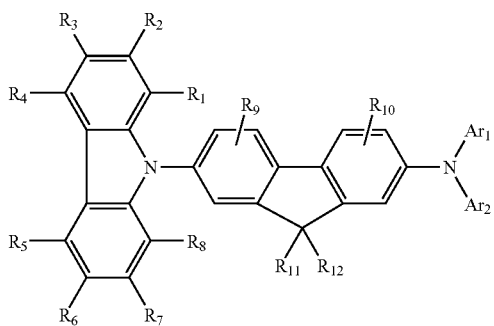

wherein $Ar_1$ and $Ar_2$ are independently an aromatic hydrocarbon ring group or an aromatic heterocyclic group which may be substituted, and $R_1$ to $R_{12}$ are independently a hydrogen atom, a halogen atom, an alkyl group, an aralkyl group, an alkenyl group, a cyano group, an amino group, an acyl group, an alkoxycarbonyl group, a carboxy group, an alkoxy group, an aryloxy group, an alkylsulfonyl group, a hydroxy group, an amido group, an aromatic hydrocarbon ring group or an aromatic heterocyclic group which may be substituted, and adjacent groups of $R_1$ to $R_{12}$ may form a ring.

12. The white light-emitting organic electroluminescence device according to any one of 9 to 11, wherein the carbazole skeleton of the aromatic amine derivative is a monocarbazolyl group.

13. The white light-emitting organic electroluminescence device according to any one of 9 to 12, wherein the benzimidazole derivative is a compound represented by the following formula (3) or (4):

(3)
(4)

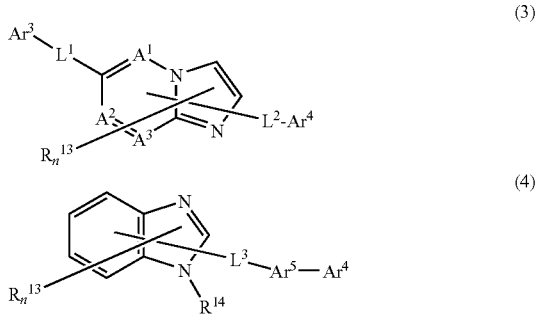

wherein $A^1$ to $A^3$ are independently a nitrogen atom or a carbon atom, $Ar^3$ is a substituted or unsubstituted aryl group having 6 to 60 ring carbon atoms or a substituted or unsubstituted heteroaryl group having 3 to 60 ring atoms, $Ar^4$ is a hydrogen atom, a substituted or unsubstituted aryl group having 6 to 60 ring carbon atoms, a substituted or unsubstituted heteroaryl group having 3 to 60 ring atoms, a substituted or unsubstituted alkyl group having 1 to 20 carbon atoms or a substituted or unsubstituted alkoxy group having 1 to 20 carbon atoms, provided that $Ar^3$ or $Ar^4$ is a substituted or unsubstituted fused ring group having 10 to 60 ring carbon atoms or a substituted or unsubstituted monohetero fused ring group having 3 to 60 ring carbon atoms, $Ar^5$ is a substituted or unsubstituted arylene group having 6 to 60 carbon atoms or a substituted or unsubstituted heteroarylene group having 3 to 60 carbon atoms, $L^1$, $L^2$ and $L^3$ are independently a single bond, a substituted or unsubstituted arylene group having 6 to 60 ring carbon atoms, a substituted or unsubstituted heteroarylene group having 3 to 60 ring carbon atoms, or a substituted or unsubstituted fluorenylene group, $R^{13}$ is a hydrogen atom, a substituted or unsubstituted aryl group having 6 to 60 ring carbon atoms, a substituted or unsubstituted heteroaryl group having 3 to 60 ring carbon atoms, a substituted or unsubstituted alkyl group having 1 to 20 carbon atoms or a substituted or unsubstituted alkoxy group having 1 to 20 carbon atoms, n is an integer of 0 to 5, when n is 2 or more, plural $R^{13}$s may be the same or different, and adjacent $R^{13}$s may bond to form a carbocyclic aliphatic ring or a carbocyclic aromatic ring, and $R^{14}$ is a hydrogen atom, a substituted or unsubstituted aryl group having 6 to 60 ring carbon atoms, a substituted or unsubstituted heteroaryl group having 3 to 60 ring carbon atoms, a substituted or unsubstituted alkyl group having 1 to 20 carbon atoms, a substituted or unsubstituted alkoxy group having 1 to 20 carbon atoms, or $-L^1-Ar^5-Ar^4$.

14. A display comprising the white light-emitting organic electroluminescence device according to any one of 9 to 13.

According to the invention, an organic EL device having high efficiency and long life time can be provided by using a material having a specific structure.

According to the invention, a white light-emitting organic EL device having high efficiency and long life time can be provided by using a material having a specific structure.

BEST MODE FOR CARRYING OUT THE INVENTION

Now, detail explanation will be given to the organic EL device according to the first embodiment of the invention.

The organic EL device according to the first embodiment of the invention has at least an emitting layer formed of an organic compound between an anode and a cathode. It has two or more layers in a hole injection and transport region located between the anode and the emitting layer, and one or more layer in an electron injection and transport region located between the cathode and the emitting layer.

Figure 1:
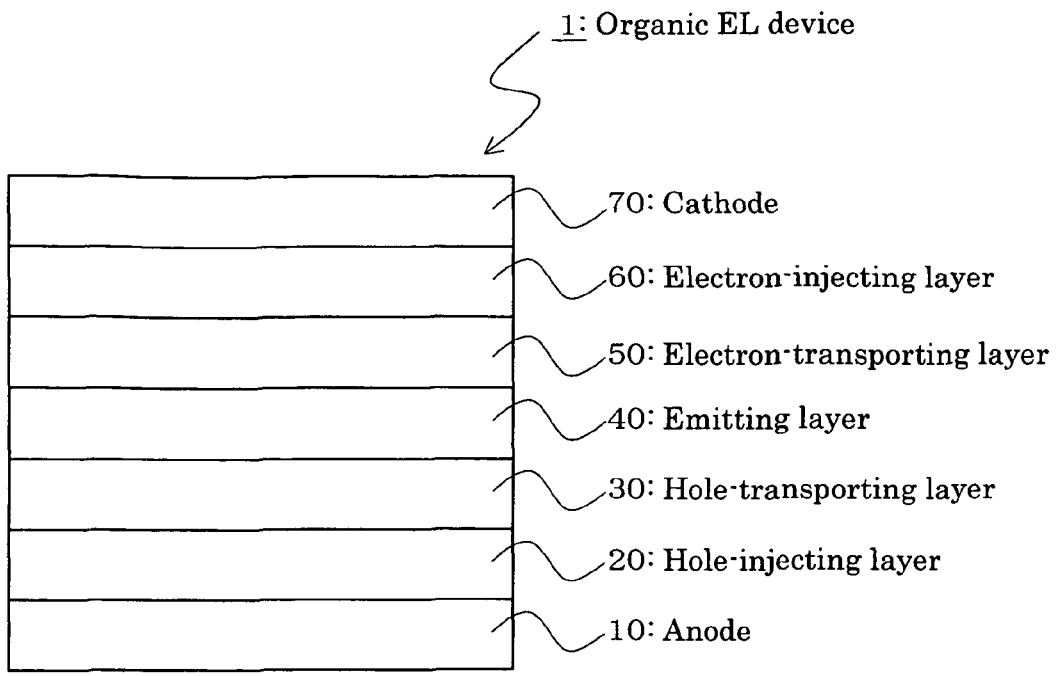
FIG. 1 is a schematic cross-sectional view of an organic EL device according to the first embodiment of the invention.

FIG. 1 is a schematic cross-sectional view of an organic EL device according to the first embodiment of the invention.

In an organic EL device 1, an anode 10, a hole-injecting layer 20, a hole-transporting layer 30, an emitting layer 40, an electron-transporting layer 50, an electron-injecting layer 60 and a cathode 70 are stacked sequentially on a substrate (not shown).

In the first embodiment of the invention, a hole-injecting layer 20 which is one of the layers arranged in the hole injection and transport region other than the layer in contact with the emitting layer; a hole-transporting layer 30 arranged in the hole injection and transport region and in contact with the emitting layer; and an electron-transporting layer 50 and an electron-injecting layer 60 arranged in the electron injection and transport region satisfy the following conditions (A), (B) and (C):

(A) one of the layers (hole-injecting layer 20) arranged in the hole-injection and transport region other than the layer in contact with the emitting layer contains one or more materials selected from the group consisting of thiophene derivatives, three or more ring-fused aromatic derivatives, amine derivatives (excluding the compound represented by the following formula (A)), conductive polymers, $CF_x$, CuPc, transition metal oxides, fullerenes and acceptor materials.

The thiophene derivatives contained in the hole-injecting layer 20 include thiophene-containing conductive high-molecular compounds such as PEDOT:PSS (Synthetic Metal, 111-112, P. 139 (2000)) and thiophene-containing low-molecular compounds (see JP-A-H10-219242, JP-A-2003-267972 and JP-A-2000-252070) such as aminothiophene (see JP-A-H04-304466) as the representative thiophene derivative. Further, diamine derivatives (U.S. Pat. No. 5,061,569, JP-A-H08-048656 and JP-B-3,529,735) which are also thiophene derivatives, and triamine derivatives (JP-B-3,565,870 and WO2006/114921) which are also thiophene derivatives may be mentioned.

The thiophene derivative contained in the hole-injecting layer 20 is preferably a compound represented by the following formula (x):

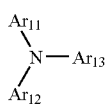
(x)

wherein
at least one of $Ar_{11}$ to $Ar_{13}$ is a substituent represented by the following formula (y), and $Ar_{11}$ to $Ar_{13}$ which are not the substituent represented by the formula (y) are a substituted or unsubstituted aryl group having 6 to 50 ring carbon atoms or a substituent represented by the following formula (z), and
$Ar_{11}$ to $Ar_{13}$ may be the same or different;

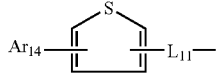
(y)

wherein
$Ar_{14}$ is an aryl group having 6 to 50 ring carbon atoms, and
$L_{11}$ is a substituted or unsubstituted arylene group having 6 to 50 ring carbon atoms or a substituted or unsubstituted heteroarylene group having 6 to 50 ring atoms;

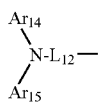
(z)

wherein
$L_{12}$ is a substituted or unsubstituted arylene group having 6 to 50 ring carbon atoms, and
$Ar_{14}$ and $Ar_{15}$ are independently a substituted or unsubstituted aryl group having 6 to 50 ring carbon atoms, the substituent represented by the formula (y) or the substituent represented by the formula (z).

Specific examples of the aryl group having 6 to 50 ring carbon atoms include a phenyl group, a biphenyl group, a phenanthryl group, a chrysenyl group, a benzphenanthryl group, a terphenyl group, a benzanthranyl group, a benzchrysenyl group, a biphenyl group, a naphthacenyl group, an anthranyl group, a pentacenyl group, a picenyl group and a pentaphenyl group. Preferred are a phenyl group, a biphenyl group, a naphthyl group and a terphenyl group.

Specific examples of the arylene group having 6 to 50 ring carbon atoms include a phenylene group, a naphthylene group, a biphenylene group, a terphenylene group, a phenanthrene group, a triphenylene group, an anthranylene group, a pentacenylene group, a perylenylene group, a pycenylene group, a pyrenylene group, a pentaphenylene group, a 9,9-dimethylfluonylene group, 9,9-diphenylfluonylene group and the following divalent groups:

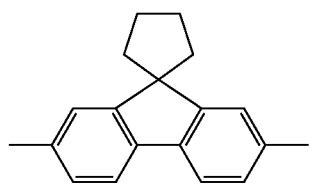

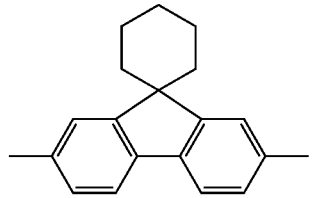

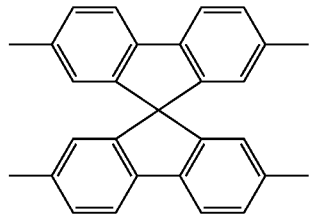

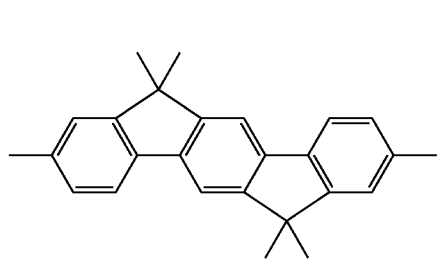

Of the specific examples of the arylene group having 6 to 50 ring carbon atoms, a phenylene group, a biphenylene group, a 9,9-dimethylfluonylene group and the above-mentioned divalent groups are preferable.

The compound represented by the formula (x) is preferably a monoamine compound or a diamine compound, more preferably an asymmetric monoamine compound or an asymmetric diamine compound.

Specific examples of the compound represented by the formula (x) include:
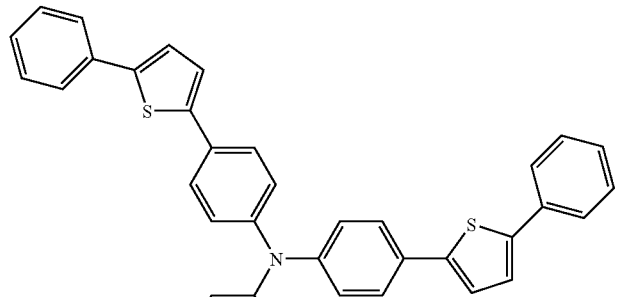
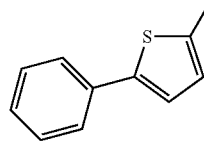
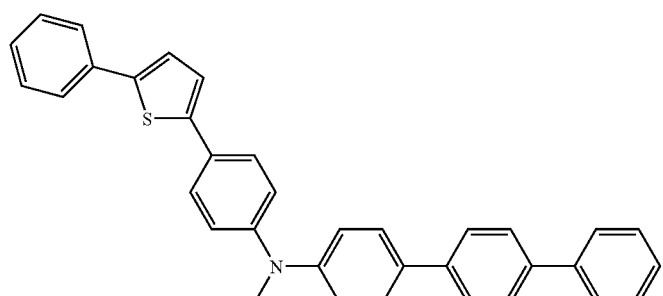
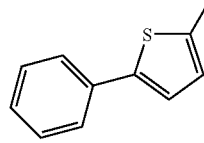
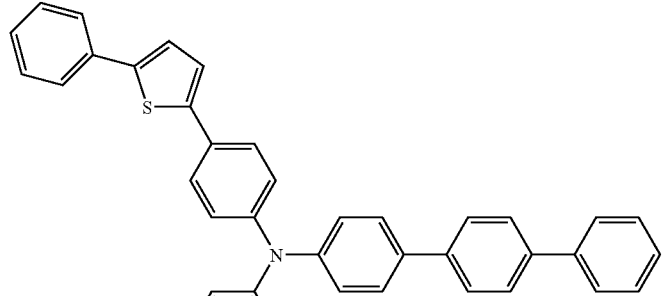
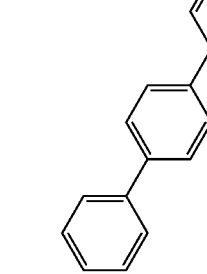

-continued
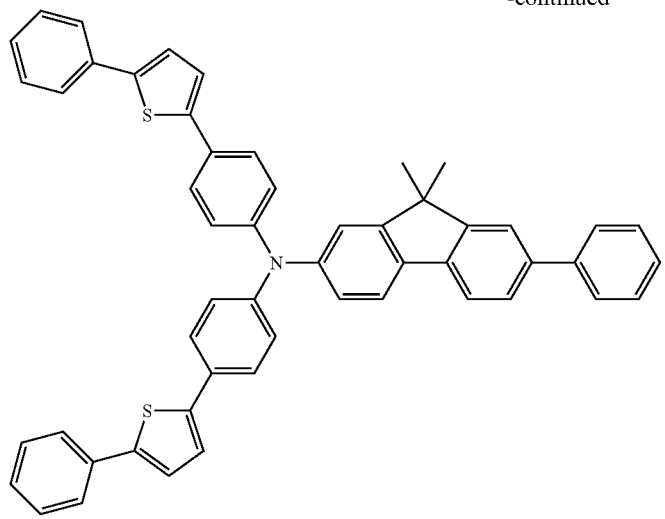
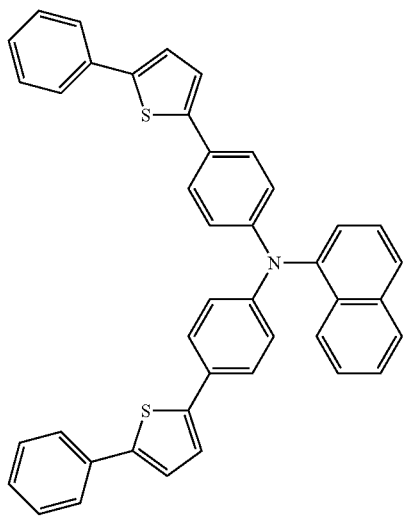
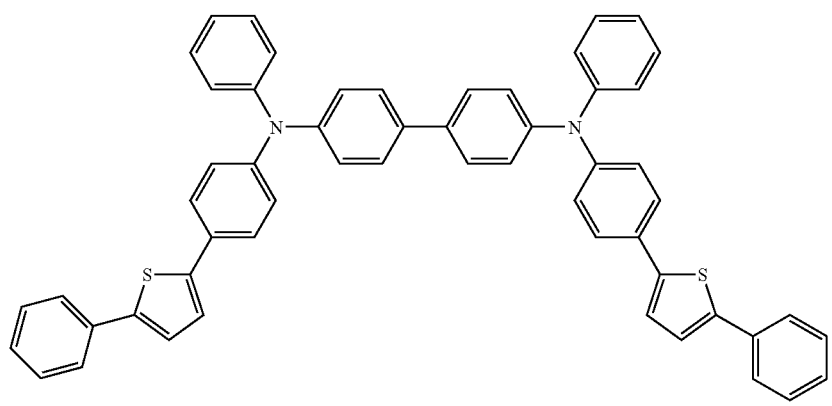
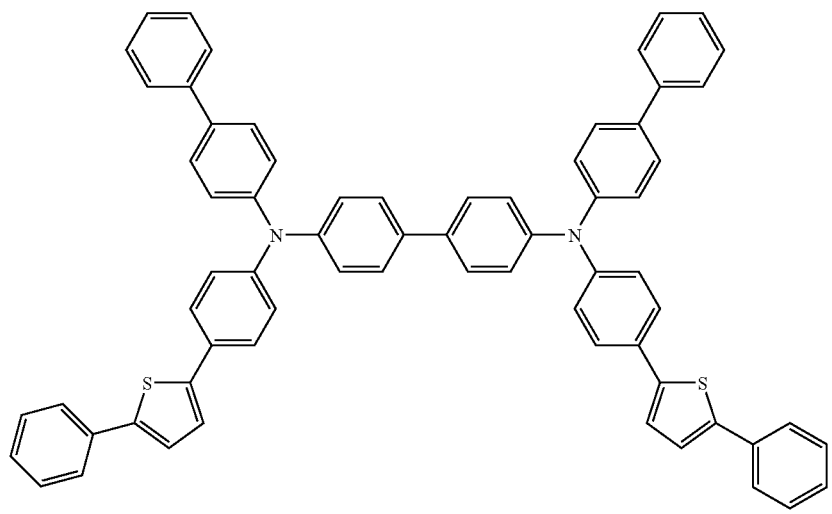

-continued
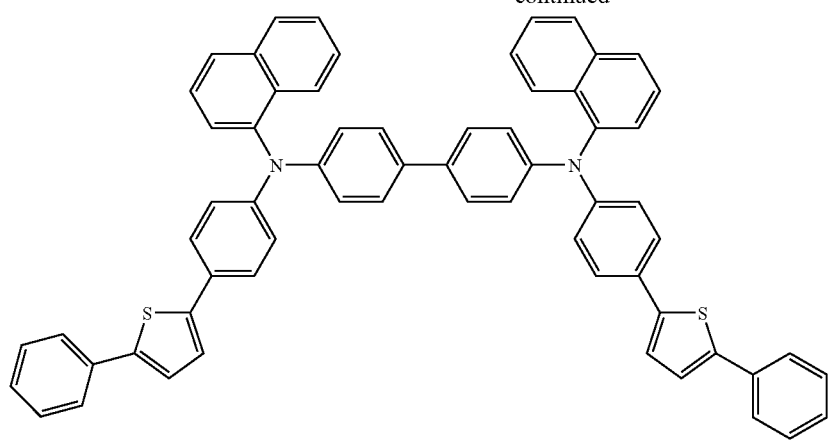
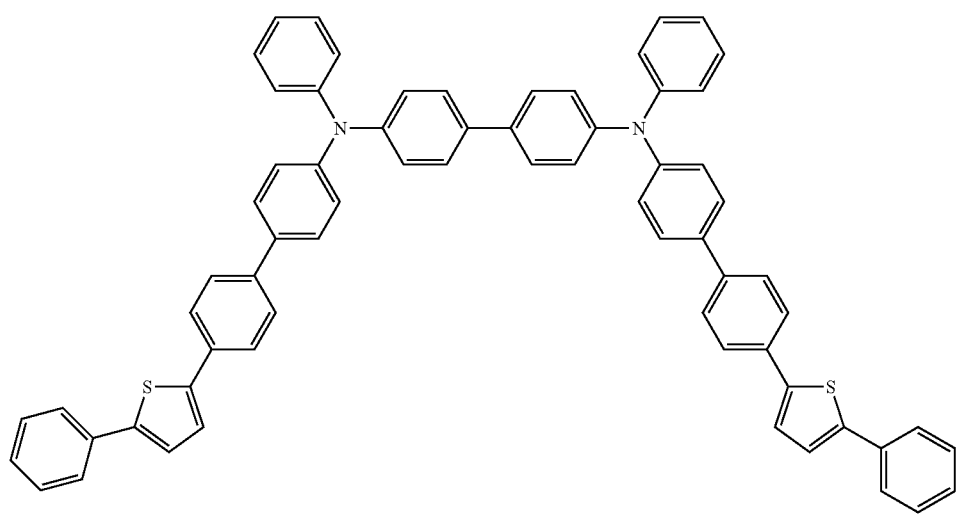
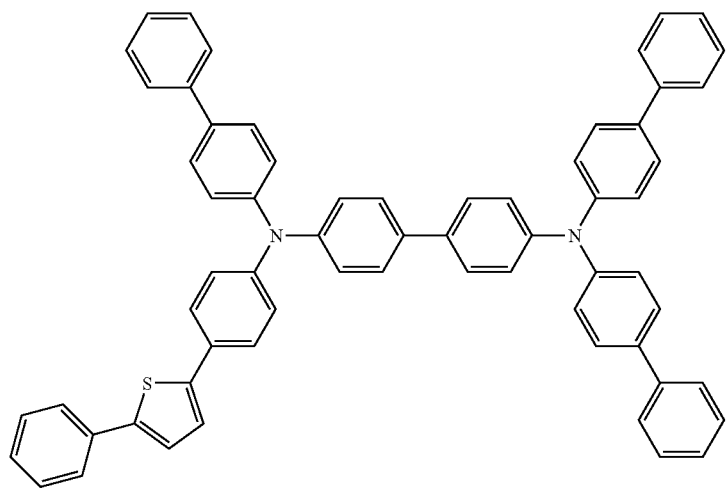

-continued
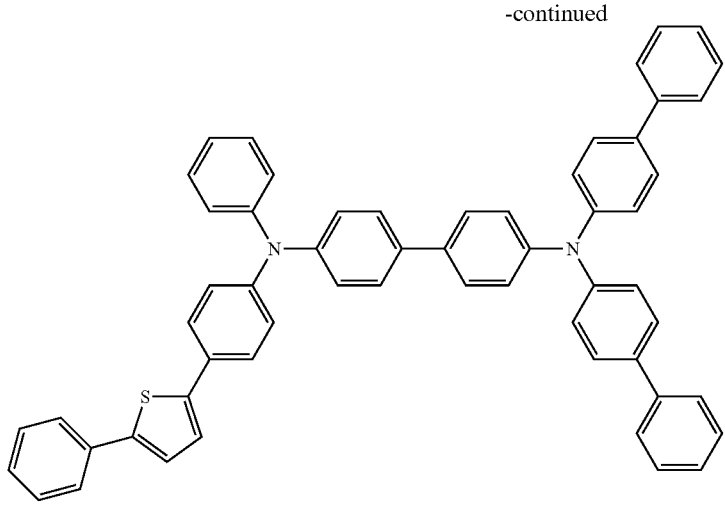
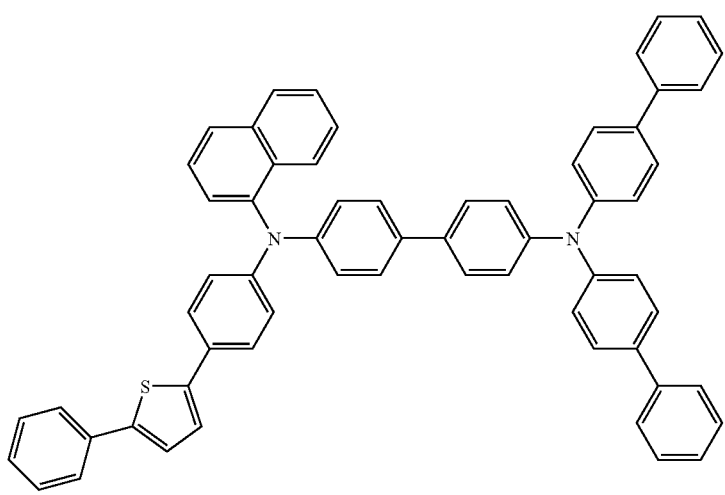
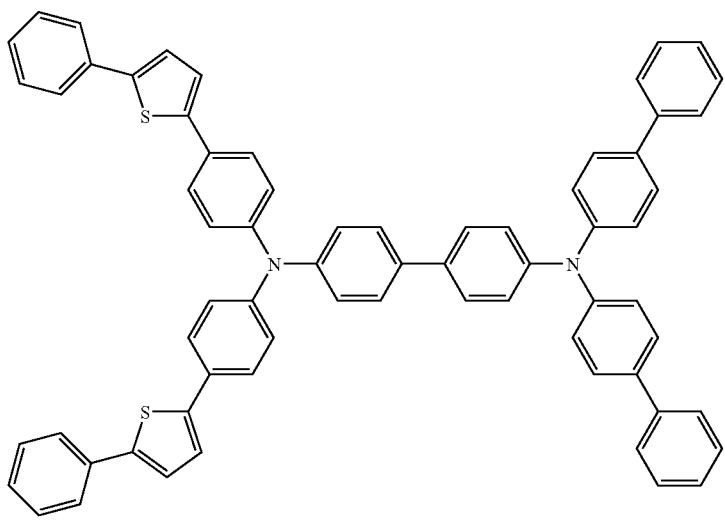

-continued
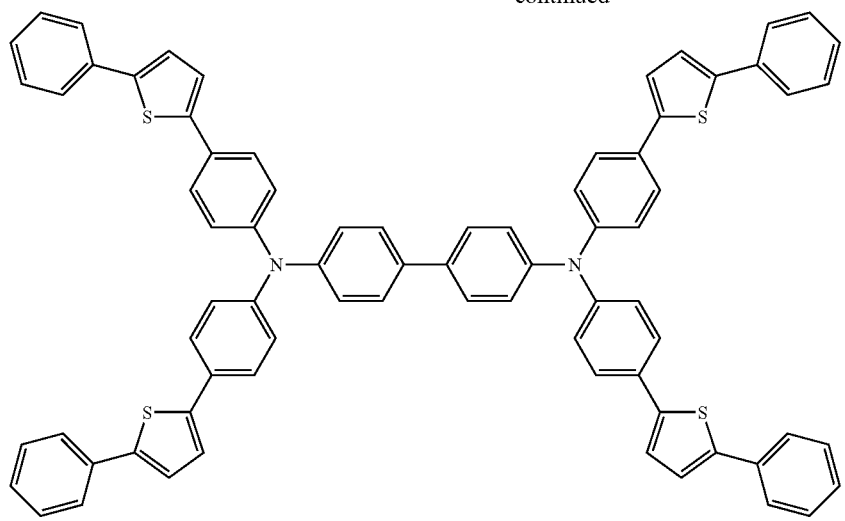
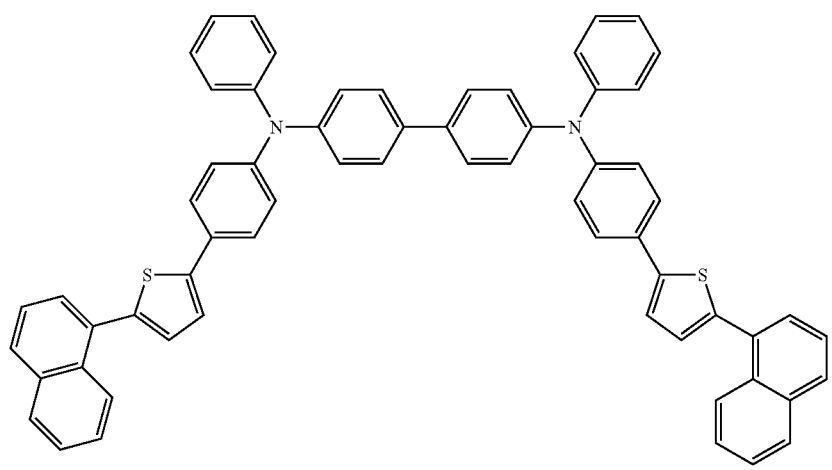
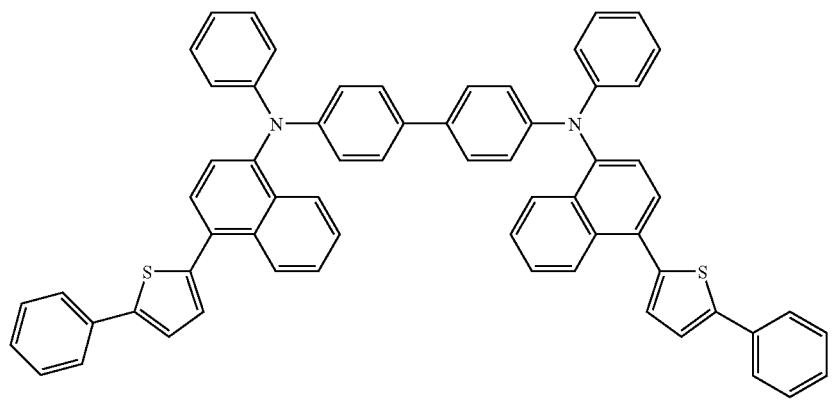

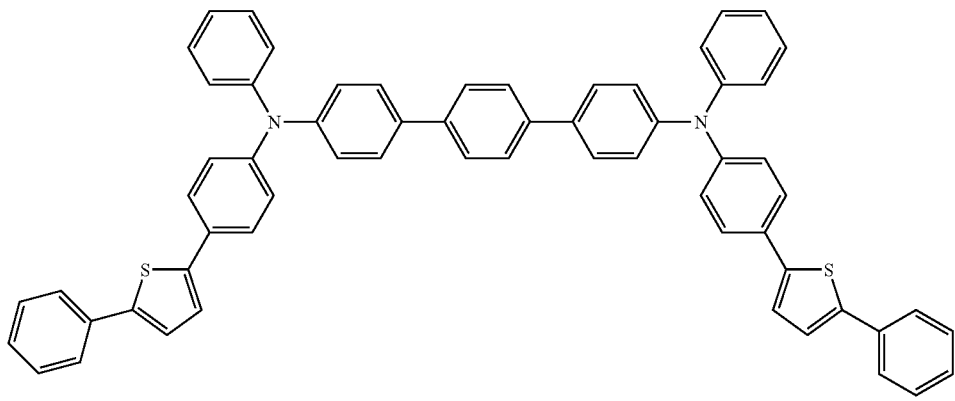
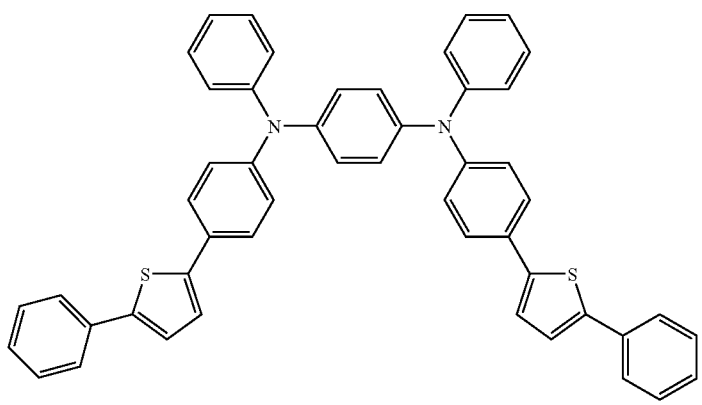
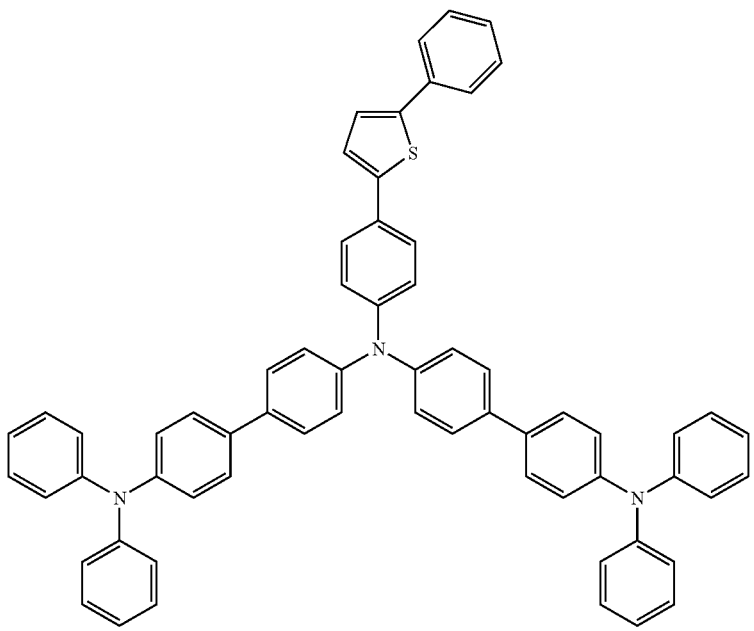

-continued
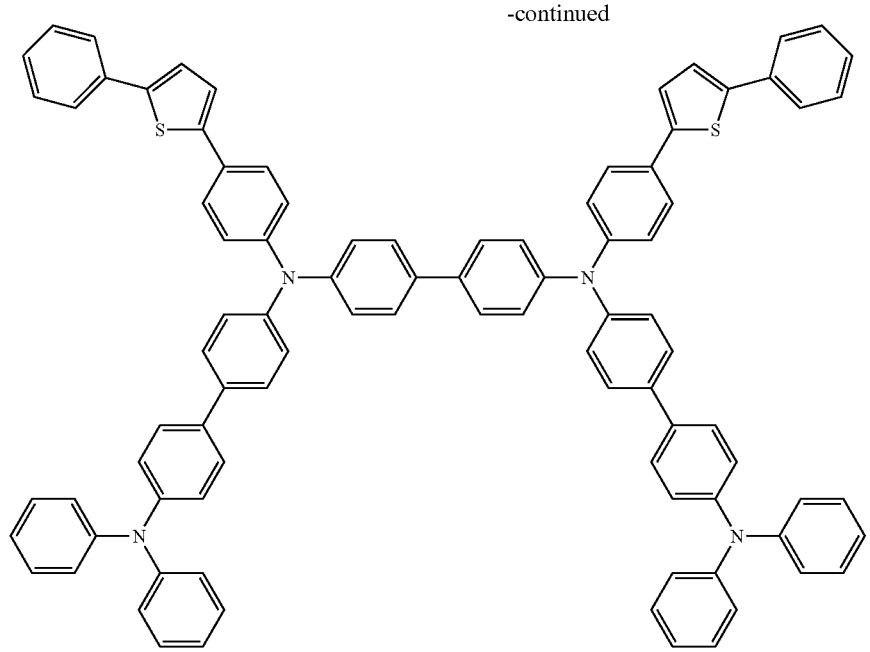
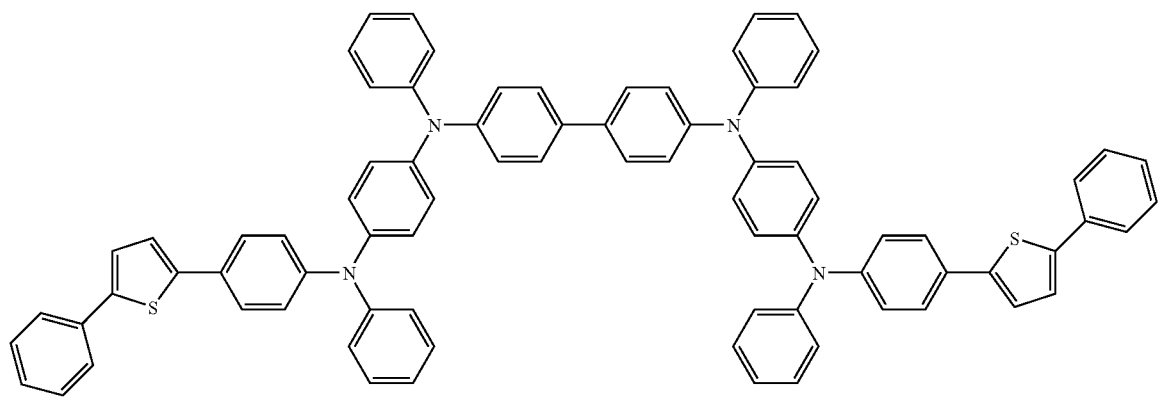
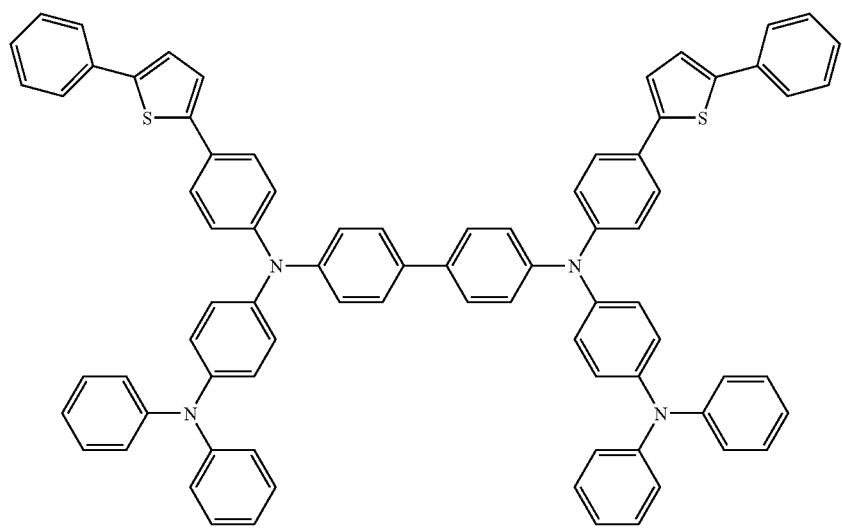

-continued
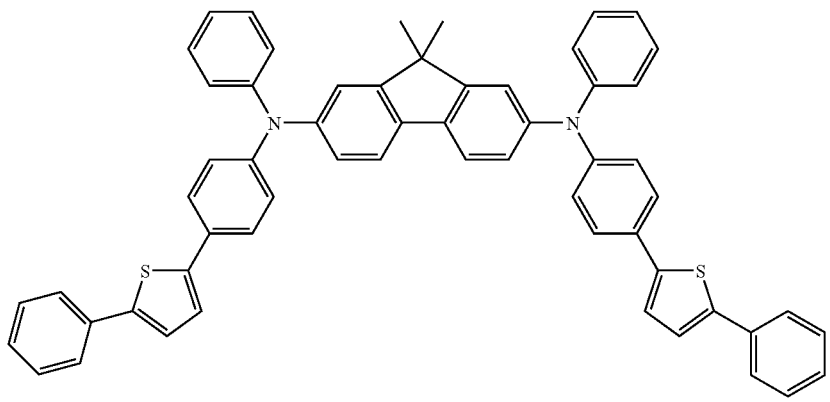
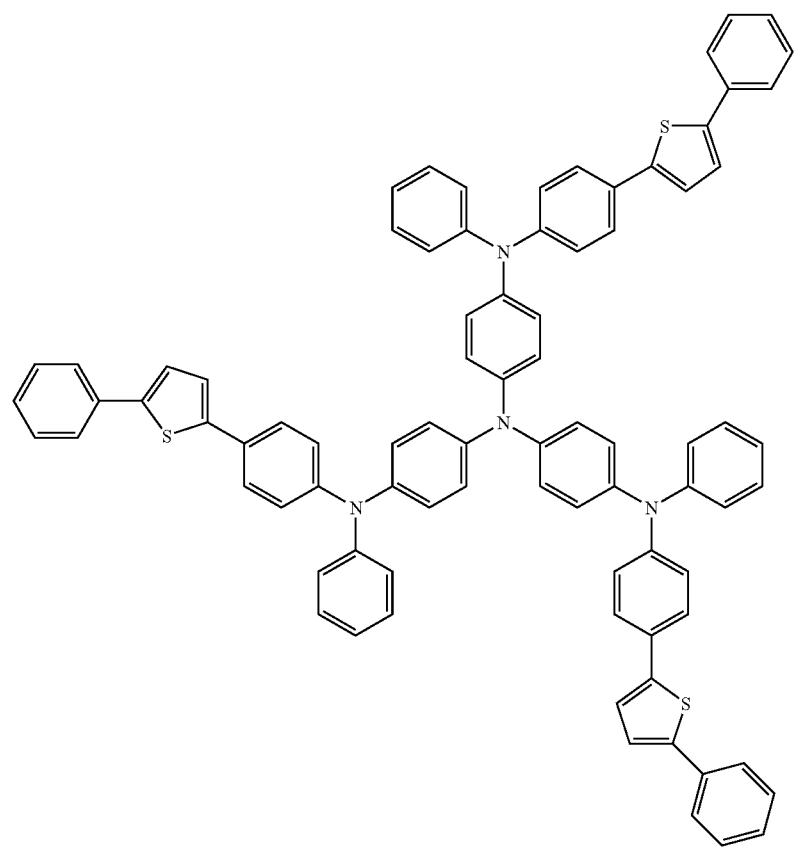

As the amine derivative contained in the hole-injecting layer 20, diamines, triamines and tetraamines can be used, and the following tetraamines may be mentioned, for example:
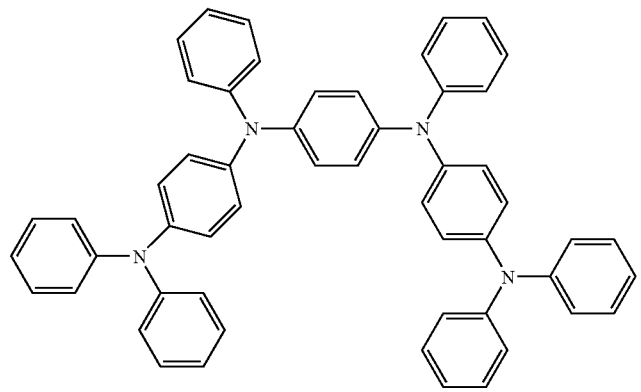
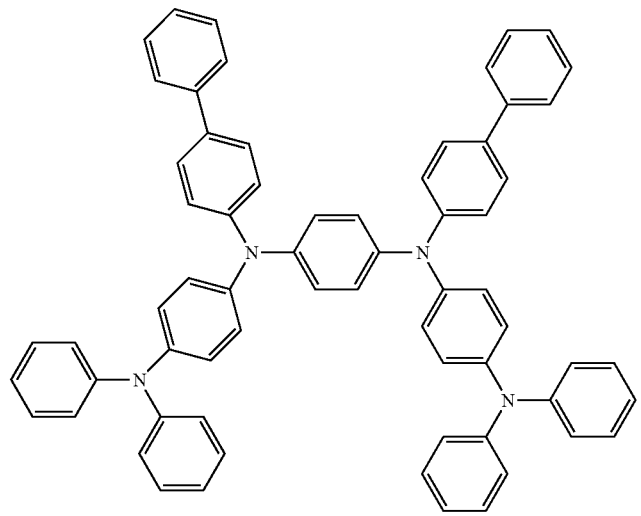
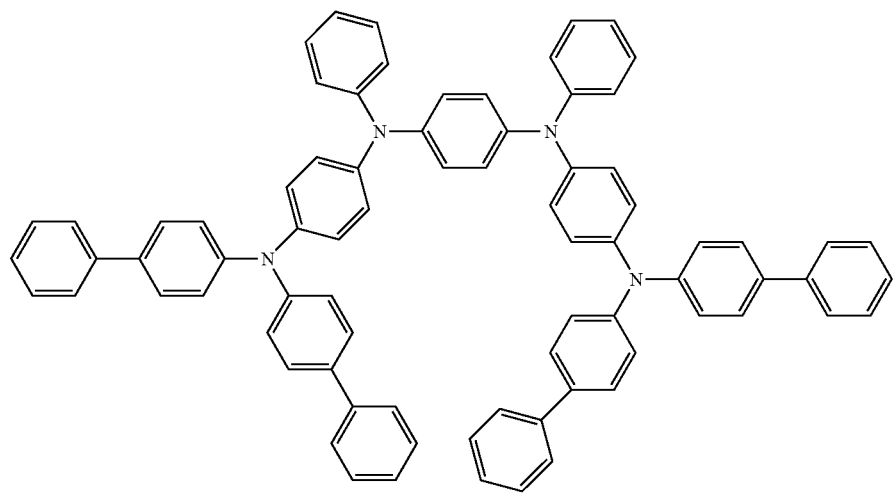

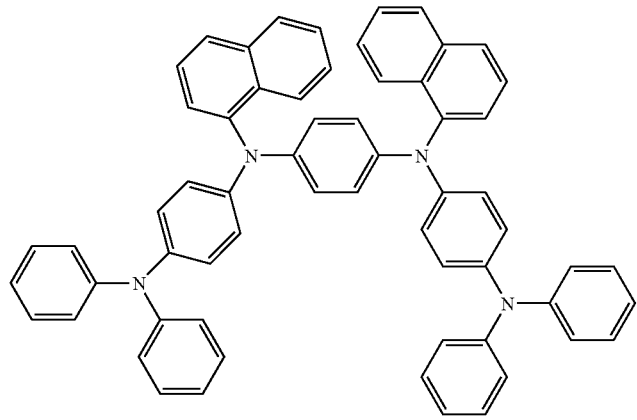
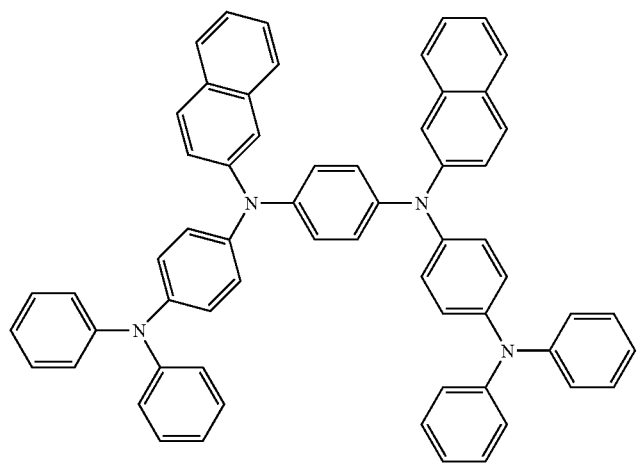
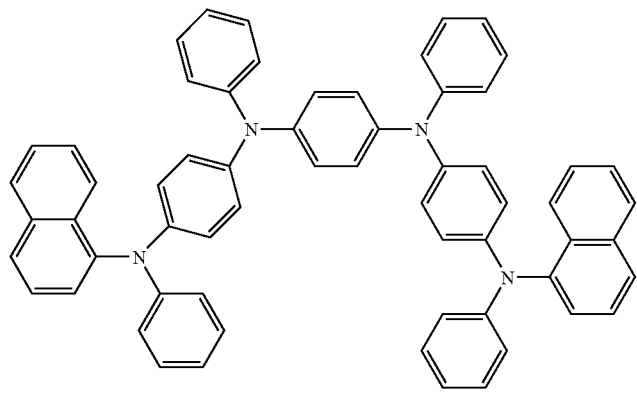
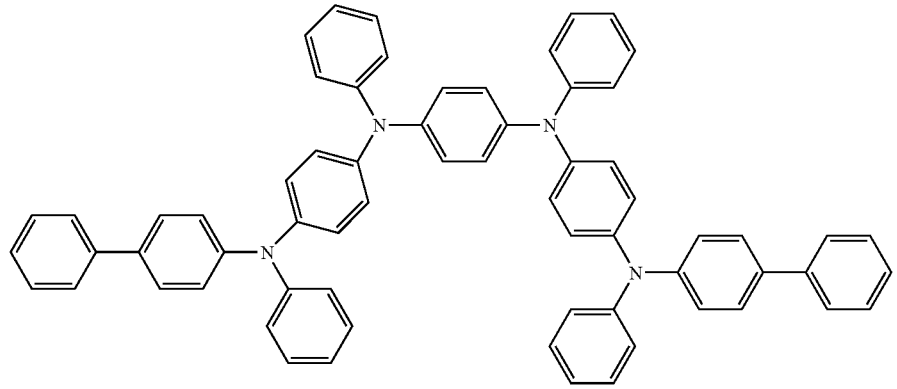

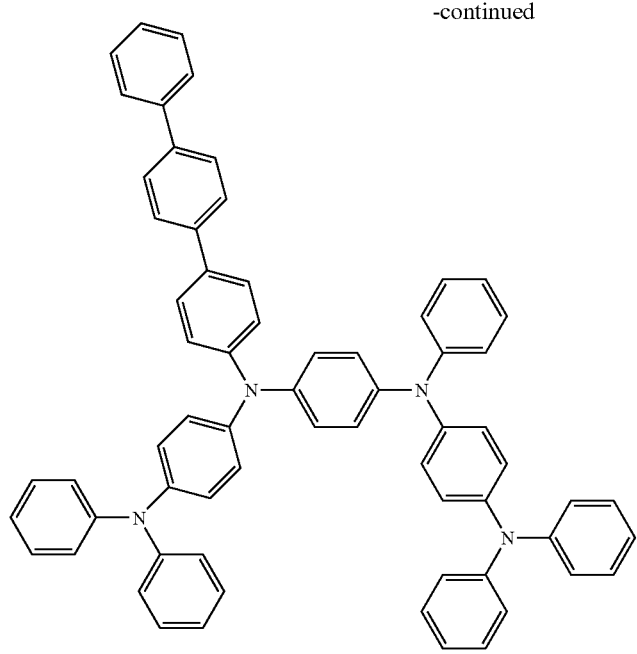
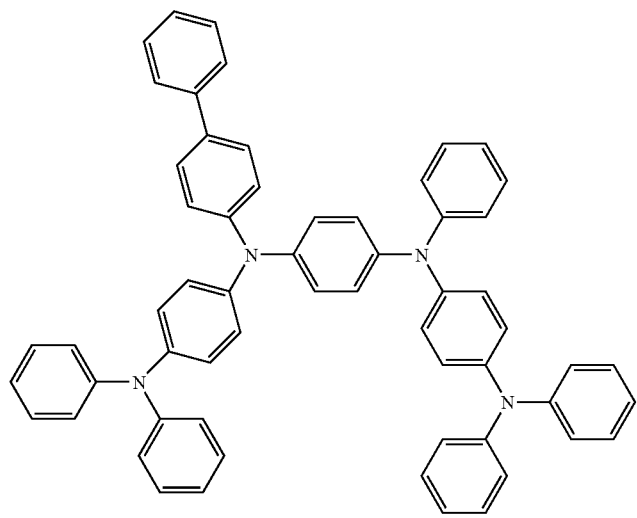
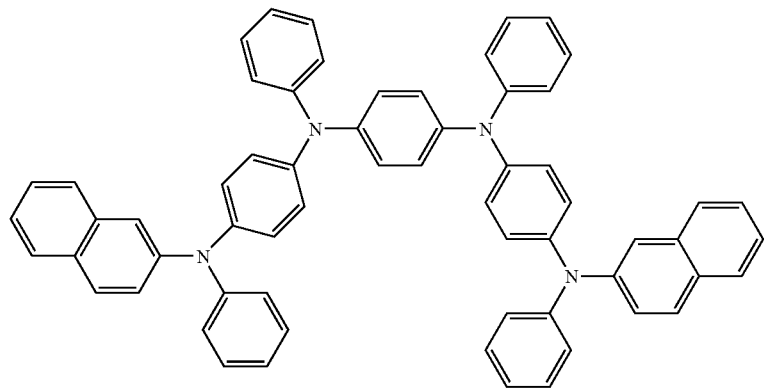

-continued
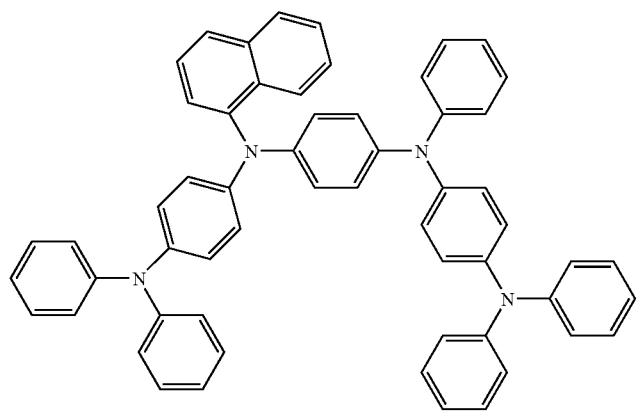
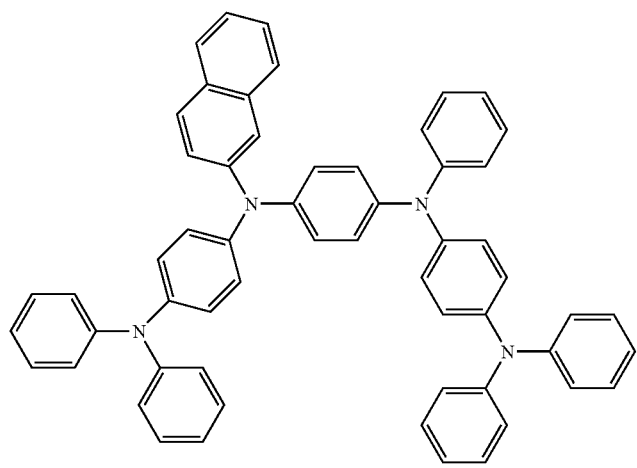
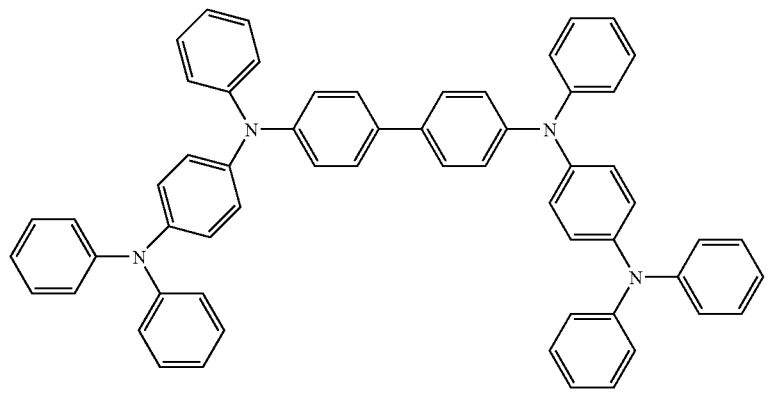

-continued
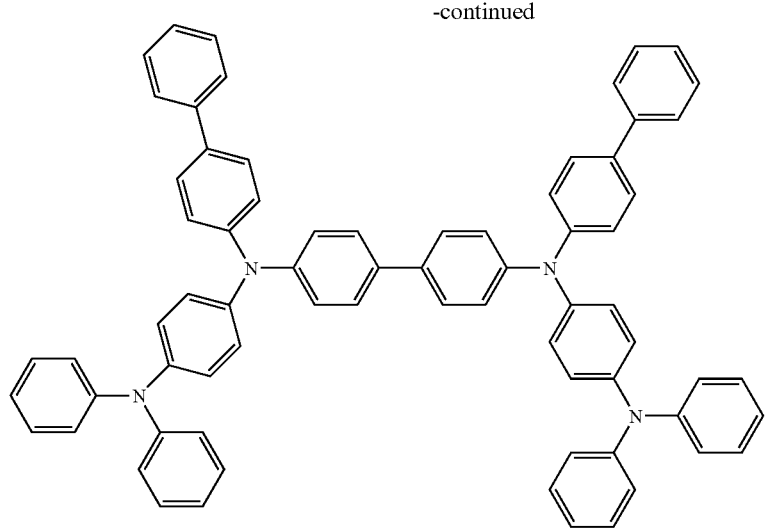
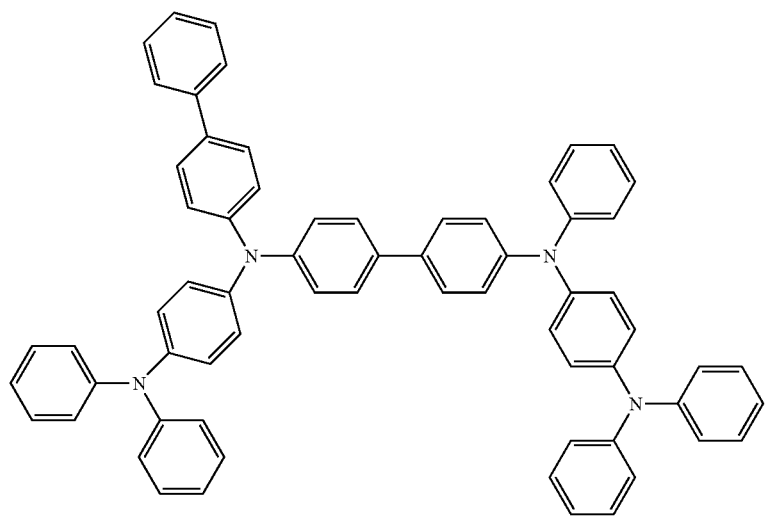
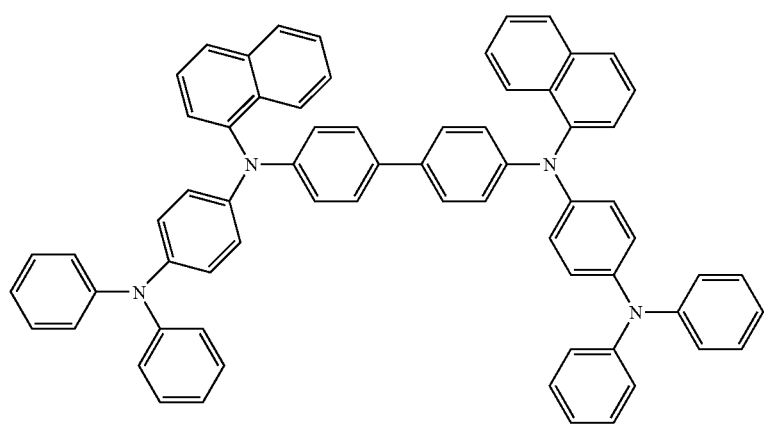

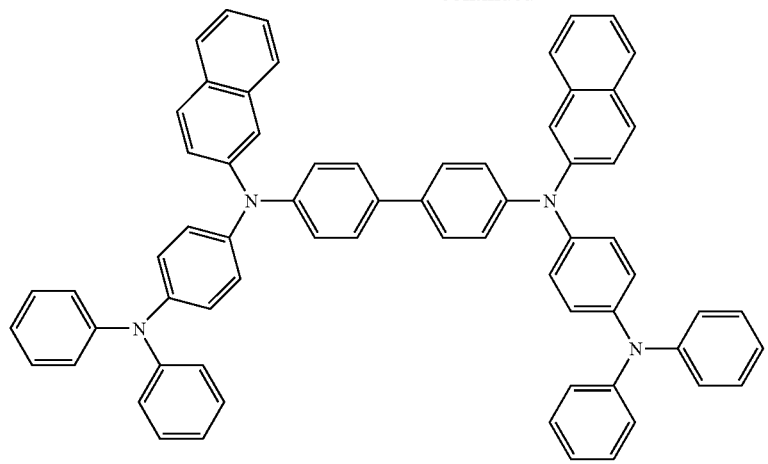
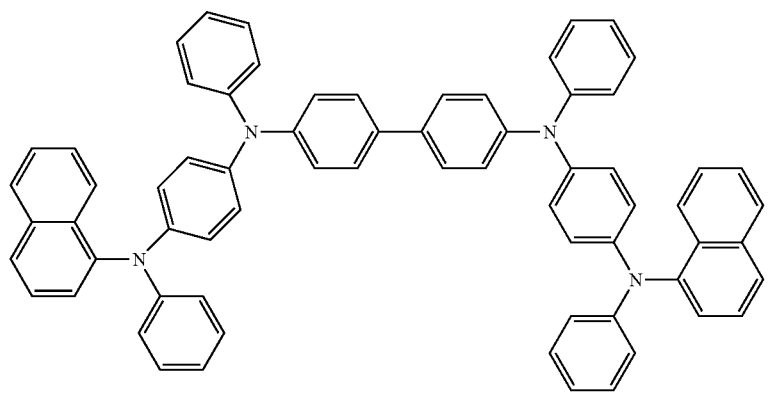
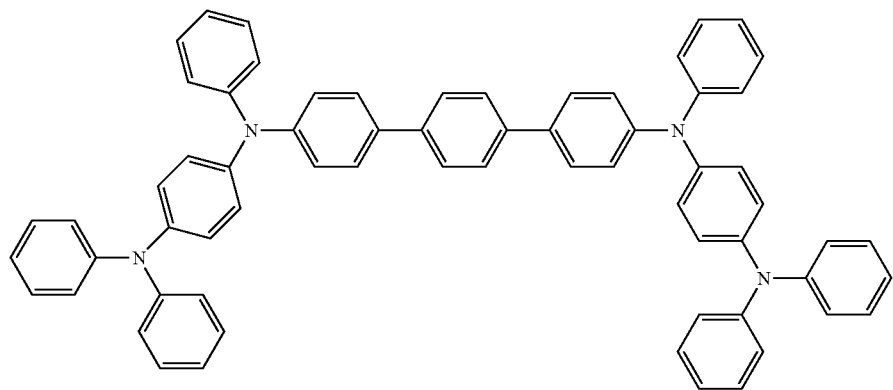

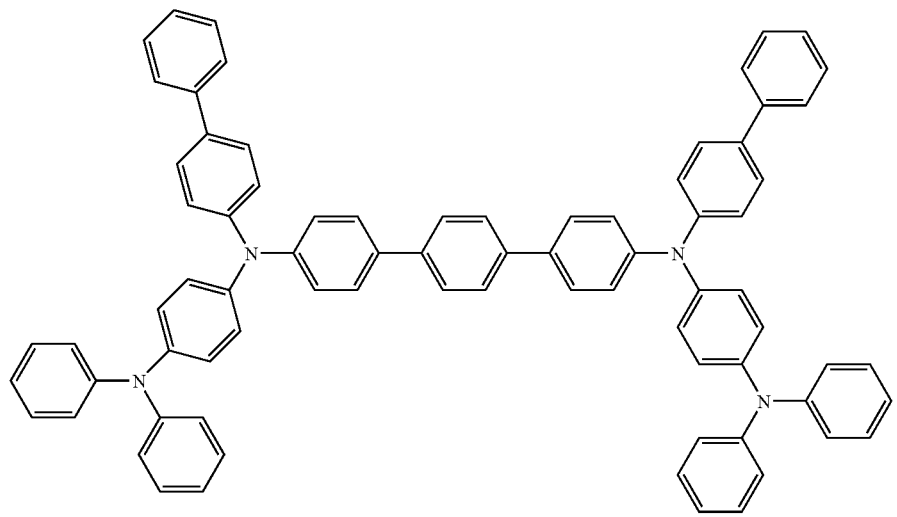
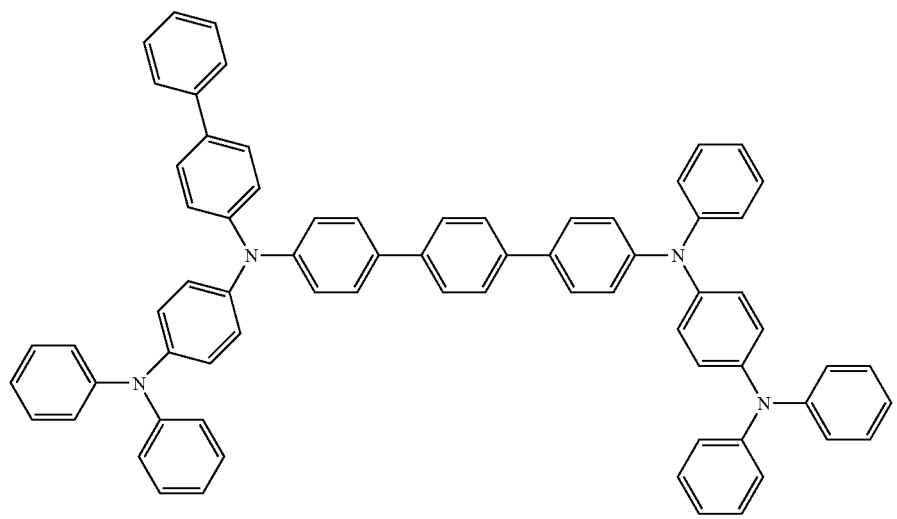
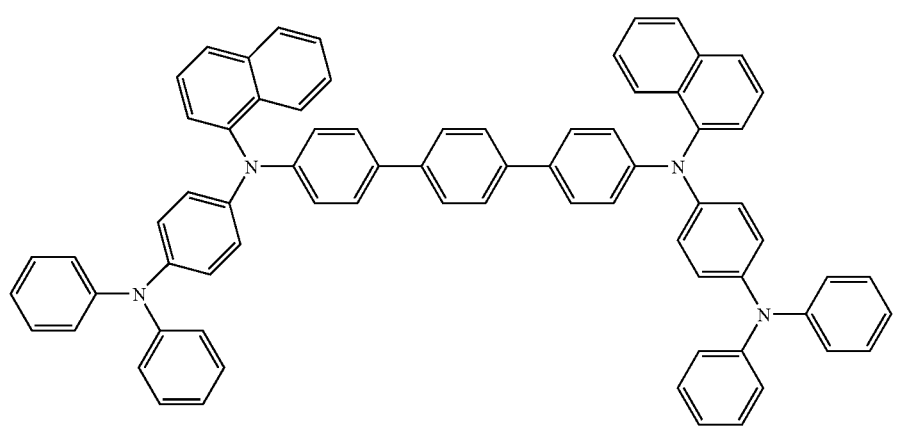

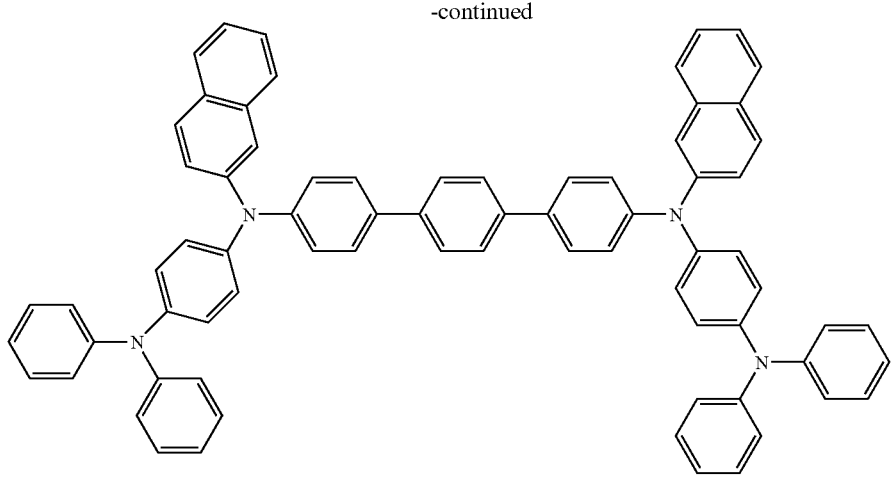
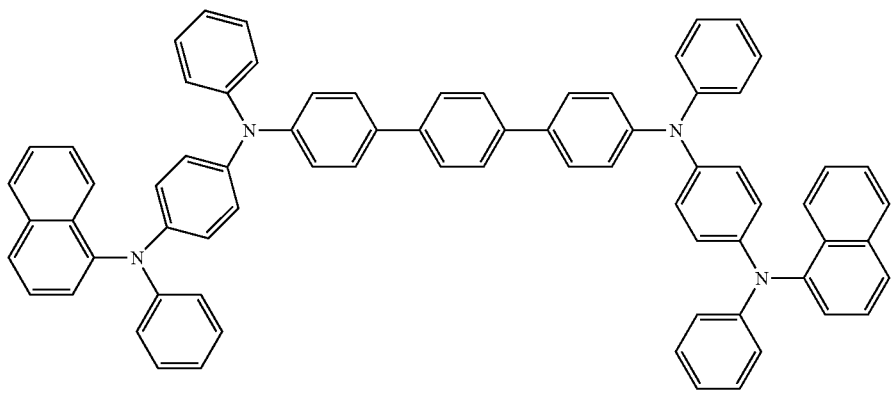
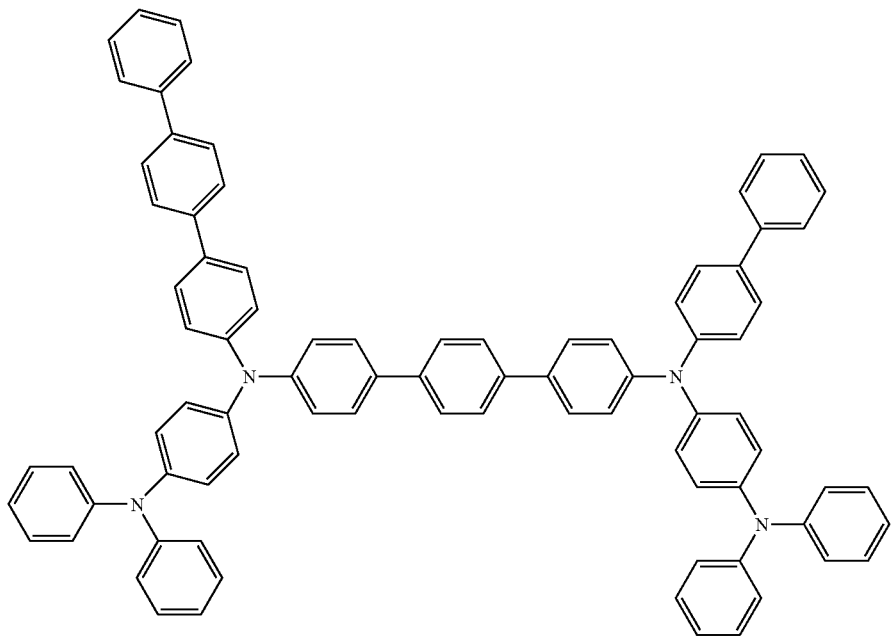

-continued
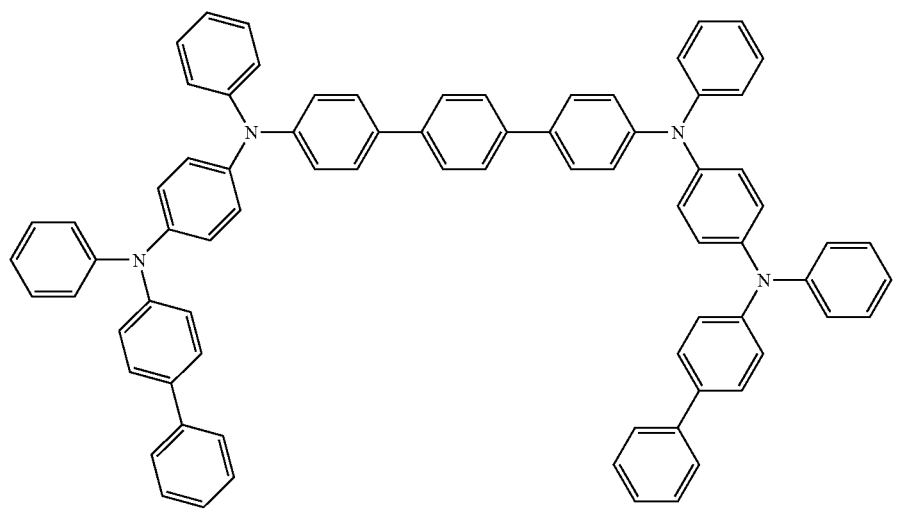
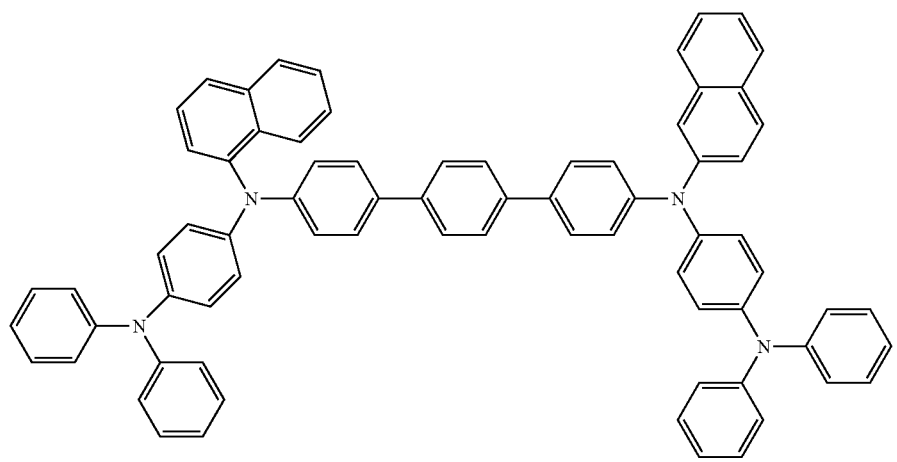
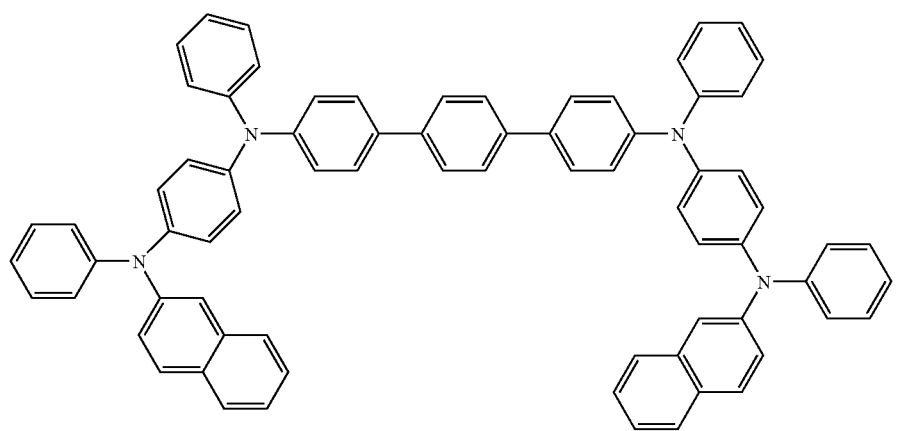

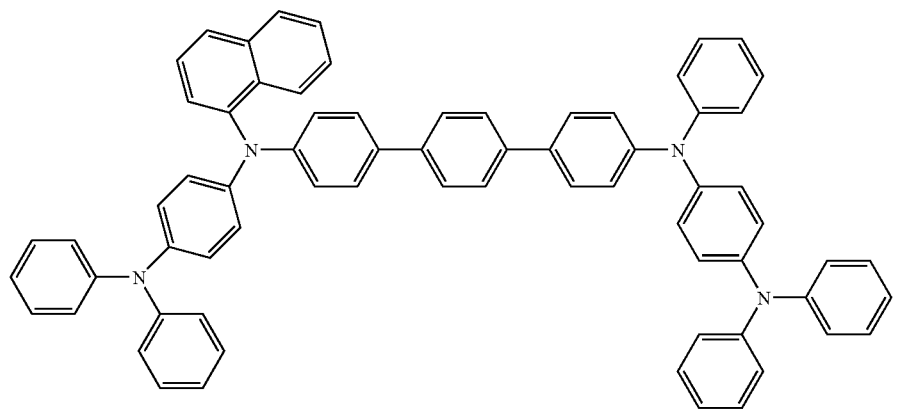
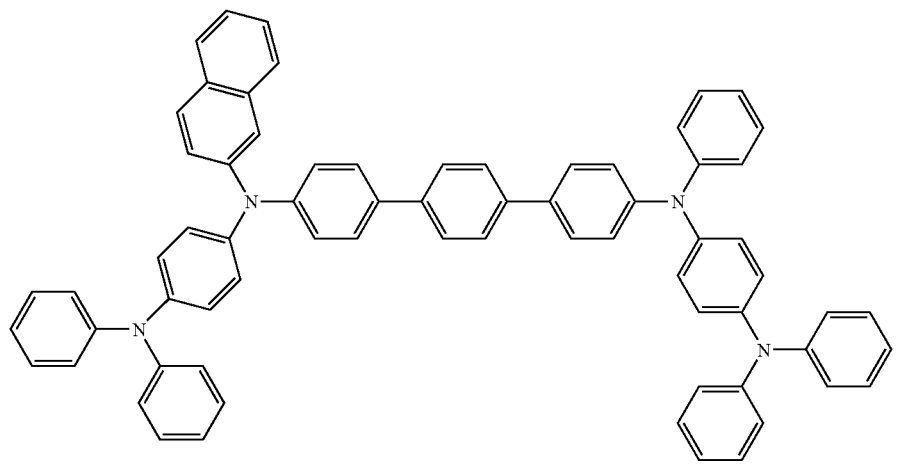
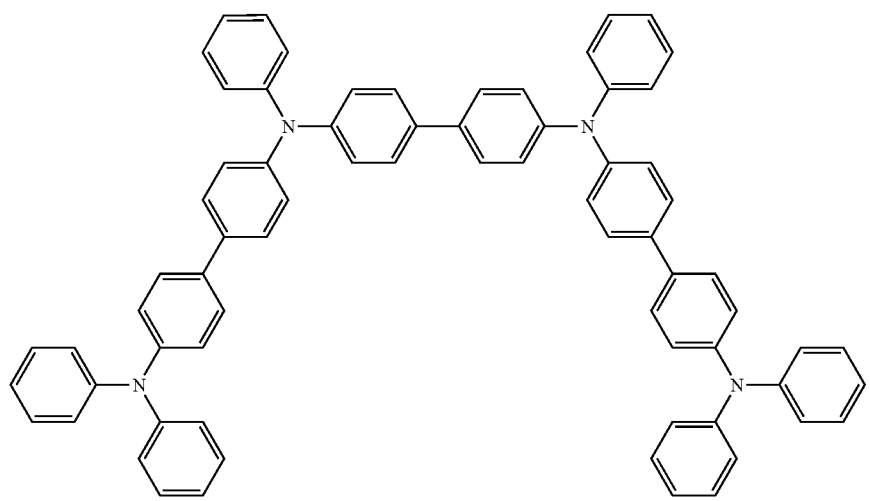

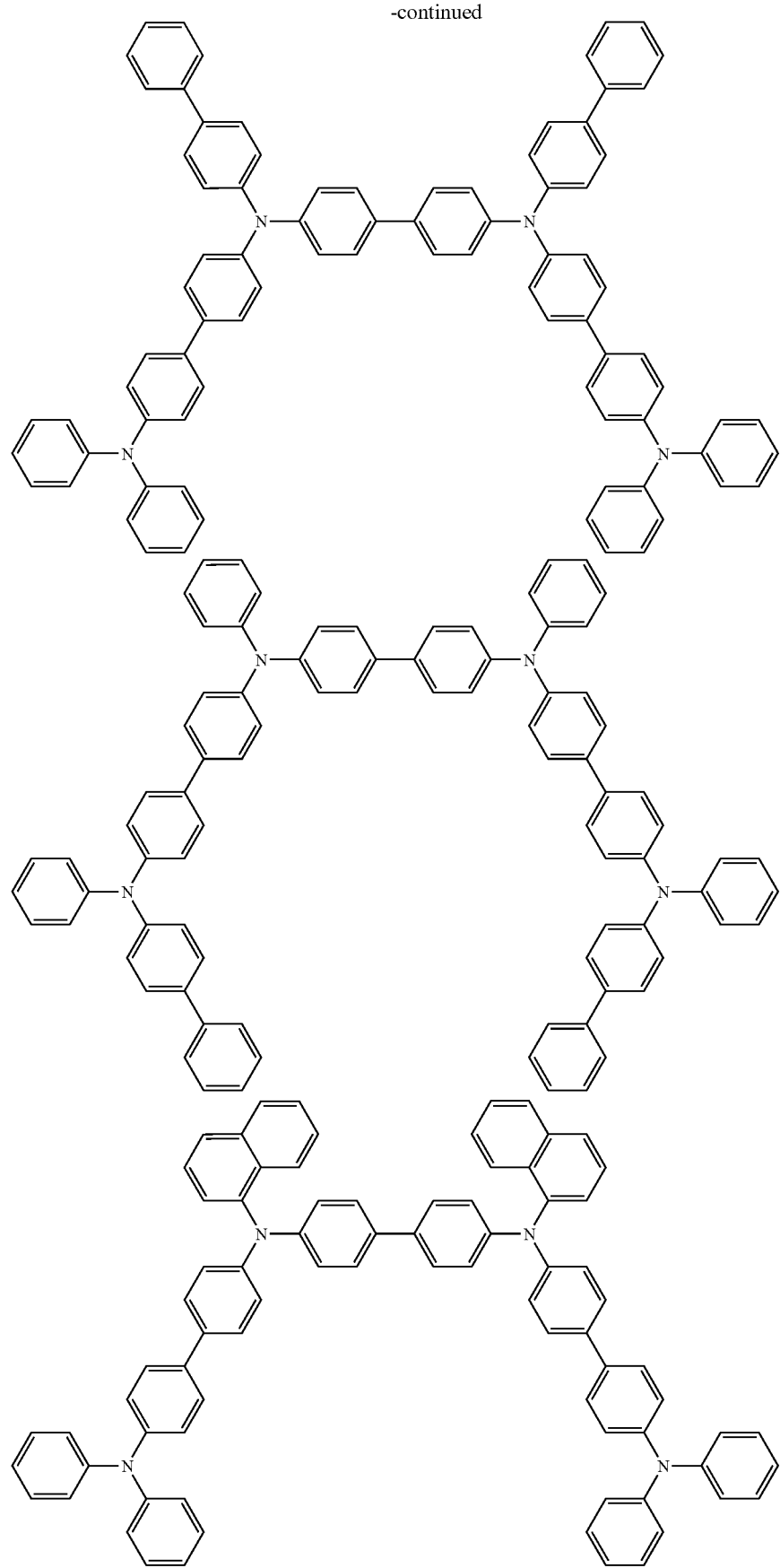

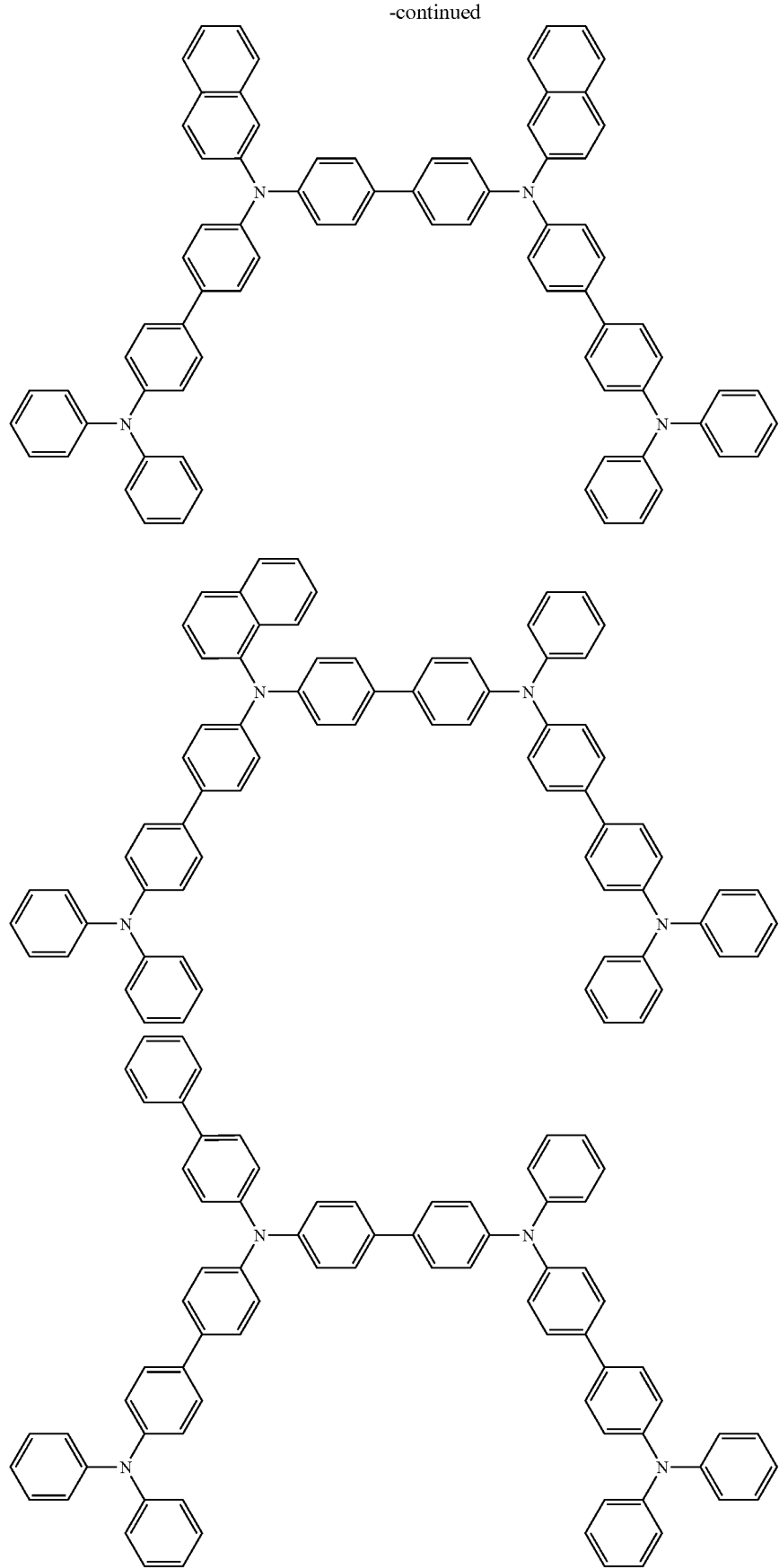

-continued
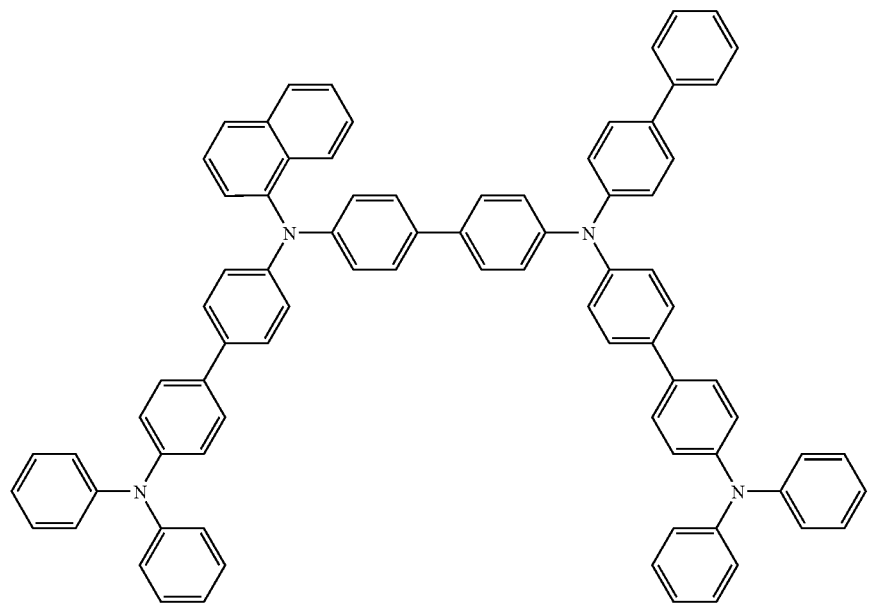
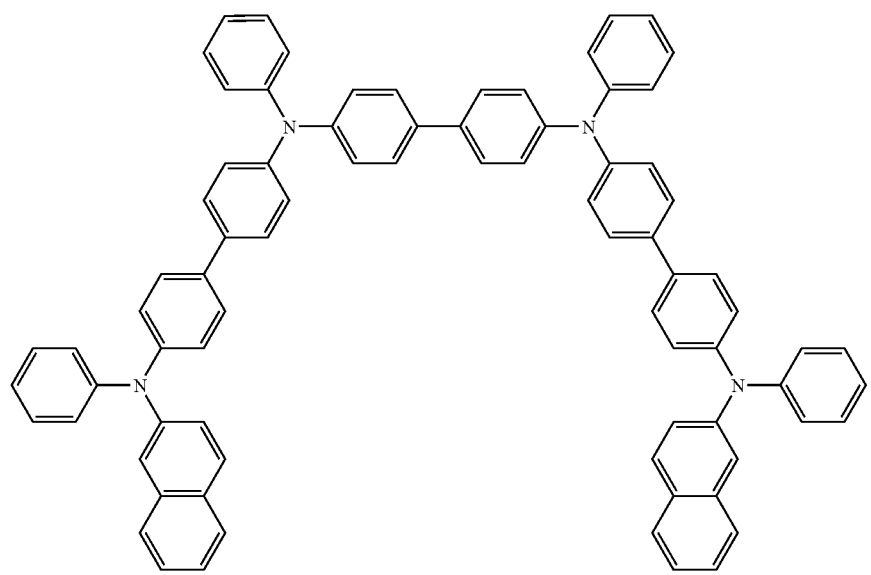

-continued
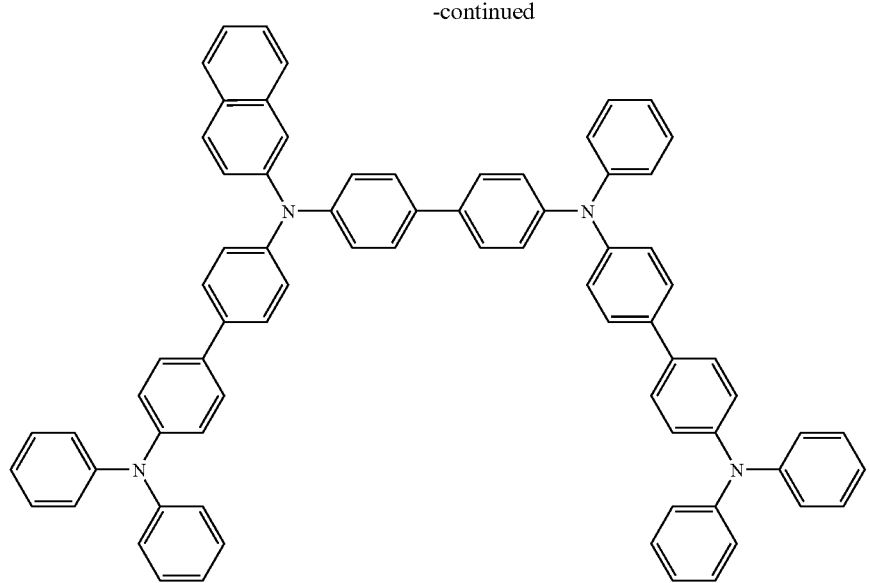
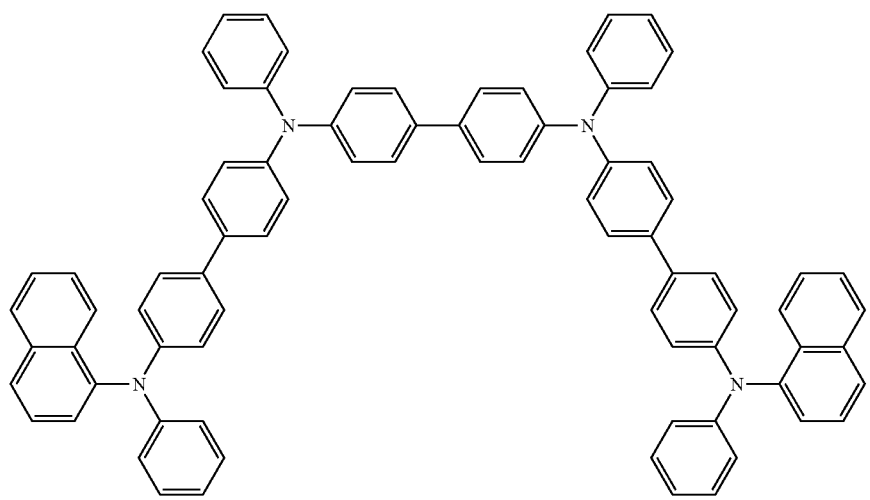
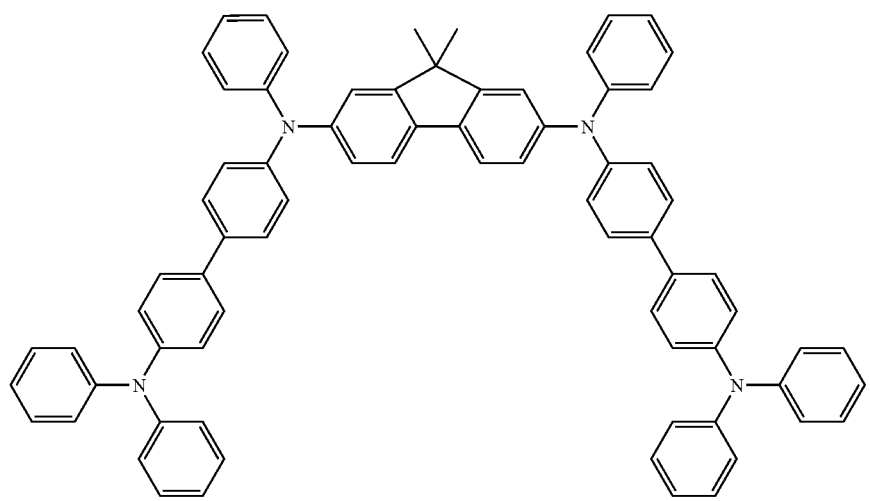

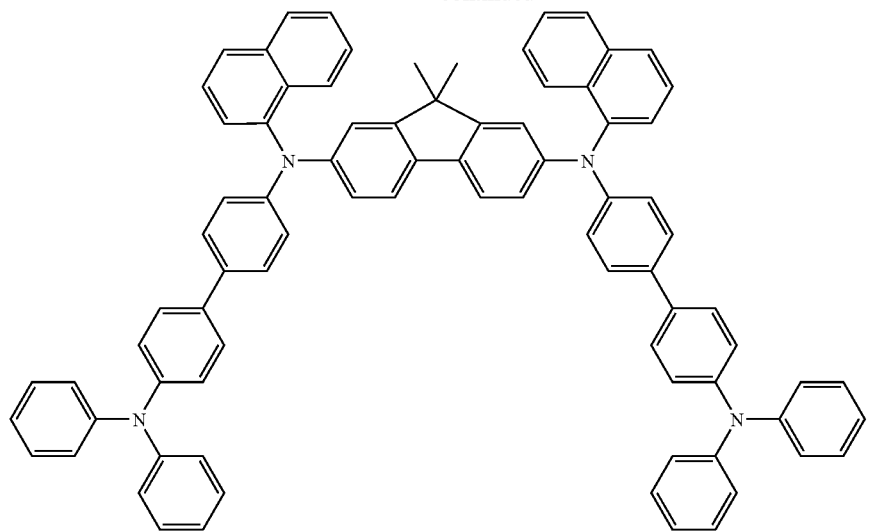
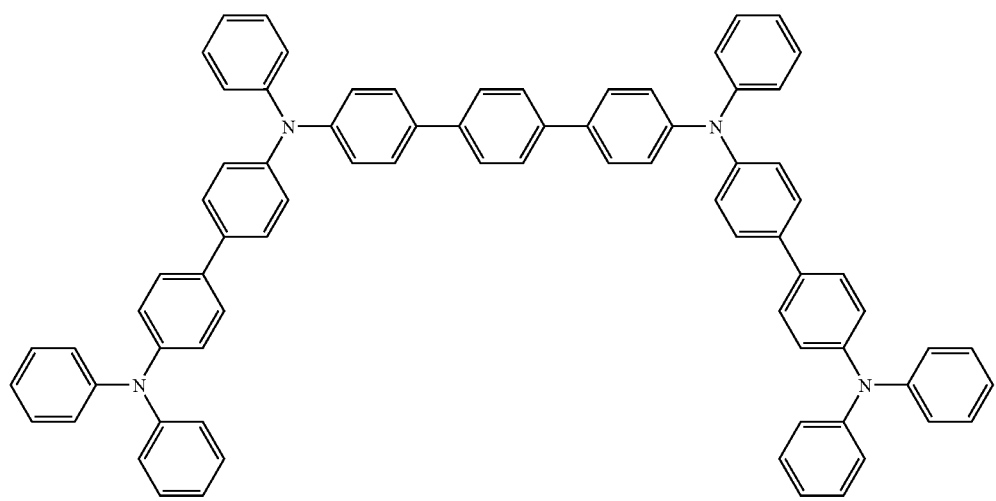
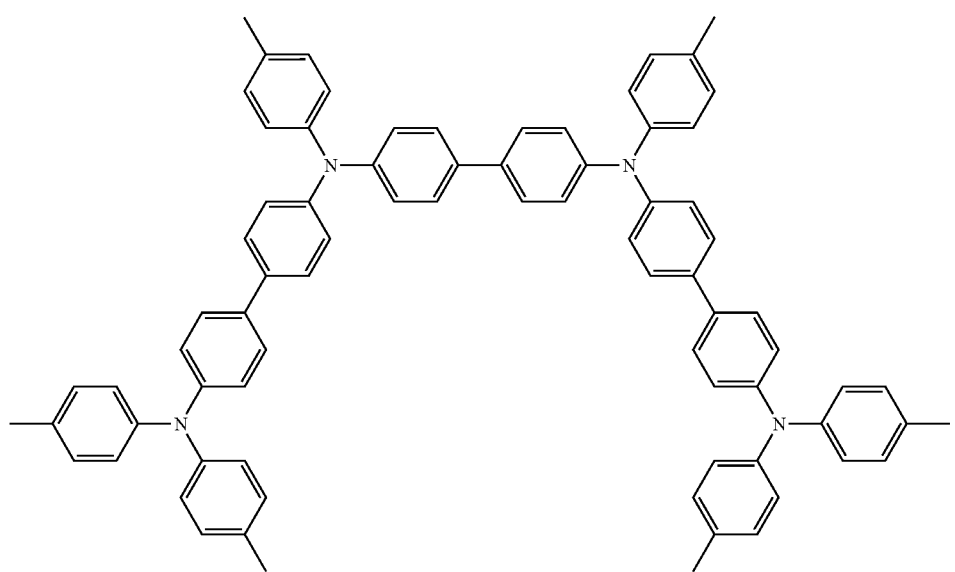

-continued

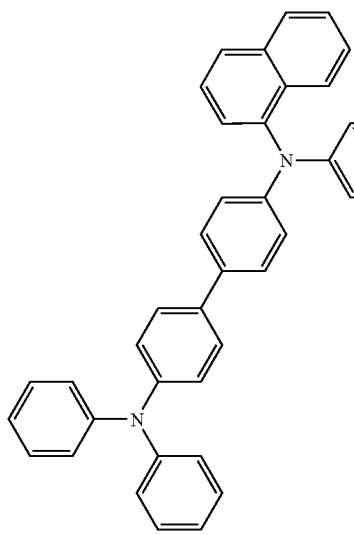
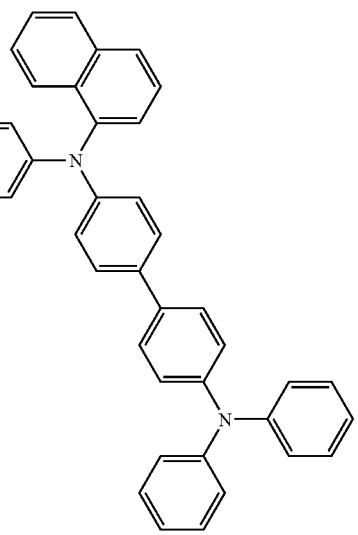

The conductive polymers contained in the hole-injecting layer 20 include PEDOT:PSS, PVTPA2:TBPAH and PTP-DEK:TBPAH.

The transition metal oxides contained in the hole-injecting layer 20 include NbO, LaO, NdO, SmO, $EuO_x$, $MoO_3$, $MoO_2$, $ReO_2$, $ReO_3$, $OsO_2$, $IrO_2$, $PtO_2$, $LiTi_2O_4$, $LiV_2O_4$, $Er_xNbO_3$, $LaTiO_3$, $SrVO_3$, $CaCrO_3$, $Sr_xCrO_3$, $A_xMoO_3$ and $AV_2O_5$ (A=K, Cs, Rb, Sr, Na, Li or Ca). Of these transition metal oxides, preferred are $LiTi_2O_4$, $LiV_2O_4$, $Er_xNbO_3$, $LaTiO_3$, $SrVO_3$, $CaCrO_3$, $Sr_xCrO_3$, $A_xMoO_3$ and $AV_2O_5$ (A=K, Cs, Rb, Sr, Na, Li or Ca).

The fullerenes contained in the hole-injecting layer 20 include carbon cluster compounds as represented by $C_{60}$, for example, and $C_{70}$, $C_{76}$, $C_{78}$, $C_{82}$, $C_{84}$, $C_{90}$, $C_{96}$, etc. other than $C_{60}$ may be used.

The acceptor material contained in the hole-injecting layer 20 is preferably an organic compound having an electron-attracting substituent or an electron-deficient ring.

As examples of the electron-attracting substituent, halogen, CN—, a carbonyl group, an aryl boron group, and the like can be given.

As examples of the electron-deficient ring, a compound selected from the group consisting of 2-pyridyl, 3-pyridyl, 4-pyridyl, 2-quinolyl, 3-quinolyl, 4-quinolyl, 2-imidazole, 4-imidazole, 3-pyrazole, 4-pyrazole, pyridazine, pyrimidine, pyrazine, cinnoline, phthalazine, quinazoline, quinoxaline, 3-(1,2,4-N)-triazolyl, 5-(1,2,4-N)-triazolyl, 5-tetrazolyl, 4-(1-O,3-N)-oxazole, 5-(1-O,3-N)-oxazole, 4-(1-S,3-N)-thiazole, 5-(1-S,3-N)-thiazole, 2-benzoxazole, 2-benzothiazole, 4-(1,2,3-N)-benzotriazole, and benzimidazole, and the like can be given. Note that the electron-deficient ring is not limited thereto.

The acceptor materials are preferably quinodimethane derivatives.

As quinoid derivatives, compounds represented by the following formulas (1a) to (1i), and more preferred are the compounds represented by the formulas (1a) and (1b):

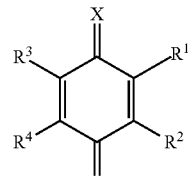 (1a)

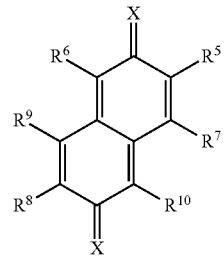 (1b)

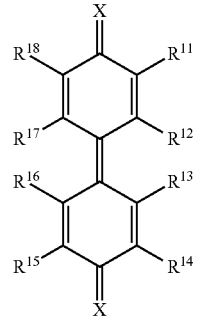 (1c)

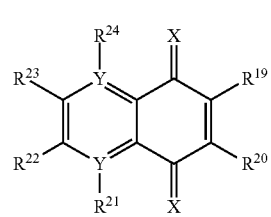 (1d)

(1e)

(1f)

(1g)

(1h)

(1i)

In the formulas (1a) to (1i), $R^1$ to $R^{48}$ are independently hydrogen, halogen, a fluoroalkyl group, cyano group, alkoxy group, alkyl group, or aryl group, and preferably hydrogen and a cyano group.

In the formulas (1a) to (1i), X is an electron-attracting group having one of the structures of the following formulas (j) to (p). The structures of the formulas (j), (k), and (l) are preferable.

(j)

(k)

(l)

(m)

(n)

(o)

(p)

wherein $R^{49}$ to $R^{52}$ are independently are hydrogen, a fluoroalkyl group, alkyl group, aryl group, or heterocyclic ring, provided that $R^{50}$ and $R^{51}$ may form a ring.

In the formulas (1a) to (1i), Y is —N═ or —CH═.

As the halogen represented by $R^1$ to $R^{48}$, fluorine and chlorine are preferable.

As the fluoroalkyl group represented by $R^1$ to $R^{48}$, a trifluoromethyl group and a pentafluoroethyl group are preferable.

As the alkoxy group represented by $R^1$ to $R^{48}$, a methoxy group, ethoxy group, iso-propoxy group, and tert-butoxy group are preferable.

As the alkyl group represented by $R^1$ to $R^{48}$, a methyl group, ethyl group, propyl group, iso-propyl group, tert-butyl group, and cyclohexyl group are preferable.

As the aryl group represented by $R^1$ to $R^{48}$, a phenyl group and naphthyl group are preferable.

The fluoroalkyl group, alkyl group, and aryl group represented by $R^{49}$ to $R^{52}$ are the same as those of $R^1$ to $R^{48}$.

As the heterocyclic ring represented by $R^{49}$ to $R^{52}$, substituents of the following formulas are preferable.

When $R^{50}$ and $R^{51}$ form a ring, X is preferably a substituent of the following formula.

wherein $R^{51'}$ and $R^{52'}$ are independently a methyl group, ethyl group, propyl group, or tert-butyl group.

As specific examples of the quinoid derivative, the following compounds can be given.

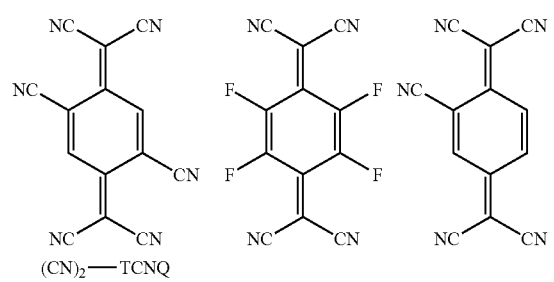
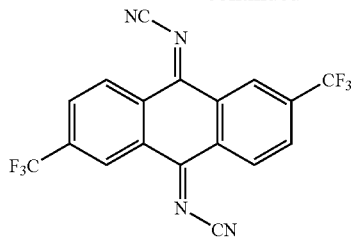
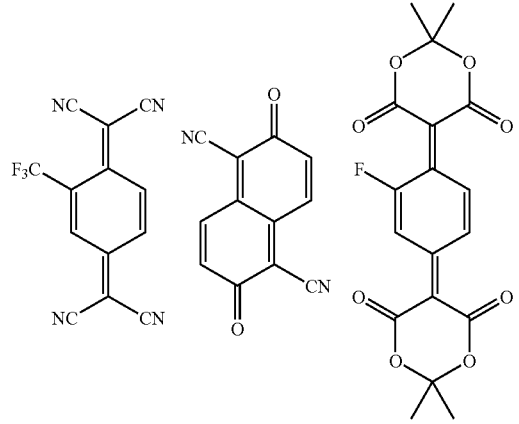
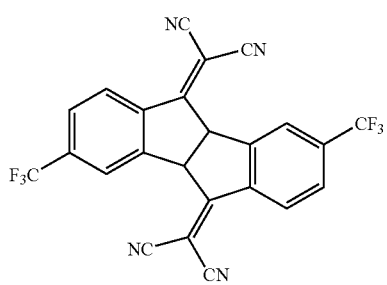
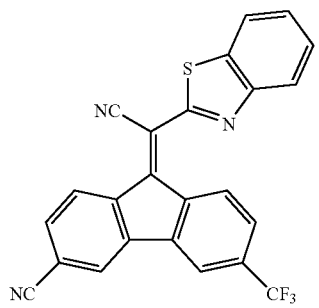
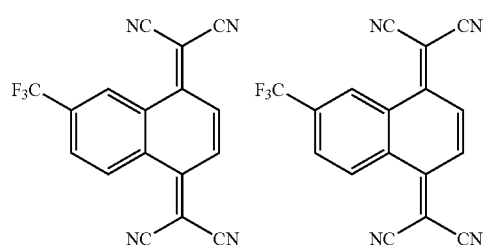
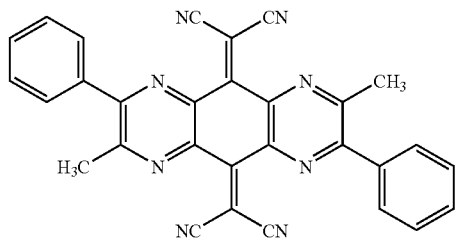
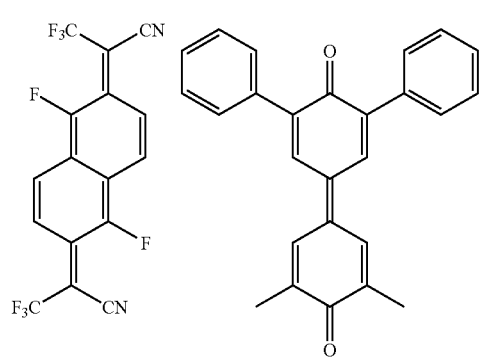
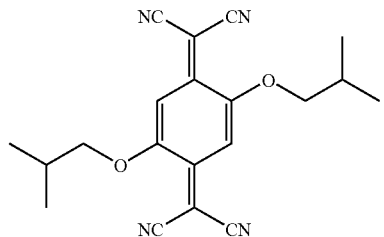
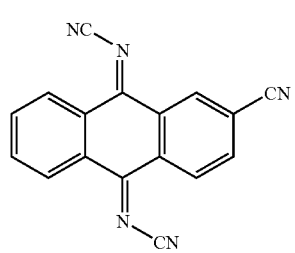
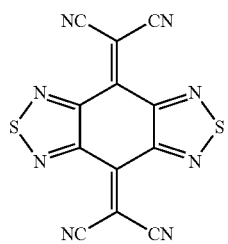

It is preferred that the acceptor be capable of being formed into a thin film. Namely, by only deposition of the acceptor, an acceptor-containing layer can be formed. The expression "capable of being formed into a thin film" means capable of being formed into a smooth, thin film on a substrate by a common thin film-forming method such as vacuum vapor deposition and spin coating. Here, the "smooth" means a smaller degree of the roughness of the thin film. The surface roughness (Ra) is preferably 10 nm or less, more preferably 1.5 nm or less, still more preferably 1 nm or less. The surface roughness can be measured by means of an atomic force microscope (AFM).

As organic compounds capable of being formed into a thin film, amorphous organic compounds are preferable, with amorphous quinodimethane derivatives being still more preferable. An amorphous quinodimethane derivative having 5 or more CN-groups is further preferable. For example, $(CN)_2$-TCNQ as mentioned above can be given.

The content of an acceptor contained in the acceptor-containing layer is preferably 1 to 100 mole %, more preferably 50 to 100 mole %, relative to the whole layer. The acceptor-containing layer may contain a compound having hole transporting property and light transmitting property in addition to the acceptor.

A donor may be added to the acceptor-containing layer in order to facilitate injection of electrons to the donor-containing layer or to facilitate transport of holes to the cathode. Such a donor is a compound capable of transferring electrons to a compound contained in the acceptor-containing layer other than the donor or a compound contained in an adjacent layer.

As the donor, organic donor compounds such as amine compounds, polyamine compounds and tungsten complexes may be mentioned in addition to the above-mentioned donor metals.

(B) The layer (hole-transporting layer 30) which is arranged in the hole-injection and transport region and in contact with the emitting layer contains an aromatic amine derivative having a carbazole skeleton. By containing the aromatic amine derivative having a carbazole skeleton in the hole-transporting layer 30, driving voltage of the device does not increase and the device can have high luminous efficiency and long life time.

The aromatic amine derivative having a carbazole skeleton is preferably a compound represented by the following formula (1), or a compound represented by the following formula (2):

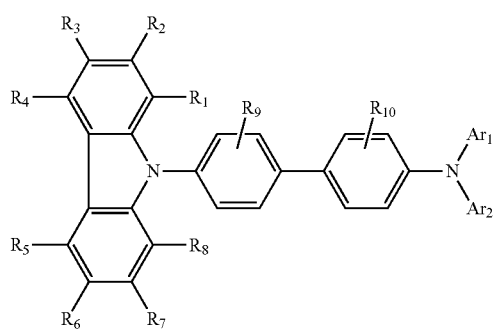

(1)

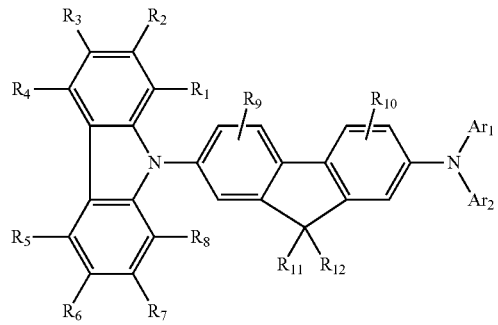

(2)

In the formula (1) or (2), $Ar_1$ and $Ar_2$ are independently an aromatic hydrocarbon ring group or an aromatic heterocyclic group which may have a substituent.

The aromatic hydrocarbon ring group for $Ar_1$ and $Ar_2$ include groups of a single benzene ring, or groups of two to five benzene rings being fused. Specifically, a phenyl group, a naphthyl group, an anthryl group, a phenanthryl group, a pyrenyl group, a perylenyl group and the like may be mentioned. The aromatic heterocyclic group includes a 5- or 6-membered single ring, or a fused ring composed of 2 to 5 5- or 6-membered rings. Specifically, a pyridyl group, a triazinyl group, a pyrazinyl group, a quinoxalinyl group, a thienyl group and the like may be mentioned.

The substituents which the aromatic hydrocarbon ring group and the aromatic heterocyclic group can have include alkyl groups (linear or branched alkyl groups having 1 to 6 carbon atoms such as a methyl group and an ethyl group), alkenyl groups (linear or branched alkenyl groups having 1 to 6 carbon atoms such as a vinyl group and an allyl group), alkoxycarbonyl groups (linear or branched alkoxycarbonyl groups having 1 to 6 carbon atoms such as a methoxycarbonyl group and an ethoxycarbonyl group), alkoxy groups (linear or branched alkoxy groups having 1 to 6 carbon atoms such as a methoxy group and an ethoxy group), aryloxy groups (aryloxy groups having 6 to 10 carbon atoms such as a phenoxy group and a naphthoxy group), aralkyloxy groups (aryloxy groups having 7 to 13 carbon atoms such as a benzyloxy group), secondary or tertiary amino groups (dialkyl amino groups having a linear or branched alkyl group having 2 to 20 carbon atoms such as a diethyl amino group and a diisopropyl amino group; diaryl amino groups such as a diphenyl amino group and a phenyl naphthyl amino group; and aryl alkyl amino groups having 7 to 20 carbon atoms such as a methyl phenyl amino group), halogen atoms (a fluorine atom, a chlorine atom, a bromine atom and an iodine atom), aromatic hydrocarbon ring groups (aromatic hydrocarbon ring groups having 6 to 10 carbon atoms such as a phenyl group and a naphthyl group) and aromatic heterocyclic groups (aromatic heterocyclic groups composed of a 5- or 6-membered single ring or fused rings of two 5- or 6-membered rings such as a thienyl group and a pyridyl group).

Of these, an alkyl group, an alkoxy group, an alkylamino group, an arylamino group, an aryl alkyl amino group, a halogen atom, an aromatic hydrocarbon ring group and an aromatic heterocyclic group are preferable, and an alkyl group, an alkoxy group and an arylamino group are particularly preferable.

In the formula (1) or (2), $R_1$ to $R_{12}$ are independently a hydrogen atom, a halogen atom, an alkyl group, an aralkyl group, an alkenyl group, a cyano group, an amino group, an acyl group, an alkoxycarbonyl group, a carboxy group, an alkoxy group, an aryloxy group, an alkylsulfonyl group, a hydroxy group, an amido group, an aromatic hydrocarbon ring group or an aromatic heterocyclic group, and these may be further substituted. Adjacent groups of $R_1$ to $R_{12}$ may form a ring.

Specific examples of $R_1$ to $R_{12}$ include a hydrogen atom, halogen atoms (a fluorine atom, a chlorine atom, a bromine atom and an iodine atom), alkyl groups (linear or branched alkyl groups having 1 to 6 carbon atoms such as a methyl group and an ethyl group; cycloalkyl groups having 5 to 8 carbon atoms such as a cyclopentyl group and a cyclohexyl group), aralkyl groups (aralkyl groups having 7 to 13 carbon atoms such as a benzyl group and a phenetyl group), alkenyl groups (linear or branched alkenyl groups having 2 to 7 carbon atoms such as a vinyl group and an allyl group), cyano groups, amino groups, particularly a tertiary amino group (dialkyl amino groups having a linear or branched alkyl group having 2 to 20 carbon atoms such as a diethyl amino group and a diisopropyl amino group; a diaryl amino group such as a diphenyl amino group and a phenyl naphthyl amino group; and aryl alkyl amino groups having 7 to 20 carbon atoms such as a methyl phenyl amino group), acyl groups (an acyl group having a linear, branched or cyclic hydrocarbon group moiety having 1 to 20 carbon atoms such as an acetyl group, a propionyl group, a benzoyl group and a naphthoyl group), alkoxycarbonyl groups (linear or branched alkoxycarbonyl groups having 2 to 7 carbon atoms such as a methoxycarbonyl group and an ethoxycarbonyl group), carboxyl groups, alkoxy groups (linear or branched alkoxy groups having 1 to 6 carbon atoms such as a methoxy group and an ethoxy group), aryloxy groups (aryloxy groups having 6 to 10 carbon atoms such as a phenoxy group and a benzyloxy group), alkylsulfonyl groups (alkyl sulfonyl groups having 1 to 6 carbon atoms such as a methylsulfonyl group, an ethylsulfonyl group, a propylsulfonyl group, a butylsulfonyl group and a hexylsulfonyl group), hydroxy groups, amido groups (alkylamido groups having 2 to 7 carbon atoms such as a methylamido group, a dimethylamido group and a diethylamido group; arylamido groups such as a benzylamido group and a dibenzylamido group; etc.), aromatic hydrocarbon ring groups (aromatic hydrocarbon ring groups composed of a single benzene ring or a fused ring of 2 to 4 benzene rings such as a phenyl group, a naphthyl group, an anthryl group, a phenanthryl group and a pyrenyl group), and aromatic heterocyclic groups (aromatic heterocyclic groups composed of a single 5- or 6-membered ring or a fused ring of 2 to 3 rings such as a carbazolyl group, a pyridyl group, a triazyl group, a pyrazyl group, a quinoxalyl group and a thienyl group).

$R_1$ to $R_{12}$ are preferably a hydrogen atom, a halogen atom, an alkyl group, an alkoxy group, an aromatic hydrocarbon ring group or an aromatic heterocyclic group.

The substituent of $R_1$ to $R_{12}$ includes halogen atoms (a fluorine atom, a chlorine atom, a bromine atom or an iodine atom), alkyl groups (linear or branched alkyl groups having 1 to 6 carbon atoms such as a methyl group and an ethyl group), alkenyl groups (linear or branched alkenyl groups having 1 to 6 carbon atoms such as a vinyl group and an allyl group), alkoxycarbonyl groups (linear or branched alkoxycarbonyl groups having 1 to 6 carbon atoms such as a methoxycarbonyl group and an ethoxycarbonyl group), alkoxy groups (linear or branched alkoxy groups having 1 to 6 carbon atoms such as a methoxy group and an ethoxy group), aryloxy groups (aryloxy groups having 6 to 10 carbon atoms such as a phenoxy group and a naphthoxy group), dialkyl amino groups (linear or branched dialkyl amino group having 2 to 20 carbon atoms such as a diethylamino group and a diisopropyl amino group), diaryl amino groups (diaryl amino groups such as a diphenylamino group and a phenyl naphthyl amino group), aromatic hydrocarbon ring groups (aromatic hydrocarbon ring groups such as a phenyl group), aromatic heterocyclic groups (aromatic heterocyclic groups composed of a 5- or 6-membered single ring such as a thienyl group and a pyridyl group), acyl groups (linear or branched acyl groups having 1 to 6 carbon atoms such as acetyl group and a propionyl group), haloalkyl groups (linear or branched haloalkyl groups having 1 to 6 carbon atoms such as a trifluoromethyl group) and a cyano group. Of these, a halogen atom, an alkoxy group and an aromatic hydrocarbon ring group are more preferable.

Adjacent groups of $R_1$ to $R_{12}$ may form a ring. For example, adjacent groups of $R_1$ to $R_8$ may bond to each other to form a ring fused to the N-carbazolyl group. The ring formed by bonding adjacent groups of $R_1$ to $R_8$ is normally a 5- to 8-membered ring, preferably a 5- or 6-membered ring, more preferably a 6-membered ring. This ring may be an aromatic ring or a non-aromatic ring but preferred is an aromatic ring. Further, the ring may be an aromatic hydrocarbon ring or an aromatic heterocyclic ring but preferred is an aromatic hydrocarbon ring.

In the N-carbazolyl group in the formula (1) or (2), examples of a ring fused to the N-carbazolyl group, which is formed by bonding adjacent groups of $R_1$ to $R_8$ to each other include the followings:

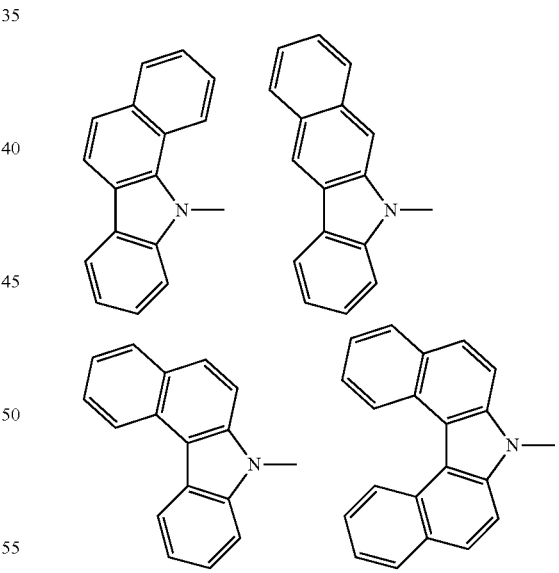

Particularly preferably, all of $R_1$ to $R_8$ are a hydrogen atom (i.e. the N-carbazolyl group has no substituent), or one or more thereof are a methyl group, a phenyl group or a methoxy group and the residues thereof are a hydrogen atom.

The carbazole skeleton of the aromatic amine derivative having a carbazole skeleton is preferably a monocarbazolyl group. Specific examples of the aromatic amine derivative having a carbazole skeleton, which can be used for the first embodiment of the invention, are shown below:

A-1
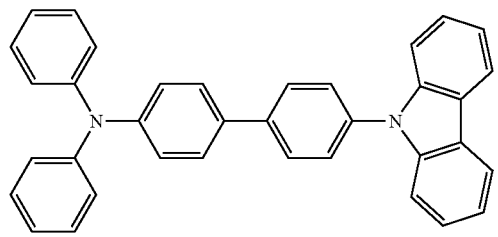
A-2
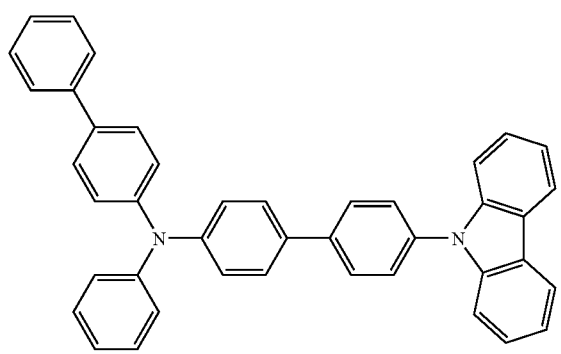
A-3
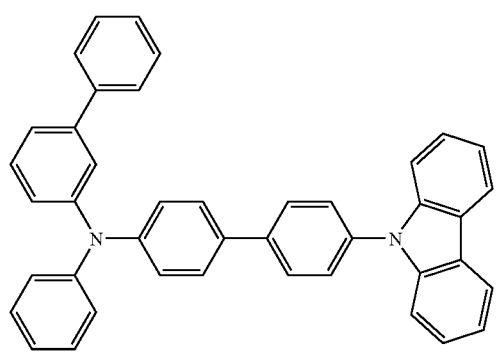
A-4
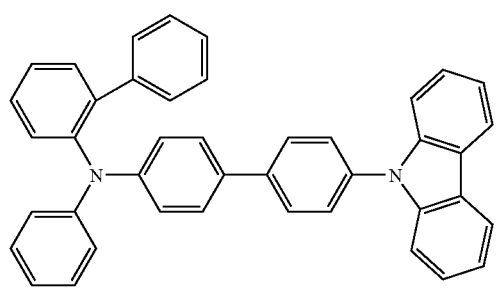
A-5
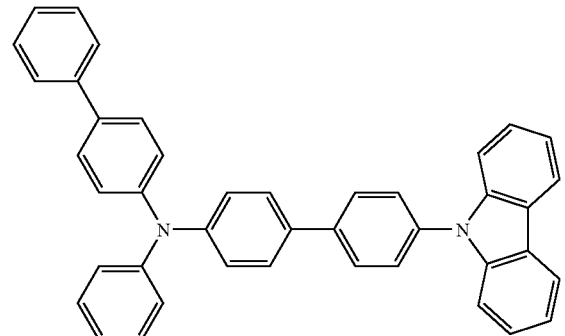
A-6
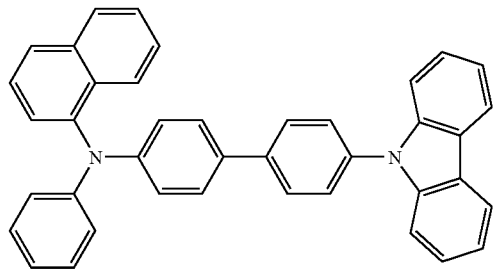
A-7
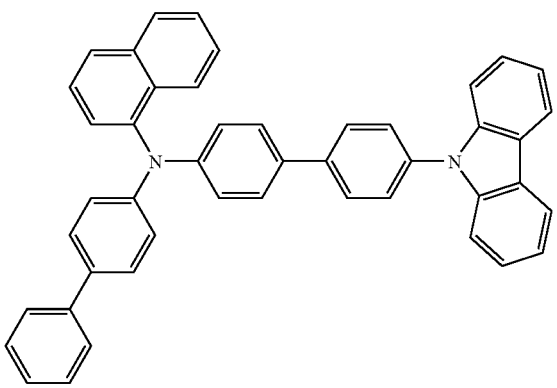
A-8
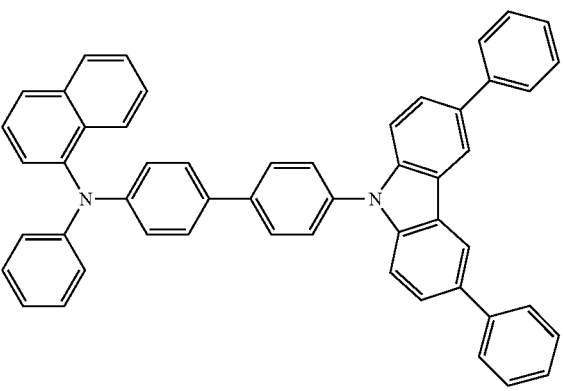

A-9
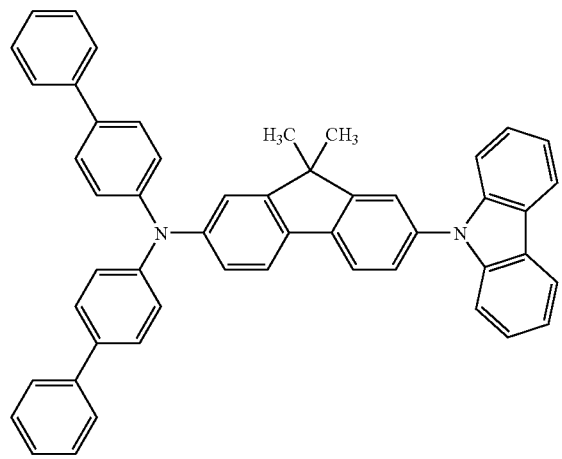
A-10
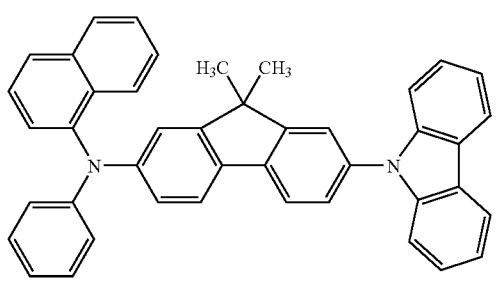
A-11
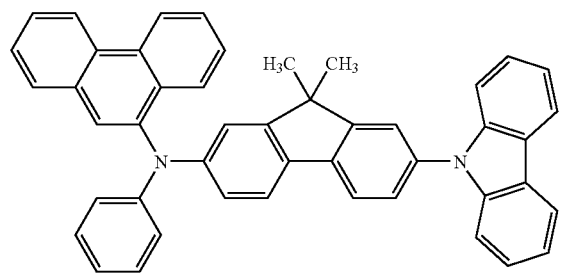
A-12
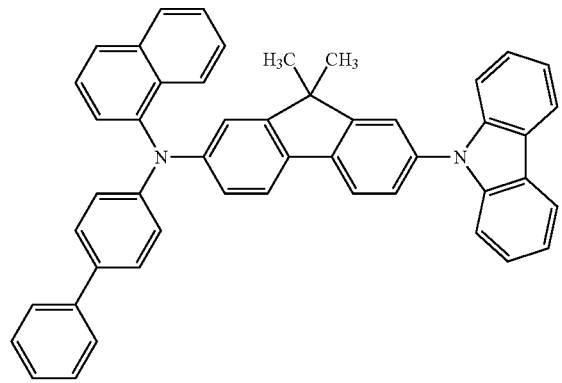
A-13
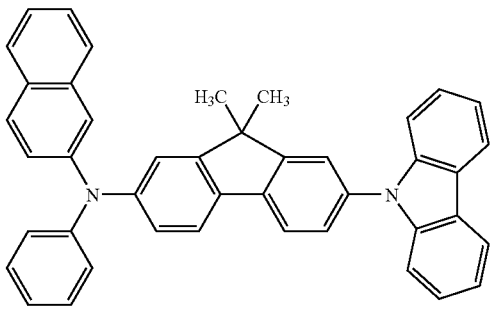
A-14
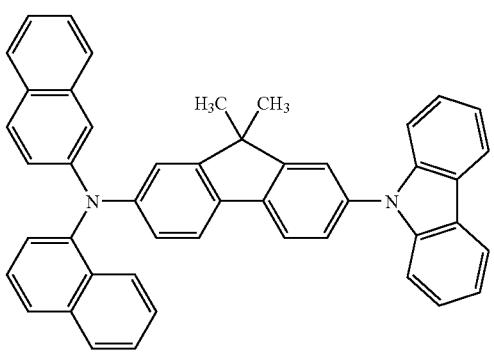
A-15
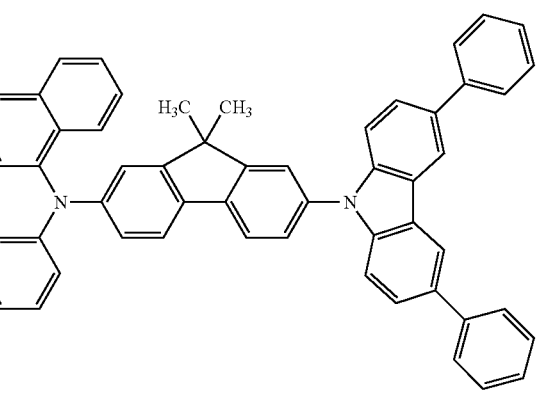
A-16
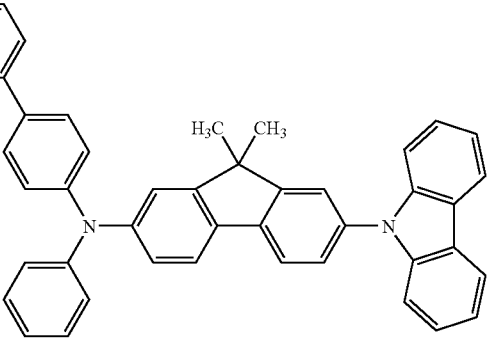

A-17
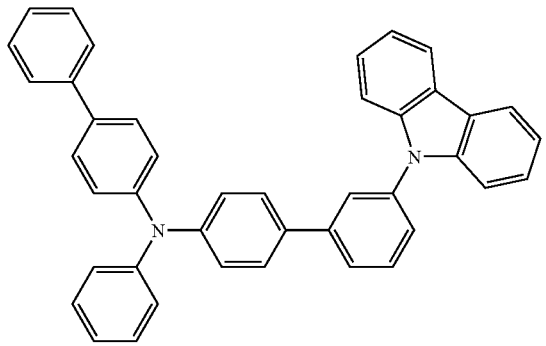
A-18
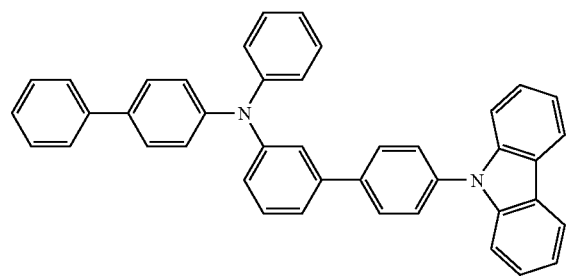
A-19
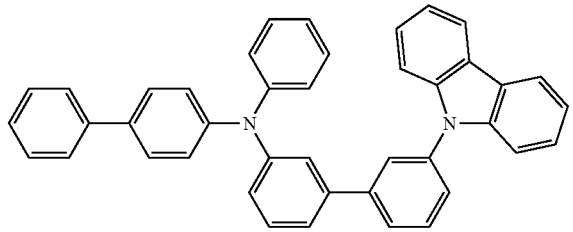
A-20
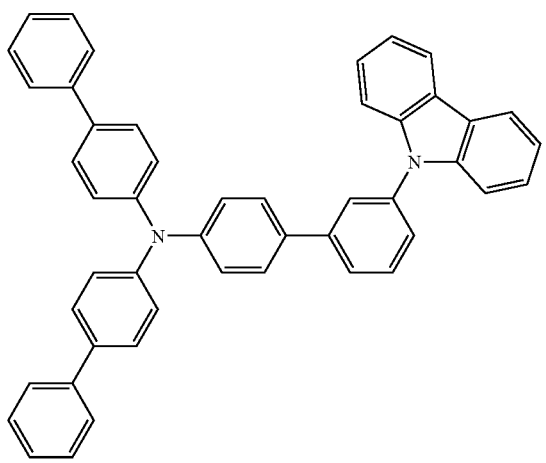
A-21
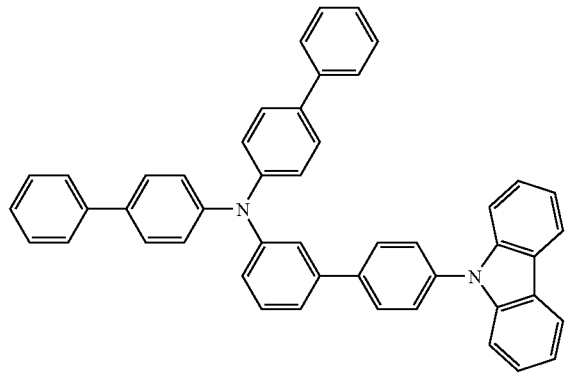
A-22
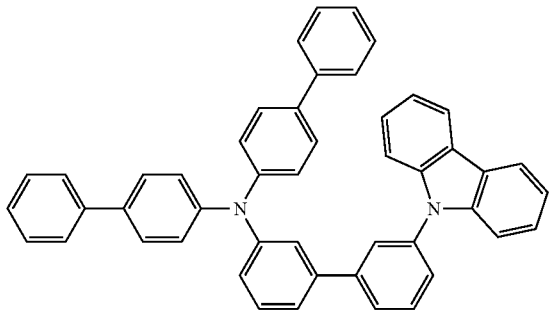
A-23
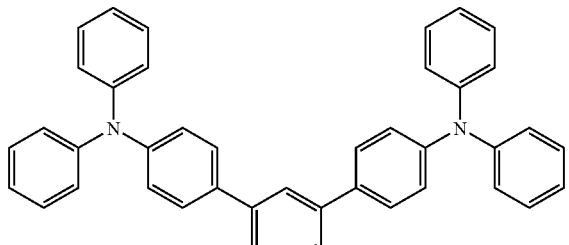
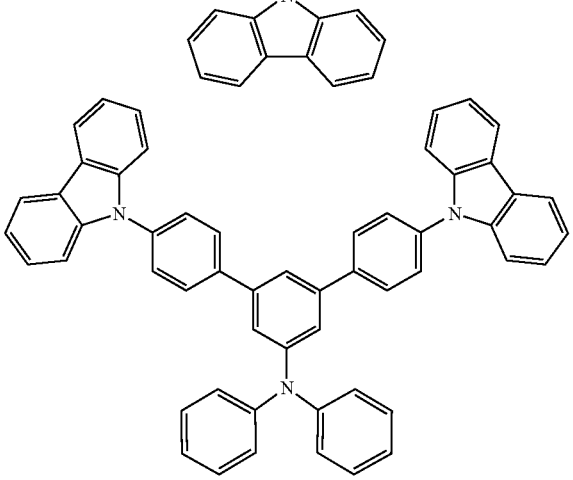

A-25
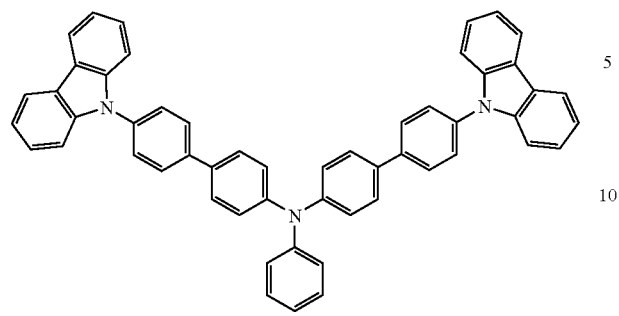
A-26
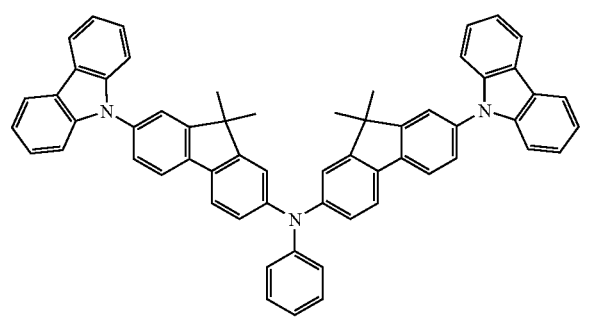
A-27
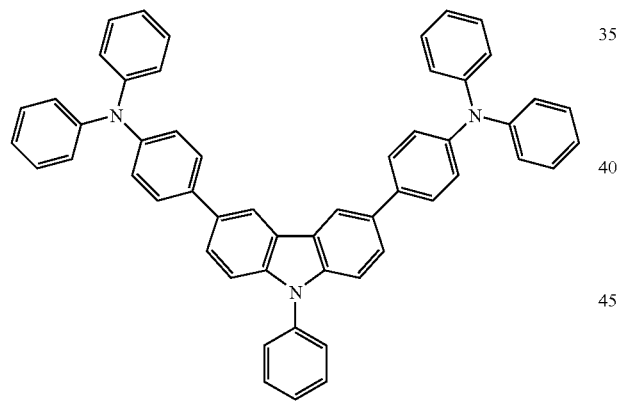
A-28
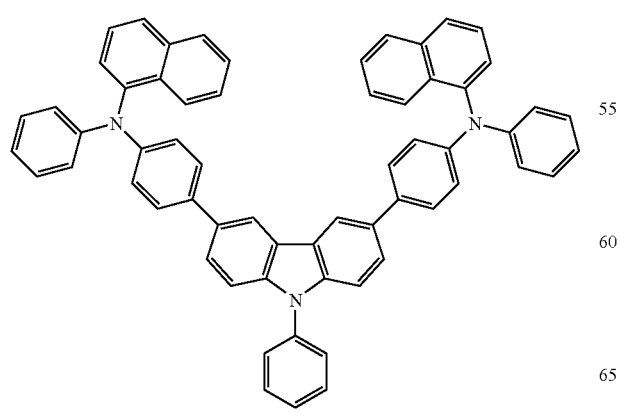
A-29
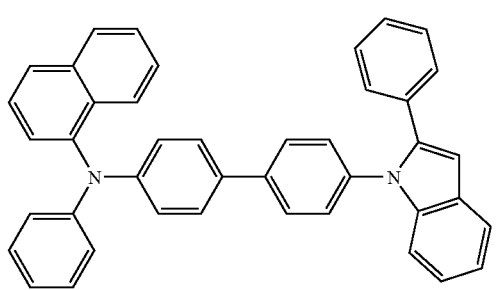
A-30
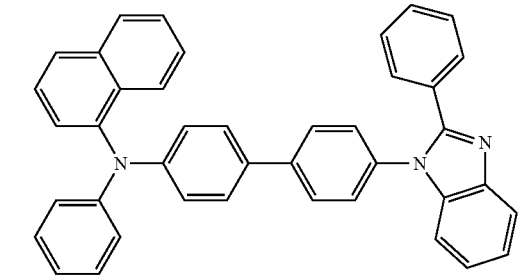
A-31
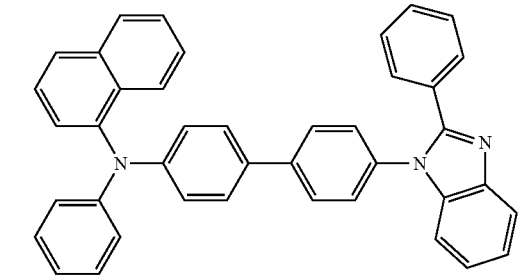
A-32
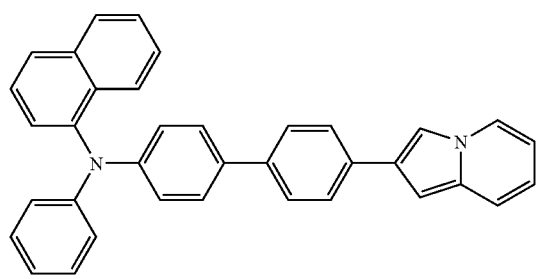
A-33
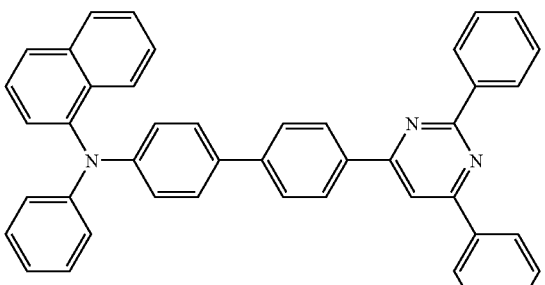

A-34
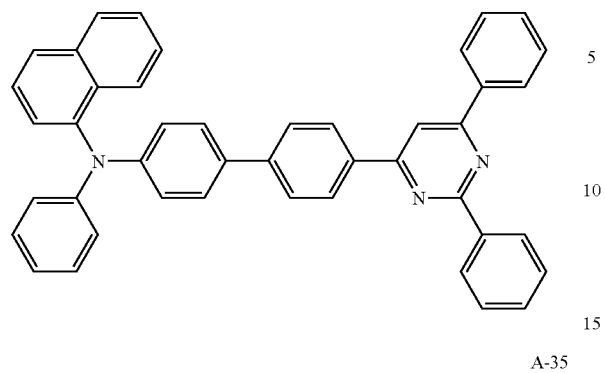
A-35
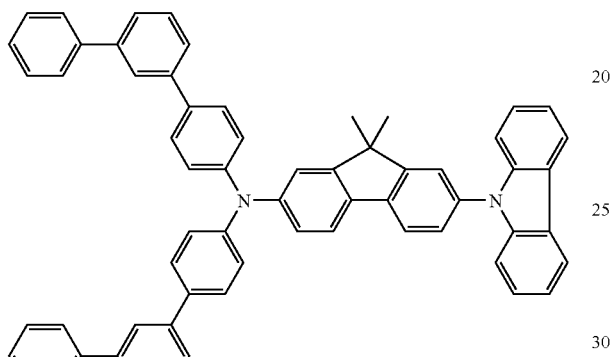
A-36
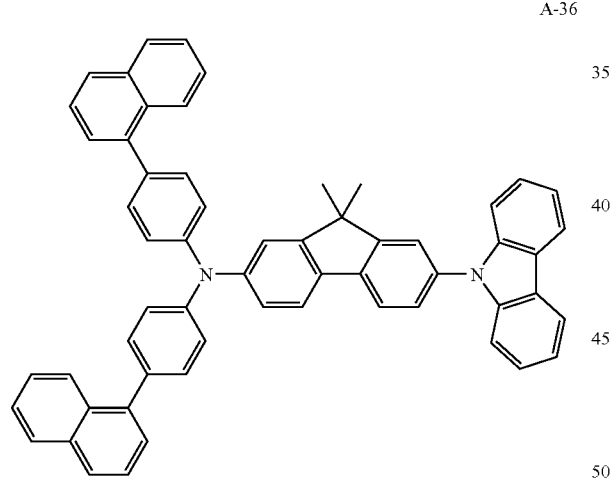
A-37
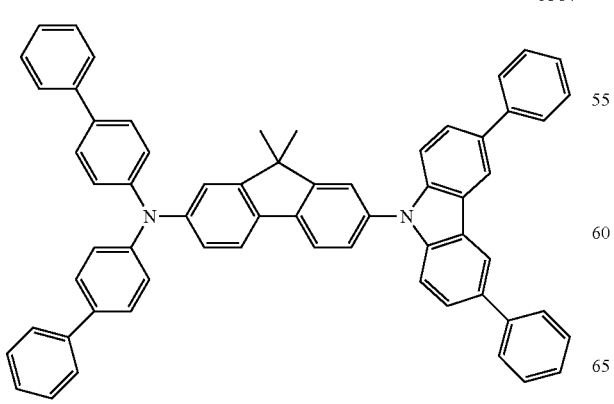
A-38
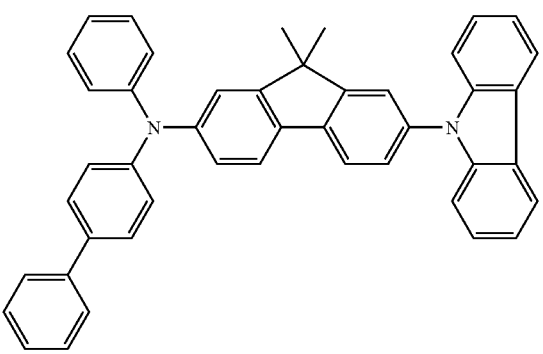
A-39
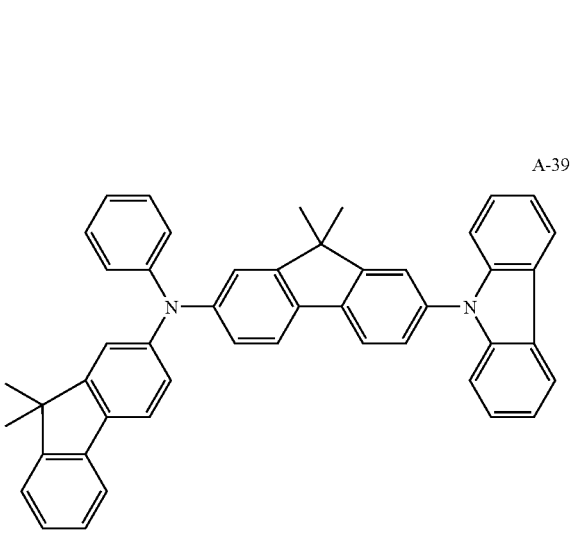
A-40
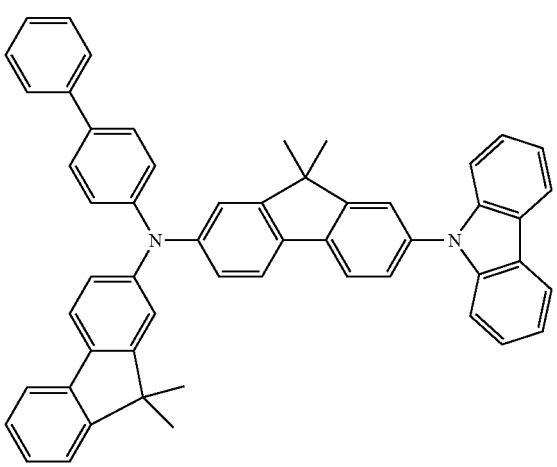

-continued
A-41
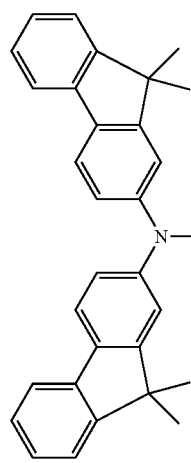
A-42
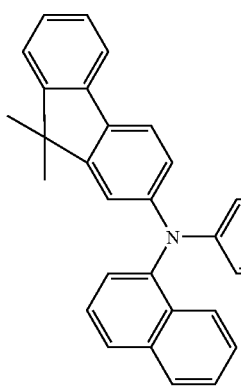
A-43
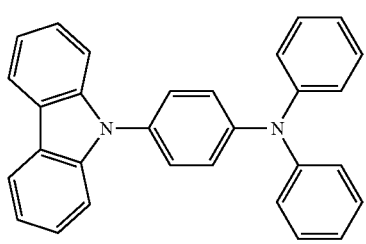
A-44
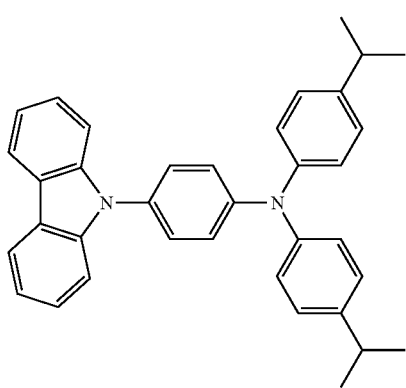
A-45
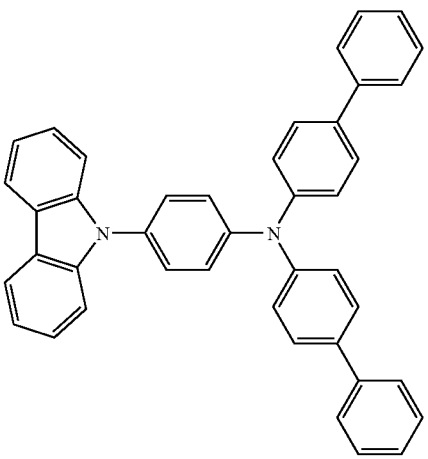
A-46
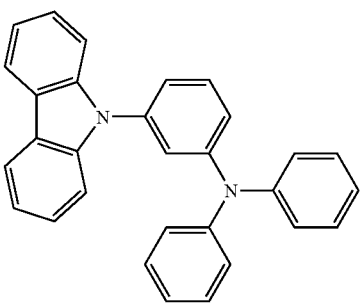
A-47
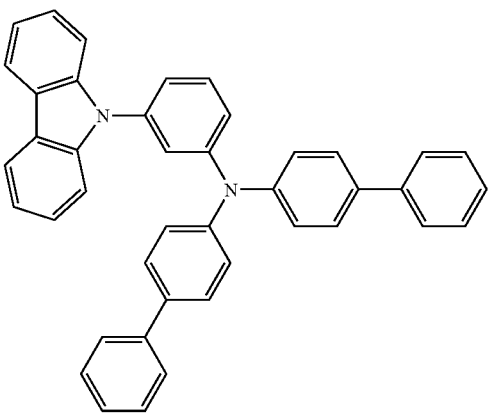
A-48
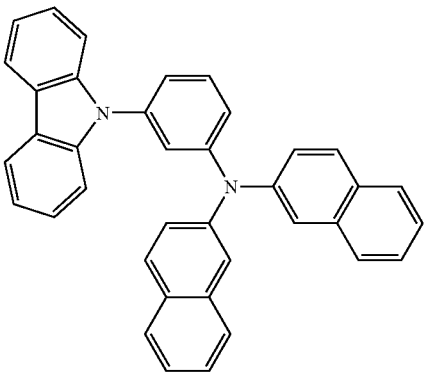

A-49
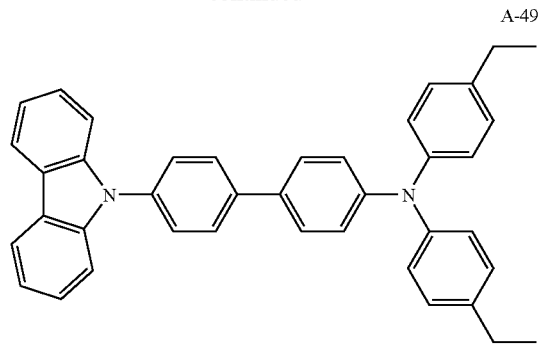
A-50
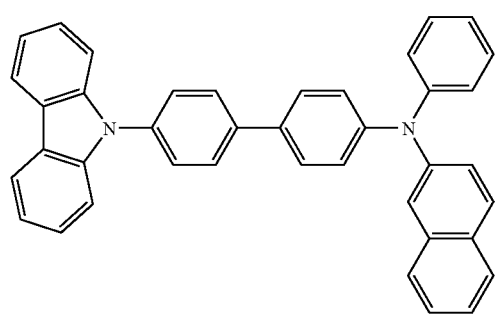
A-51
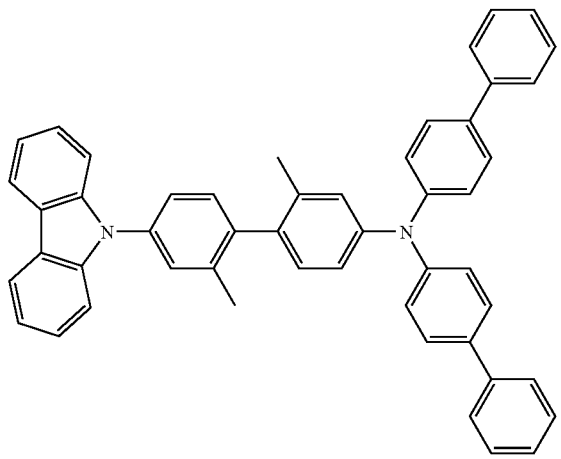
A-52
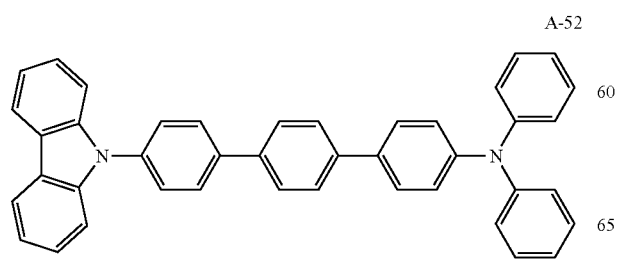
A-53
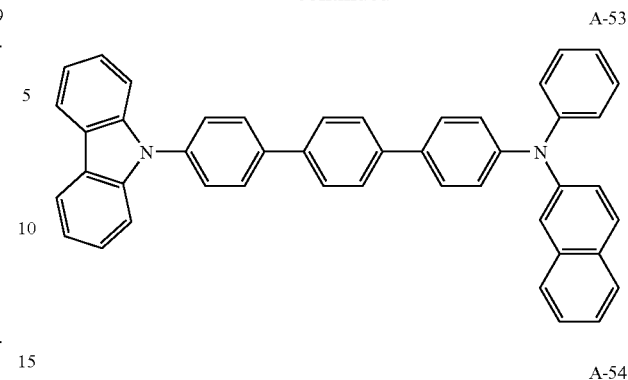
A-54
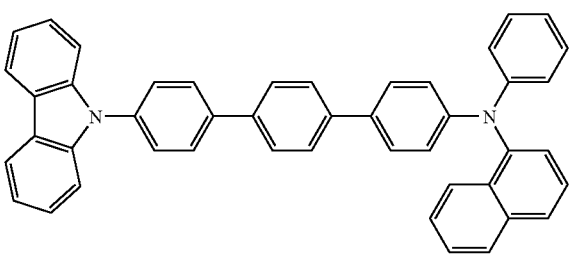
A-55
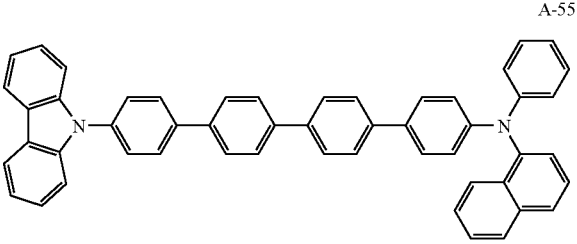
A-56
A-57
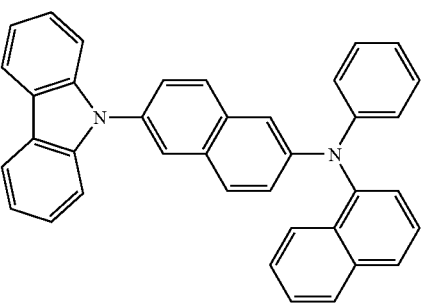

A-58
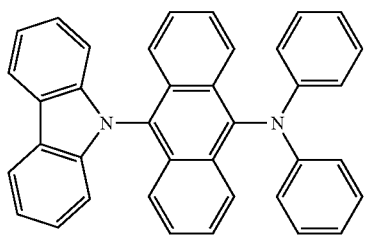

A-59
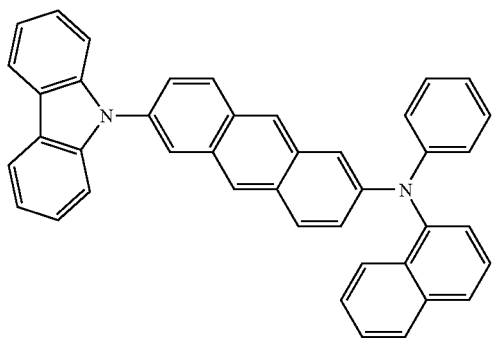

A-60
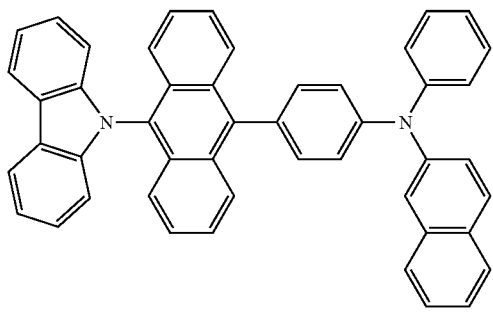

A-61
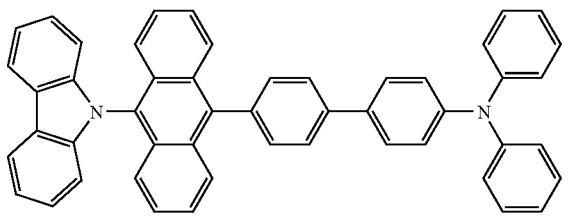

A-62
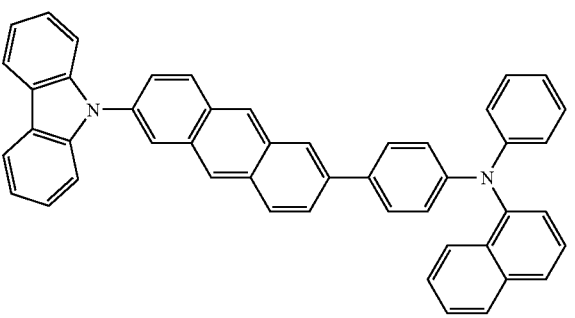

A-63
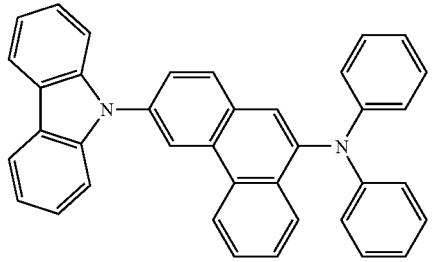

A-64
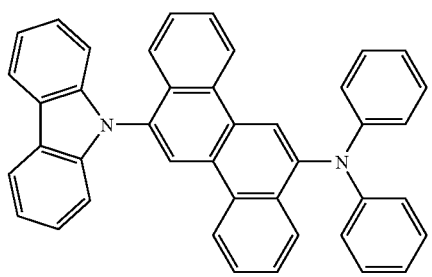

A-65
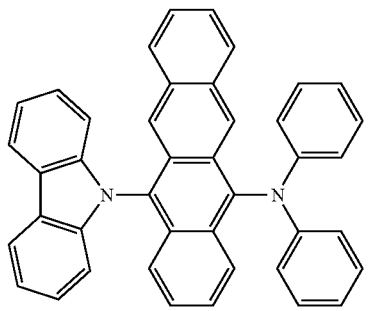

(C) The layer arranged in the electron injection and transport region (electron-transporting layer 50, electron-injecting layer 60) contains a benzimidazole derivative. The benzimidazole derivative is preferably a compound represented by the following formula (3) or (4):

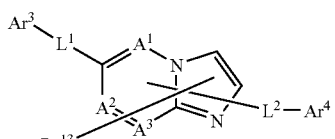 (3)

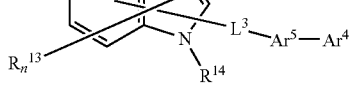 (4)

In the formula (3) or the formula (4), $A^1$ to $A^3$ are each independently a nitrogen atom or a carbon atom;

$Ar^3$ is a substituted or unsubstituted aryl group having 6 to 60 ring carbon atoms or a substituted or unsubstituted heteroaryl group having 3 to 60 ring carbon atoms; $Ar^4$ is a hydrogen atom, a substituted or unsubstituted aryl group having 6 to 60 ring carbon atoms, a substituted or unsubstituted heteroaryl group having 3 to 60 ring carbon atoms, a substituted or unsubstituted alkyl group having 1 to 20 carbon atoms, a substituted or unsubstituted alkoxy group having 1 to 20 carbon atoms, provided that one of $Ar^3$ and $Ar^4$ is a substituted or unsubstituted fused ring group having 10 to 60 ring carbon atoms or a substituted or unsubstituted monoheterofused ring group having 3 to 60 ring carbon atoms;

$Ar^5$ is a substituted or unsubstituted arylene group having 6 to 60 carbon atoms or a substituted or unsubstituted heteroarylene group having 3 to 60 carbon atoms;

$L^1$, $L^2$, and $L^3$ are independently a single bond, a substituted or unsubstituted arylene group having 6 to 60 ring carbon atoms, a substituted or unsubstituted heteroarylene group having 3 to 60 ring carbon atoms or a substituted or unsubstituted fluorenylene group;

$R^{13}$ is a hydrogen atom, a substituted or unsubstituted aryl group having 6 to 60 ring carbon atoms, a substituted or unsubstituted heteroaryl group having 3 to 60 ring carbon atoms, a substituted or unsubstituted alkyl group having 1 to 20 carbon atoms, or a substituted or unsubstituted alkoxy group having 1 to 20 carbon atoms, and n is an integer of 0 to 5, provided that, when n is 2 or more, a plurality of $R^{13}$s may be the same or different; adjacent $R^{13}$s may be bonded to form a carbocyclic aliphatic ring or a carbocyclic aromatic ring;

$R^{14}$ is a hydrogen atom, a substituted or unsubstituted aryl group having 6 to 60 ring carbon atoms, a substituted or unsubstituted heteroaryl group having 3 to 60 ring carbon atoms, a substituted or unsubstituted alkyl group having 1 to 20 carbon atoms, a substituted or unsubstituted alkoxy group having 1 to 20 carbon atoms or -$L^1$-$Ar^5$—$Ar^4$.

Now, the second embodiment of the invention will be explained.

The white light-emitting organic EL device according to the second embodiment of the invention has at least an emitting layer which is arranged between an anode and a cathode and comprises an organic compound. Further, one or more layers are provided in the hole-injection and transport region between the anode and the emitting layer, and one or more layers in the electron injection and transport region between the cathode and the emitting layer.

Figure 2:
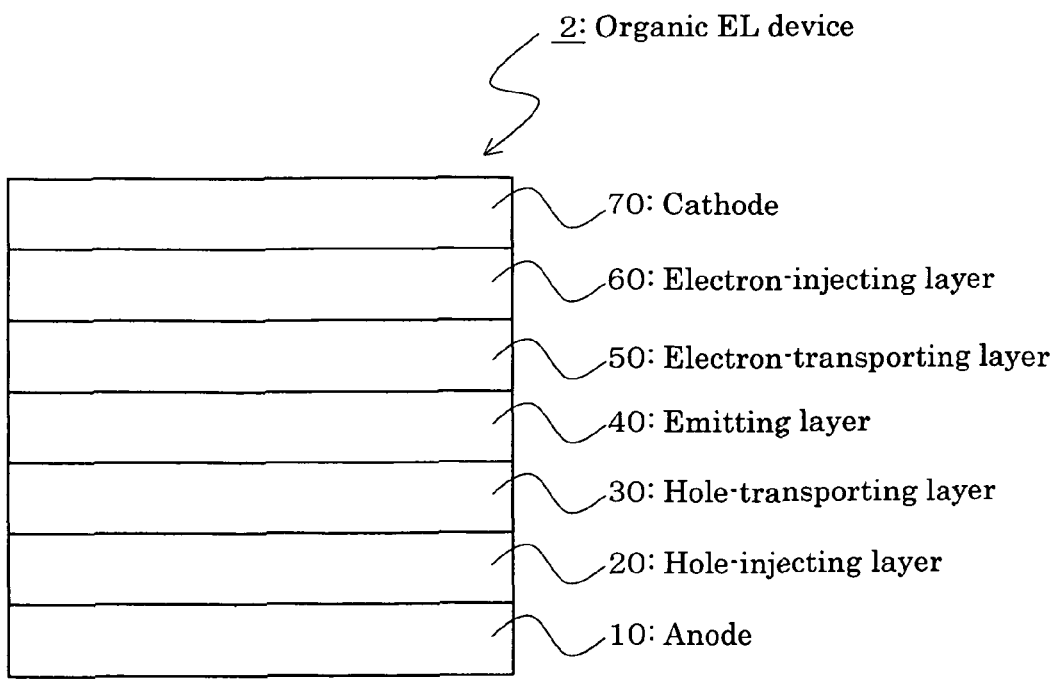
FIG. 2 is a schematic cross-sectional view of a white light-emitting organic EL device according to the second embodiment of the invention.

FIG. 2 is a schematic cross-sectional view showing one embodiment of the white light-emitting organic EL device of the second embodiment.

In the organic EL device 2, an anode 10, a hole-injecting layer 20, a hole-transporting layer 30, an emitting layer 40, an electron-transporting layer 50, an electron-injecting layer 60, and a cathode 70 are sequentially stacked on a substrate (not shown).

In the invention, the hole-transporting layer 30 which is arranged in the hole injection and transport region and in contact with the emitting layer, and the electron-transporting layer 50 and the electron-injecting layer 60 which are arranged in the electron injection and transport region satisfy the following conditions (A') and (B'):

(A') The layer which is arranged in the hole-injection and transport region and in contact with the emitting layer (hole-transporting layer 30) contains an aromatic amine derivative having a carbazole skeleton. By containing the aromatic amine derivative having a carbazole skeleton in the hole-transporting layer 30, driving voltage of the device does not increase and the device can have high luminous efficiency and long life time.

The aromatic amine derivative having a carbazole skeleton is preferably a compound represented by the following formula (1) or a compound represented by the following formula (2):

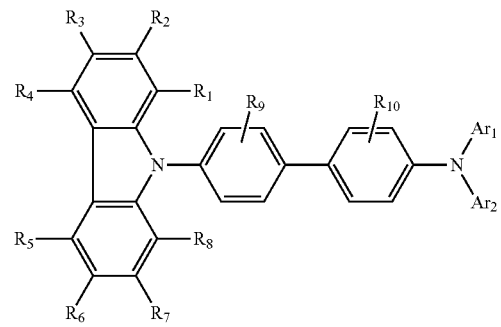

(1)

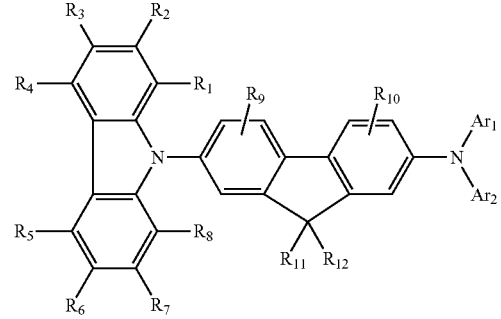

(2)

The compound represented by the above formula (1) and the compound represented by the above formula (2) are the same as the compound represented by the formula (1) and the compound represented by the formula (2) in the first embodiment of the invention.

(B') The layers arranged in the electron-injection and transport region (electron-transporting layer 50, electron-injecting layer 60) contain a benzimidazole derivative. The benzimidazole derivative is preferably a compound represented by the following formula (3) or (4):

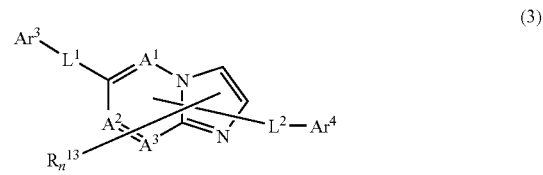

(3)

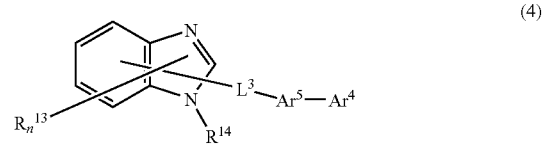

(4)

The compound represented by the above formula (3) and the compound represented by the above formula (4) are the same as the compound represented by the formula (3) and the compound represented by the formula (4) in the first embodiment of the invention.

In the white light-emitting organic EL device according to the second embodiment of the invention, one of the layers (hole-injecting layer 20) arranged in the hole-injection and transport region other than the layer in contact with the emitting layer preferably contains one or more materials selected from the group consisting of thiophene derivatives, 3 or more ring-fused aromatic derivatives, amine derivatives, conductive polymers, $CF_x$, CuPc, transition metal oxides, fullerenes and acceptor materials.

The materials of the above-mentioned thiophene derivatives and the like are the same as the materials for one of the layers arranged in the hole-injection and transport region other than the layer in contact with the emitting layer, in the first embodiment of the invention.

Representative constitutional examples used in the organic EL device according to the first embodiment and the second embodiment of the invention will be shown below. Of course, the invention is not limited to these constitutional examples.
(1) Anode/hole-injecting layer/hole-transporting layer/emitting layer/electron-transporting layer/cathode
(2) Anode/hole-injecting layer/hole-transporting layer/emitting layer/electron-transporting layer/cathode (FIGS. 1 and 2)
(3) Anode/hole-injecting layer/hole-transporting layer/emitting layer/electron-transporting layer/insulating layer/cathode
(4) Anode/insulating layer/hole-injecting layer/hole-transporting layer/emitting layer/electron-transporting layer/electron-injecting layer/insulating layer/cathode Light emitted from the emitting layer can be outcoupled from either the anode side or the cathode side, or both the sides.

The organic EL device may have a cavity structure between the anode and the cathode, namely, a structure wherein light emitted from the emitting layer is reflected between the anode and the cathode. For example, a structure in which the cathode is formed by using a semi-transmissive/semi-reflective material and the anode has a light reflective surface may be mentioned. In this case, light emission which is multiply interfered between the light reflective surface on the anode side and the light reflective surface on the cathode side is outcoupled from the cathode side. Optical length between the light reflective surface on the anode side and the light reflective surface on the cathode side is determined depending upon the wavelength of the light to be outcoupled, and film thicknesses of the layers are set so as to satisfy the optical length. In particular, in an organic EL device of top emission type (light emission is outcoupled from the device not through the supporting substrate), by positively using the cavity structure, it is possible to improve the outcoupling efficiency of the light emission and to control the light emission spectrum.

Respective parts constituting the organic EL devices according to the first embodiment and the second embodiment of the invention (hereinafter often referred to simply as "the organic EL device of the invention") will be explained below:
[Substrate]

The organic EL device of the invention is usually formed on a transparent substrate. The transparent substrate is a substrate for supporting the organic EL device, and is preferably a flat and smooth substrate having a 400-to-700-nm-visible-light transmittance of 50% or more.

Specific examples thereof include glass plates and polymer plates. Examples of the glass plate include soda-lime glass, barium/strontium-containing glass, lead glass, aluminosilicate glass, borosilicate glass, barium borosilicate glass, and quartz. Examples of the polymer plate include polycarbonate, acrylic polymer, polyethylene terephthalate, polyethersulfide, and polysulfone.

Here, in the top emission type device in which light is outcoupled from the opposite side of the substrate, the substrate is not necessary transparent.
(Anode)

The anode of the organic EL device plays a role for injecting holes into its hole-transporting layer or emitting layer. The anode effectively has a work function of 4.5 eV or more.

Specific examples of materials for the anode used in the invention include metals such as aluminum (Al), chromium (Cr), molybdenum (Mo), tungsten (W), copper (Cu), silver (Ag) and gold (Au), alloys thereof and oxides of the metals and the alloys, or alloys of tin oxide ($SnO_2$) and antimony (Sb), ITO (indium tin oxide), InZnO (indium zinc oxide), and alloys of zinc oxide (ZnO) and aluminum (Al). Further, oxides of these metals and the alloys are used singly or in a mixed state.

In the case where light emission from the emitting layer is outcoupled through the anode, the transmittance of the anode to the light emission is preferably more than 10%.

On the other hand, when light emitted from the emitting layer is outcoupled from the cathode, the anode is preferably a reflective electrode. In this case, the anode may have a structure in which a first layer excellent in light reflectivity and a second layer provided on the first layer, which has light transmittance and a large work function are stacked.

For example, the first layer is formed of an alloy composed of aluminum as the major component. Minor components may contain at least an element having a work function smaller than that of aluminum as the major component. Such a minor component is preferably a lanthanoid-series element. Although the work function of lanthanoid series elements is not large, by containing these elements, stability of the anode increases and the hole-injecting property of the anode is satisfied. Further, as the minor component, silicon (Si), copper (Cu), etc. may be contained in addition to the lanthanoid series element.

The content of the minor components in the aluminum alloy layer constituting the first layer is preferably about 10 wt % or less in total when the minor component is Nd, Ni, Ti or the like which stabilizes aluminum. By this, while the reflectance in the aluminum alloy layer is kept, the aluminum alloy layer can be stably maintained during the production process of the organic electroluminescence device as well as processing accuracy and chemical stability can be obtained. Further, conductivity of the anode and adhesiveness to the substrate can be improved.

As the second layer, a layer formed of at least one of an oxide of aluminum alloy, an oxide of molybdenum, an oxide of zirconium, an oxide of chromium and an oxide of tantalum can be exemplified. Here, for example, when the second layer is a layer of an aluminum alloy oxide (including a naturally oxidized film) containing a lanthanoid series element as the minor component, transmittance of an oxide of the lanthanoid series element is high, so that transmittance of the second layer containing it becomes good. Therefore, high reflectance at the surface of the first layer can be maintained. Further, the second layer may be a transparent conductive layer formed of ITO, IZO or the like. These conductive layers can improve the electron injecting property of the anode.

A conductive layer may be provided on the substrate side of the anode to improve adhesiveness between the anode and the substrate. The conductive layer includes transparent conductive layers formed of ITO, IZO or the like.

When a display constituted using an organic EL device is driven by the active matrix system, the anode is patterned for pixel by pixel and formed in the state of connecting with a thin film transistor for driving which is provided on the substrate. In this case, an insulating film is provided on the anode, and the surface of the anode for each pixel is exposed through the opening of the insulating film.

The anode can be formed by forming these electrode materials into a thin film by vapor deposition, sputtering or the like.

The sheet resistance of the anode is preferably several-hundred Ω/□ or less. The film thickness of the anode, which varies depending upon the material thereof, is usually selected from 10 nm to 1 μm, preferably from 10 to 200 nm.
(Emitting Layer)

The emitting layer of the organic EL device has the following functions (1), (2) and (3) in combination.
(1) Injection function: function of allowing injection of holes from the anode or hole-injecting/transporting layer and injection of electrons from the cathode or electron-injecting/transporting layer upon application of an electric field
(2) Transporting function: function of moving injected carriers (electrons and holes) due to the force of an electric field
(3) Emitting function: function of allowing electrons and holes to recombine therein to emit light Note that electrons and holes may be injected into the emitting layer with different degrees, or the transportation capabilities indicated by the mobility of holes and electrons may differ. It is preferable that the emitting layer move either electrons or holes.

As the method of forming the emitting layer, a known method such as deposition, spin coating, or an LB method may be applied. It is preferable that the emitting layer be a molecular deposition film.

Here, the molecular deposition film means the film formed by deposition of a material compound in a gas phase state, or the film formed by immobilization of a material compound in a solution state or a liquid phase state. The molecular deposition film is usually distinguished from a thin film (molecular accumulation film) formed using the LB method by the difference in aggregation structure or higher order structure or the difference in function due to the difference in structure.

The emitting layer may also be formed by dissolving a binder such as a resin and a material compound in a solvent to obtain a solution, and forming a thin film from the solution by spin coating or the like, as disclosed in JP-A-S57-51781.

As the material used for the emitting layer, a known long-lived luminescent material may be used. It is preferable to use a material of the general formula (1) as the luminescent material.

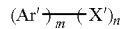
$(Ar'\!-\!)_m\!(X')_n$          (I)

In the formula, Ar' is an aromatic ring having 6 to 50 ring carbon atoms or a hetero-aromatic ring having 5 to 50 ring atoms.

Specific examples of the aromatic ring and hetero-aromatic ring include a phenyl ring, a naphthyl ring, an anthracene ring, a biphenylene ring, an azulene ring, an acenaphthylene ring, a fluorene ring, a phenanthrene ring, a fluoranthene ring, an acephenantnylene ring, a triphenylene ring, a pyrene ring, a chrysene ring, a benzanthracene ring, a naphthacene ring, a picene ring, a perylene ring, a pentaphene ring, a pentacene ring, a tetraphenylene ring, a hexaphene ring, a hexacene ring, a rubicene ring, a coronene ring, a trinaphthylene ring, a pyrrole ring, an indole ring, a carbazole ring, an imidazole ring, a benzimidazole ring, an oxadiazole ring, a triazole ring, a pyridine ring, a quinoxaline ring, a quinoline ring, a pyrimidine ring, a triazine ring, a thiophene ring, a benzothiophene ring, a thianthrene ring, a furan ring, a benzofuran ring, a pyrazole ring, a pyrazine ring, a pyridazine ring, an indolizine ring, a quinazoline ring, a phenanthroline ring, a silole ring, a benzosilole ring, and the like can be given.

Ar' is preferably a phenyl ring, a naphthyl ring, an anthracene ring, an acenaphthylene ring, a fluorene ring, a phenanthrene ring, a fluoranthene ring, a triphenylene ring, a pyrene ring, a chrysene ring, a benzanthracene ring, or a perylene ring.

X' is a substituent.

Specific examples of the substituent represented by X' include a substituted or unsubstituted aromatic group having 6 to 50 ring carbon atoms, a substituted or unsubstituted aromatic heterocyclic group having 5 to 50 ring atoms, a substituted or unsubstituted alkyl group having 1 to 50 carbon atoms, a substituted or unsubstituted alkoxy group having 1 to 50 carbon atoms, a substituted or unsubstituted aralkyl group having 1 to 50 carbon atoms, a substituted or unsubstituted aryloxy group having 5 to 50 ring atoms, a substituted or unsubstituted arylthio group having 5 to 50 ring atoms, a substituted or unsubstituted carboxyl group having 1 to 50 carbon atoms, a substituted or unsubstituted styryl group, a halogen group, a cyano group, a nitro group and a hydroxy group.

As examples of the substituted or unsubstituted aromatic group having 6 to 50 ring carbon atoms, a phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4''-t-butyl-p-terphenyl-4-yl group, 2-fluorenyl group, 9,9-dimethyl-2-fluorenyl group, 3-fluoranthenyl group and the like can be given.

The substituted or unsubstituted aromatic group having 6 to 50 ring carbon atoms is preferably a phenyl group, 1-naphthyl group, 2-naphthyl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, o-tolyl group, m-tolyl group, p-tolyl group, p-t-butylphenyl group, 2-fluorenyl group, 9,9-dimethyl-2-fluorenyl group, 3-fluoranthenyl group, or the like.

Examples of the substituted or unsubstituted aromatic heterocyclic groups having 5 to 50 ring atoms include 1-pyrrolyl, 2-pyrrolyl, 3-pyrrolyl, pyrazinyl, 2-pyridinyl, 3-pyridinyl, 4-pyridinyl, 1-indolyl, 2-indolyl, 3-indolyl, 4-indolyl, 5-indolyl, 6-indolyl, 7-indolyl, 1-isoindolyl, 2-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 9-carbazolyl, 1-phenanthrydinyl, 2-phenanthrydinyl, 3-phenanthrydinyl, 4-phenanthrydinyl, 6-phenanthrydinyl, 7-phenanthrydinyl, 8-phenanthrydinyl, 9-phenanthrydinyl, 10-phenanthrydinyl, 1-acrydinyl, 2-acrydinyl, 3-acrydinyl, 4-acrydinyl, 9-acrydinyl, 1,7-phenanthroline-2-yl, 1,7-phenanthroline-3-yl, 1,7-phenanthroline-4-yl, 1,7-phenanthroline-5-yl, 1,7-phenanthroline-6-yl, 1,7-phenanthroline-8-yl, 1,7-phenanthroline-9-yl, 1,7-phenanthroline- 10-yl, 1,8-phenanthroline-2-yl, 1,8-phenanthroline-3-yl, 1,8-phenanthroline-4-yl, 1,8-phenanthroline-5-yl, 1,8-phenanthroline-6-yl, 1,8-phenanthroline-7-yl, 1,8-phenanthroline-9-yl, 1,8-phenanthroline-10-yl, 1,9-phenanthroline-2-yl, 1,9-phenanthroline-3-yl, 1,9-phenanthroline-4-yl, 1,9-phenanthroline-5-yl, 1,9-phenanthroline-6-yl, 1,9-phenanthroline-7-yl, 1,9-phenanthroline-8-yl, 1,9-phenanthroline-10-yl, 1,10-phenanthroline-2-yl, 1,10-phenanthroline-3-yl, 1,10-phenanthroline-4-yl, 1,10-phenanthroline-5-yl, 2,9-phenanthroline-1-yl, 2,9-phenanthroline-3-yl, 2,9-phenanthroline-4-yl, 2,9-phenanthroline-5-yl, 2,9-phenanthroline-6-yl, 2,9-phenanthroline-7-yl, 2,9-phenanthroline-8-yl, 2,9-phenanthroline-10-yl, 2,8-phenanthroline-1-yl, 2,8-phenanthroline-3-yl, 2,8-phenanthroline-4-yl, 2,8-phenanthroline-5-yl, 2,8-phenanthroline-6-yl, 2,8-phenanthroline-7-yl, 2,8-phenanthroline-9-yl, 2,8-phenanthroline-10-yl, 2,7-phenanthroline-1-yl, 2,7-phenanthroline-3-yl, 2,7-phenanthroline-4-yl, 2,7-phenanthroline-5-yl, 2,7-phenanthroline-6-yl, 2,7-phenanthroline-8-yl, 2,7-phenanthroline-9-yl, 2,7-phenanthroline-10-yl, 1-phenazinyl, 2-phenazinyl, 1-phenothiazinyl, 2-phenothiazinyl, 3-phenothiazinyl, 4-phenothiazinyl, 10-phenothiazinyl, 1-phenoxazinyl, 2-phenoxazinyl, 3-phenoxazinyl, 4-phenoxazinyl, 10-phenoxazinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrole-1-yl, 2-methylpyrrole-3-yl, 2-methylpyrrole-4-yl, 2-methylpyrrole-5-yl, 3-methylpyrrole-1-yl, 3-methylpyrrole-2-yl, 3-methylpyrrole-4-yl, 3-methylpyrrole-5-yl, 2-t-butylpyrrole-4-yl, 3-(2-phenylpropyl)pyrrole-1-yl, 2-methyl-1-indolyl, 4-methyl-1-indolyl, 2-methyl-3-indolyl, 4-methyl-3-indolyl, 2-t-butyl-1-indolyl, 4-t-butyl-1-indolyl, 2-t-butyl-3-indolyl, and 4-t-butyl-3-indolyl groups.

Examples of the substituted or unsubstituted alkyl group having 1 to 50 carbon atoms include methyl, ethyl, propyl, isopropyl, n-butyl, s-butyl, isobutyl, t-butyl, n-pentyl, n-hexyl, n-heptyl, n-octyl, hydroxymethyl, 1-hydroxyethyl, 2-hydroxyethyl, 2-hydroxyisobutyl, 1,2-dihydroxyethyl, 1,3-dihydroxyisopropyl, 2,3-dihydroxy-t-butyl, 1,2,3-trihydroxypropyl, chloromethyl, 1-chloroethyl, 2-chloroethyl, 2-chloroisobutyl, 1,2-dichloroethyl, 1,3-dichloroisopropyl, 2,3-dichloro-t-butyl, 1,2,3-trichloropropyl, bromomethyl, 1-bromoethyl, 2-bromoethyl, 2-bromoisobutyl, 1,2-dibromoethyl, 1,3-dibromoisopropy, 2,3-dibromo-t-butyl, 1,2,3-tribromopropyl, iodomethyl, 1-iodoethyl, 2-iodoethyl, 2-iodoisobutyl, 1,2-diiodoethyl, 1,3-diiodoisopropyl, 2,3-diiodo-t-butyl, 1,2,3-triiodopropyl, aminomethyl, 1-aminoethyl, 2-aminoethyl, 2-aminoisobutyl, 1,2-diaminoethyl, 1,3-diaminoisopropyl, 2,3-diamino-t-butyl, 1,2,3-triaminopropyl, cyanomethyl, 1-cyanoethyl, 2-cyanoethyl, 2-cyanoisobutyl, 1,2-dicyanoethyl, 1,3-dicyanoisopropyl, 2,3-dicyano-t-butyl, 1,2,3-tricyanopropyl, nitromethyl, 1-nitroethyl, 2-nitroethyl, 2-nitroisobutyl, 1,2-dinitroethyl, 1,3-dinitroisopropyl, 2,3-dinitro-t-butyl, 1,2,3-trinitropropyl, cyclopropyl, cyclobutyl, cyclopentyl, cyclohexyl, 4-methylcylohexyl, 1-adamantyl, 2-adamantyl, 1-norbonyl and 2-norbornyl groups.

The substituted or unsubstituted alkoxy group having 1 to 50 carbon atoms is shown by —OY. Examples of Y include methyl, ethyl, propyl, isopropyl, n-butyl, s-butyl, isobutyl, t-butyl, n-pentyl, n-hexyl, n-heptyl, n-octyl, hydroxymethyl, 1-hydrpxyethyl, 2-hydroxyethyl, 2-hydroxyisobutyl, 1,2-dihydroxyethyl, 1,3-dihydroxyisopropyl, 2,3-dihydroxy-t-butyl, 1,2,3-trihydroxypropyl, chloromethyl, 1-chloroethyl, 2-chloroethyl, 2-chloroisobutyl, 1,2-dichloroethyl, 1,3-dichloroisopropyl, 2,3-dichloro-t-butyl, 1,2,3-trichloropropyl, bromomethyl, 1-bromoethyl, 2-bromoethyl, 2-bromoisobutyl, 1,2-dibromoethyl, 1,3-dibromoisopropyl, 2,3-dibromo-t-butyl, 1,2,3-tribromopropyl, iodomethyl, 1-iodoethyl, 2-iodoethyl, 2-iodoisobutyl, 1,2-diiodoethyl, 1,3-diiodoisopropyl, 2,3-diiodo-t-butyl, 1,2,3-triiodopropyl, aminomethyl, 1-aminoethyl, 2-aminoethyl, 2-aminoisobutyl, 1,2-diaminoethyl, 1,3-diaminoisopropyl, 2,3-diamino-t-butyl, 1,2,3-triaminopropyl, cyanomethyl, 1-cyanoethyl, 2-cyanoethyl, 2-cyanoisobutyl, 1,2-dicyanoethyl, 1,3-dicyanoisopropyl, 2,3-dicyano-t-butyl, 1,2,3-tricyanopropyl, nitromethyl, 1-nitroethyl, 2-nitroethyl, 2-nitroisobutyl, 1,2-dinitroethyl, 1,3-dinitroisopropyl group, 2,3-dinitro-t-butyl, and 1,2,3-trinitropropyl groups.

The substituted or unsubstituted aralkyl group having 1 to 50 carbon atoms include benzyl, 1-phenylethyl, 2-phenylethyl, 1-phenylisopropyl, 2-phenylisopropyl, phenyl-t-butyl, α-naphthyl, 1-α-naphthylethyl, 2-α-naphthylethyl, 1-α-naphthylisopropyl group, 2-α-naphthylisopropyl, β-naphthylmethyl, 1-β-naphthylethyl, 2-β-naphthylethyl, 1-β-naphthylisopropyl, 2-β-naphthylisopropyl, 1-pyrrolylmethyl, 2-(1-pyrrolyl)ethyl, p-methylbenzyl, m-methylbenzyl, o-methylbenzyl, p-chlorobenzyl, m-chlorobenzyl, o-chlorobenzyl, p-bromobenzyl, m-bromobenzyl, o-bromobenzyl, p-iodobenzyl, m-iodobenzyl, o-iodobenzyl, p-hydroxybenzyl, m-hydroxybenzyl, o-hydroxybenzyl, p-aminobenzyl, m-aminobenzyl, o-aminobenzyl, p-nitrobenzyl, m-nitrobenzyl, o-nitrobenzyl, p-cyanobenzyl, m-cyanobenzyl, o-cyanobenzyl, 1-hydroxy-2-phenylisopropyl and 1-chloro-2-phenylisopropyl groups.

The substituted or unsubstituted aryloxy group having 5 to 50 ring atoms is shown by —OY'. Examples of Y' include a phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4"-t-butyl-p-terphenyl-4-yl group, 2-pyrrolyl group, 3-pyrrolyl group, pyrazinyl group, 2-pyridinyl group, 3-pyridinyl group, 4-pyridinyl group, 2-indolyl group, 3-indolyl group, 4-indolyl group, 5-indolyl group, 6-indolyl group, 7-indolyl group, 1-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 2-quinolyl group, 3-quinolyl group, 4-quinolyl group, 5-quinolyl group, 6-quinolyl group, 7-quinolyl group; 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthrolin-2-yl group, 1,7-phenanthrolin-3-yl group, 1,7-phenanthrolin-4-yl group, 1,7-phenanthrolin-5-yl group, 1,7-phenanthrolin-6-yl group, 1,7-phenanthrolin-8-yl group, 1,7-phenanthrolin-9-yl group, 1,7-phenanthrolin-10-yl group, 1,8-phenanthrolin-2-yl group, 1,8-phenanthrolin-3-yl group, 1,8-phenanthrolin-4-yl group, 1,8-phenanthrolin-5-yl group, 1,8-phenanthrolin-6-yl group, 1,8-phenanthrolin-7-yl group, 1,8-phenanthrolin-9-yl group, 1,8-phenanthrolin-10-yl group, 1,9-phenanthrolin-2-yl group, 1,9-phenanthrolin-3-yl group, 1,9-phenanthrolin-4-yl group, 1,9-phenanthrolin-5-yl group, 1,9-phenanthrolin-6-yl group, 1,9-phenanthrolin-7-yl group, 1,9-phenanthrolin-8-yl group, 1,9-phenanthrolin-10-yl group, 1,10-phenanthrolin-2-yl group, 1,10-phenanthrolin-3-yl group, 1,10-phenanthrolin-4-yl group, 1,10-phenanthrolin-5-yl group, 2,9-phenanthrolin-1-yl group, 2,9-phenanthrolin-3-yl group, 2,9-phenanthrolin-4-yl group, 2,9-phenanthrolin-5-yl group, 2,9-phenanthrolin-6-yl group, 2,9-phenanthrolin-7-yl group, 2,9-phenanthrolin-8-yl group, 2,9-phenanthrolin-10-yl group, 2,8-phenanthrolin-1-yl group, 2,8-phenanthrolin-3-yl group, 2,8-phenanthrolin-4-yl group, 2,8-phenanthrolin-5-yl group, 2,8-phenanthrolin-6-yl group, 2,8-phenanthrolin-7-yl group, 2,8-phenanthrolin-9-yl group, 2,8-phenanthrolin-10-yl group, 2,7-phenanthrolin-1-yl group, 2,7-phenanthrolin-3-yl group, 2,7-phenanthrolin-4-yl group, 2,7-phenanthrolin-5-yl group, 2,7-phenanthrolin-6-yl group, 2,7-phenanthrolin-8-yl group, 2,7-phenanthrolin-9-yl group, 2,7-phenanthrolin-10-yl group, 1-phenazinyl group, 2-phenazinyl group, 1-phenothiadinyl group, 2-phenothiadinyl group, 3-phenothiadinyl group, 4-phenothiadinyl group, 1-phenoxadinyl group, 2-phenoxadinyl group, 3-phenoxadinyl group, 4-phenoxadinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrol-1-yl group, 2-methylpyrrol-3-yl group, 2-methylpyrrol-4-yl group, 2-methylpyrrol-5-yl group, 3-methylpyrrol-1-yl group, 3-methylpyrrol-2-yl group, 3-methylpyrrol-4-yl group, 3-methylpyrrol-5-yl group, 2-t-butylpyrrol-4-yl group, 3-(2-phenylpropyl)pyrrol-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group and 4-t-butyl-3-indolyl group.

The substituted or unsubstituted arylthio group having 5 to 50 ring atoms is shown by —SY″. Examples of Y″ include a phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4′-methylbiphenylyl group, 4″-t-butyl-p-terphenyl-4-yl group, 2-pyrrolyl group, 3-pyrrolyl group, pyrazinyl group, 2-pyridinyl group, 3-pyridinyl group, 4-pyridinyl group, 2-indolyl group, 3-indolyl group, 4-indolyl group, 5-indolyl group, 6-indolyl group, 7-indolyl group, 1-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthrolin-2-yl group, 1,7-phenanthrolin-3-yl group, 1,7-phenanthrolin-4-yl group, 1,7-phenanthrolin-5-yl group, 1,7-phenanthrolin-6-yl group, 1,7-phenanthrolin-8-yl group, 1,7-phenanthrolin-9-yl group, 1,7-phenanthrolin-10-yl group, 1,8-phenanthrolin-2-yl group, 1,8-phenanthrolin-3-yl group, 1,8-phenanthrolin-4-yl group, 1,8-phenanthrolin-5-yl group, 1,8-phenanthrolin-6-yl group, 1,8-phenanthrolin-7-yl group, 1,8-phenanthrolin-9-yl group, 1,8-phenanthrolin-10-yl group, 1,9-phenanthrolin-2-yl group, 1,9-phenanthrolin-3-yl group, 1,9-phenanthrolin-4-yl group, 1,9-phenanthrolin-5-yl group, 1,9-phenanthrolin-6-yl group, 1,9-phenanthrolin-7-yl group, 1,9-phenanthrolin-8-yl group, 1,9-phenanthrolin-10-yl group, 1,10-phenanthrolin-2-yl group, 1,10-phenanthrolin-3-yl group, 1,10-phenanthrolin-4-yl group, 1,10-phenanthrolin-5-yl group, 2,9-phenanthrolin-1-yl group, 2,9-phenanthrolin-3-yl group, 2,9-phenanthrolin-4-yl group, 2,9-phenanthrolin-5-yl group, 2,9-phenanthrolin-6-yl group, 2,9-phenanthrolin-7-yl group, 2,9-phenanthrolin-8-yl group, 2,9-phenanthrolin-10-yl group, 2,8-phenanthrolin-1-yl group, 2,8-phenanthrolin-3-yl group, 2,8-phenanthrolin-4-yl group, 2,8-phenanthrolin-5-yl group, 2,8-phenanthrolin-6-yl group, 2,8-phenanthrolin-7-yl group, 2,8-phenanthrolin-9-yl group, 2,8-phenanthrolin-10-yl group, 2,7-phenanthrolin-1-yl group, 2,7-phenanthrolin-3-yl group, 2,7-phenanthrolin-4-yl group, 2,7-phenanthrolin-5-yl group, 2,7-phenanthrolin-6-yl group, 2,7-phenanthrolin-8-yl group, 2,7-phenanthrolin-9-yl group, 2,7-phenanthrolin-10-yl group, 1-phenazinyl group, 2-phenazinyl group, 1-phenothiadinyl group, 2-phenothiadinyl group, 3-phenothiadinyl group, 4-phenothiadinyl group, 1-phenoxadinyl group, 2-phenoxadinyl group, 3-phenoxadinyl group, 4-phenoxadinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrol-1-yl group, 2-methylpyrrol-3-yl group, 2-methylpyrrol-4-yl group, 2-methylpyrrol-5-yl group, 3-methylpyrrol-1-yl group, 3-methylpyrrol-2-yl group, 3-methylpyrrol-4-yl group, 3-methylpyrrol-5-yl group, 2-t-butylpyrrol-4-yl group, 3-(2-phenylpropyl)pyrrol-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, and 4-t-butyl-3-indolyl group.

The substituted or unsubstituted carboxyl group having 1 to 50 carbon atoms is shown by —COOZ′. Examples of Z′ include methyl, ethyl, propyl, isopropyl, n-butyl, s-butyl, isobutyl, t-butyl, n-pentyl, n-hexyl, n-heptyl, n-octyl, hydroxymethyl, 1-hydroxyethyl, 2-hydroxyethyl, 2-hydroxyisobutyl, 1,2-dihydroxyethyl, 1,3-dihydroxyisopropyl, 2,3-dihydroxy-t-butyl, 1,2,3-trihydroxypropyl, chloromethyl, 1-chloroethyl, 2-chloroethyl, 2-chloroisobutyl, 1,2-dichloroethyl, 1,3-dicycloisopropyl, 2,3-dichloro-t-butyl, 1,2,3-trichloropropyl, bromomethyl, 1-bromoethyl, 2-bromoethyl, 2-bromoisobutyl, 1,2-dibromoethyl, 1,3-dibromoisopropyl, 2,3-dibromo-t-butyl, 1,2,3-tribromopropyl, iodomethyl, 1-iodoethyl, 2-iodoethyl, 2-iodoisobutyl, 1,2-diiodoethyl, 1,3-diiodoisopropyl, 2,3-diiodo-t-butyl, 1,2,3-triiodopropyl, aminomethyl, 1-aminoethyl, 2-aminoethyl, 2-aminoisobutyl, 1,2-diaminoethyl, 1,3-diamimnoisopropyl, 2,3-diamino-t-butyl, 1,2,3-triaminopropyl, cyanomethyl, 1-cyanoethyl, 2-cyanoethyl, 2-cyanoisobutyl, 1,2-dicyanoethyl group, 1,3-dicyanoisopropyl, 2,3-dicyano-t-butyl, 1,2,3-tricyanopropyl, nitromethyl, 1-nitroethyl, 2-nitroethyl, 2-nitroisobutyl, 1,2-dinitroethyl, 1,3-dinitroisopropyl, 2,3-dinitro-t-butyl and 1,2,3-trinitropropyl groups.

As examples of the substituted or unsubstituted styryl group, a 2-phenyl-1-vinyl group, 2,2-diphenyl-1-vinyl group, 1,2,2-triphenyl-1-vinyl group, and the like can be given.

As examples of the halogen group, fluorine, chlorine, bromine, iodine, and the like can be given.

m is an integer of 1 to 5, and n is an integer of 0 to 6.

m is preferably 1 to 2, and n is preferably 0 to 4.

Here, when m≥2, plural Ar's in parentheses may be the same or different.

Also, when n≥2, plural X's in parentheses may be the same or different.

As the material used in the emitting layer, it is further preferable to use an anthracene derivative represented by the following formula (II).

$$A1-L-A2 \tag{II}$$

wherein A1 and A2 are independently a substituted or unsubstituted monophenylanthryl group or a substituted or unsubstituted diphenylanthryl group, and may be the same or different; and L is a single bond or a divalent linking group.

In addition to the anthracene derivative described above, an anthracene derivative represented by the formula (III) can be given.

$$A3-An-A4 \tag{III}$$

wherein An is a substituted or unsubstituted divalent anthracene residue; and A3 and A4 are independently a substituted or unsubstituted monovalent fused aromatic ring group or a substituted or unsubstituted non-fused ring aryl group having 12 or more carbon atoms and may be the same or different.

As the anthracene derivative represented by the formula (II), an anthracene derivative represented by the following formula (II-a):

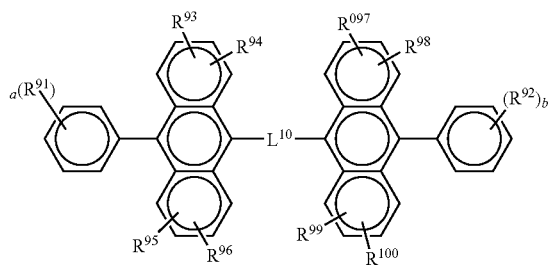

(II-a)

wherein $R^{91}$ to $R^{100}$ are independently a hydrogen atom, an alkyl group, a cycloalkyl group, an aryl group which may be substituted, an alkoxy group, an aryloxy group, an alkylamino group, an arylamino group or a heterocyclic group which may be substituted; a and b are each an integer of 1 to 5; when they are 2 or more, $R^{91}$s or $R^{92}$s may be the same or different, or $R^{91}$s or $R^{92}$s may be bonded together to form a ring; $R^{93}$ and $R^{94}$, $R^{95}$ and $R^{96}$, $R^{97}$ and $R^{98}$, or $R^{99}$ and $R^{100}$ may be bonded together to form a ring; and $L^{10}$ is a single bond, —O—, —S—, —N(R)— (R is an alkyl group or an aryl group which may be substituted), or an arylene group, and an anthracene derivative represented by the following formula (II-b):

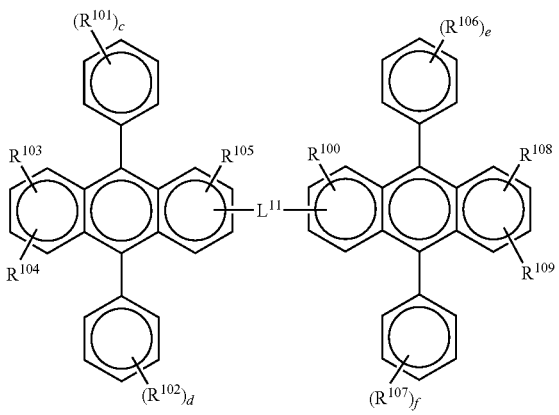

(II-b)

wherein $R^{101}$ to $R^{110}$ are independently a hydrogen atom, an alkyl group, a cycloalkyl group, a substituted or unsubstituted aryl group, an alkoxy group, an aryloxy group, an alkylamino group, an arylamino group or a substituted or unsubstituted heterocyclic group; c, d, e and f are each an integer of 1 to 5; when they are 2 or more, $R^{100}$s, $R^{102}$s, $R^{106}$s or $R^{107}$s may be the same or different, $R^{101}$s, $R^{102}$s, $R^{106}$s or $R^{107}$s may be bonded together to form a ring, or $R^{103}$ and $R^{104}$, or $R^{108}$ and $R^{109}$ may be bonded together to form a ring; and $L^{11}$ is a single bond, —O—, —S—, —N(R)— (R is an alkyl group or an aryl group which may be substituted), or an arylene group are preferably mentioned.

As for $R^{91}$ to $R^{110}$ shown in the above formulas (II-a) and (II-b), as the alkyl group, an alkyl group having 1 to 6 carbon atoms, as the cycloalkyl group, a cycloalkyl group having 3 to 6 carbon atoms, as the aryl group, an aryl group having 5 to 18 carbon atoms, as the alkoxyl group, an alkoxyl group having 1 to 6 carbon atoms, as the aryloxy group, an aryloxy group having 5 to 18 carbon atoms, as the arylamino group, an amino group substituted with an aryl group having 5 to 16' carbon atoms, as the heterocyclic group, triazole, oxadiazole, quinoxaline, furanyl, thienyl or the like can preferably be given.

As the alkyl group and the aryl group shown by R in —N(R)— in $L^{10}$ and $L^{11}$, an alkyl group having 1 to 6 carbon atoms and an aryl group having 5 to 18 carbon atoms are preferable.

As the host material for use with the dopants described below in the emitting layer, the compounds represented by the following formulas (i) to (ix) are preferred.

Asymmetrical anthracene represented by the following formula (1):

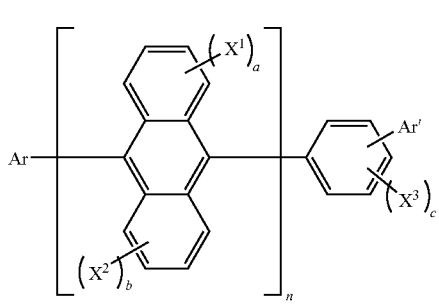

wherein Ar is a substituted or unsubstituted fused aromatic group having 10 to 50 ring carbon atoms, Ar' is a substituted or unsubstituted aromatic group having 6 to 50 ring carbon atoms, $X^1$, $X^2$ and $X^3$ are independently a substituted or unsubstituted aromatic group having 6 to 50 ring carbon atoms, a substituted or unsubstituted aromatic heterocyclic group having 5 to 50 ring atoms, a substituted or unsubstituted alkyl group having 1 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a carboxyl group, a halogen atom, a cyano group, a nitro group or a hydroxy group. a, b and c are each an integer of 0 to 4. n is an integer of 1 to 3. When n is two or more, the groups in [ ] may be the same or different.

Asymmetrical monoanthracene derivatives represented by the following formula (ii):

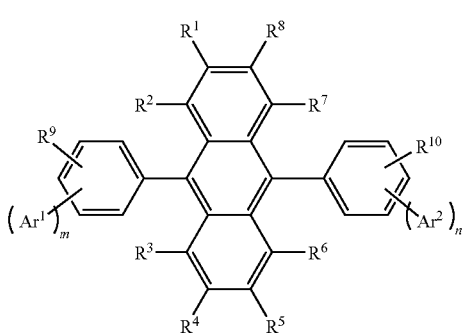

wherein $Ar^1$ and $Ar^2$ are independently a substituted or unsubstituted aromatic ring group having 6 to 50 ring carbon atoms, and m and n are each an integer of 1 to 4, provided that in the case where m=n=1 and $Ar^1$ and $Ar^2$ are symmetrically bonded to the benzene rings, $Ar^1$ and $Ar^2$ are not the same, and in the case where m or n is an integer of 2 to 4, m is different from n.

$R^1$ to $R^{10}$ are independently a hydrogen atom, a substituted or unsubstituted aromatic ring group having 6 to 50 ring carbon atoms, a substituted or unsubstituted aromatic heterocyclic group having 5 to 50 ring atoms, a substituted or unsubstituted alkyl group having 1 to 50 carbon atoms, a substituted or unsubstituted cycloalkyl group, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a substituted or unsubstituted silyl group, a carboxyl group, a halogen atom, a cyano group, a nitro group or a hydroxy group.

Asymmetrical pyrene derivatives represented by the following formula (iii):

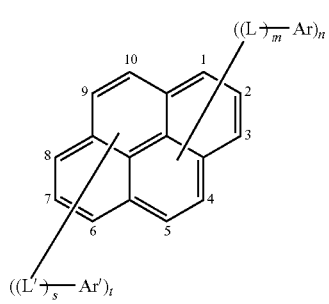

wherein Ar and Ar' are independently a substituted or unsubstituted aromatic group having 6 to 50 ring carbon atoms; L and L' are independently a substituted or unsubstituted phenylene group, a substituted or unsubstituted naphthalenylene group, a substituted or unsubstituted fluorenylene group, or a substituted or unsubstituted dibenzosilolylene group;

m is an integer of 0 to 2, n is an integer of 1 to 4, s is an integer of 0 to 2, and t is an integer of 0 to 4;

L or Ar bonds at any one position of 1 to 5 of the pyrene, and L' or Ar' bonds at any one position of 6 to 10 of the pyrene; provided that when n+t is an even number, Ar, Ar', L and L' satisfy the following (1) or (2):

(1) Ar≠Ar' and/or L≠L' where ≠ means these substituents are groups having different structures from each other.

(2) when Ar=Ar' and L=L',
 (2-1) m≠s and/or n≠t, or
 (2-2) when m=s and n=t,
  (2-2-1) L and L', or the pyrene each bond to Ar and Ar' at different positions, or (2-2-2) when L and L' or pyrene are bonded to the same position of Ar and Ar', the positions of the substitution of L and L' or Ar and Ar' at pyrene are neither the $1^{st}$ position and the $6^{th}$ position, nor the $2^{nd}$ position and the $7^{th}$ position.

Asymmetrical anthracene represented by the following formula (iv):

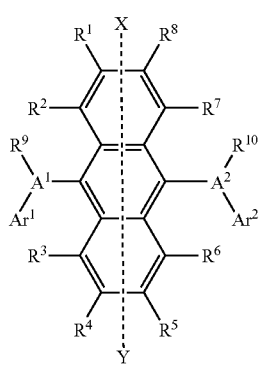

wherein $A^1$ and $A^2$ are independently a substituted or unsubstituted fused aromatic ring group having 10 to 20 ring carbon atoms, $Ar^1$ and $Ar^2$ are independently a hydrogen atom or a substituted or unsubstituted aromatic ring group having 6 to 50 ring carbon atoms.

$R^1$ to $R^{10}$ are independently a hydrogen atom, a substituted or unsubstituted aromatic ring group having 6 to 50 ring carbon atoms, a substituted or unsubstituted aromatic heterocyclic group having 5 to 50 ring atoms, a substituted or unsubstituted alkyl group having 1 to 50 carbon atoms, a substituted or unsubstituted cycloalkyl group, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a substituted or unsubstituted silyl group, a carboxyl group, a halogen atom, a cyano group, a nitro group or a hydroxy group.

Each of $Ar^1$, $Ar^2$, $R^9$ and $R^{10}$ may be plural, and adjacent groups thereof may form a saturated or unsaturated ring structure, provided that groups do not symmetrically bond to 9th and 10th positions of the central anthracene with respect to X-Y axis.

The emission performance of the emitting layer can be improved by adding a small amount of a fluorescent compound as a dopant therein. Dopants known as a dopant material having a long lifetime may be used. It is preferable to use, as the dopant material of the luminescent material, a material represented by the formula (IV):

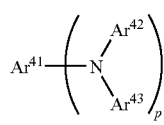

(IV)

wherein $Ar^{41}$ to $Ar^{43}$ are independently a substituted or unsubstituted aromatic group with 6 to 50 ring carbon atoms, or a substituted or unsubstituted styryl group.

As examples of the substituted or unsubstituted aromatic group having 6 to 50 ring carbon atoms, a phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4''-t-butyl-p-terphenyl-4-yl group, 2-fluorenyl group, 9,9-dimethyl-2-fluorenyl group, 3-fluoranthenyl group, and the like can be given.

The substituted or unsubstituted aromatic group having 6 to 50 ring carbon atoms is preferably a phenyl group, 1-naphthyl group, 2-naphthyl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, o-tolyl group, m-tolyl group, p-tolyl group, p-t-butylphenyl group, 2-fluorenyl group, 9,9-dimethyl-2-fluorenyl group, 3-fluoranthenyl group, or the like.

As examples of the substituted or unsubstituted styryl group, 2-phenyl-1-vinyl group, 2,2-diphenyl-1-vinyl group, 1,2,2-triphenyl-1-vinyl group, and the like can be given.

p is an integer of 1 to 4.

Here, when p≥2, plural $Ar^{42}$s and $Ar^{43}$s in parentheses may be independently the same or different.

In the second embodiment of the invention, the emitting layer 40 is formed as a stacked body by stacking layers made of different emitting materials or as a mixture layer by mixing plural emitting materials so that white light emission can be obtained.

For example, the emitting layer 40 is formed as a stacked body with a first emitting layer, a second emitting layer and a third emitting layer, and the first emitting layer is made to be a red light emitting layer, the second emitting layer to be a blue light emitting layer and the third emitting layer to be a green light emitting layer, thereby white light emission excellent in color rendering properties can be obtained. Light emission balance between the three emitting layer in the device can be easily controlled by further providing an electron barrier layer.

Representative structure of the emitting layer will be shown below:

First emitting layer/second emitting layer

First emitting layer/electron barrier layer/second emitting layer

First emitting layer/second emitting layer/third emitting layer

First emitting layer/electron barrier layer/second emitting layer/third emitting layer First emitting layer/electron barrier layer/second emitting layer/electron barrier layer/third emitting layer First emitting layer/second emitting layer/electron barrier layer/third emitting layer As the host material for the green light emitting layer, fused aromatic ring derivatives can be used, for example.

As the fused aromatic ring derivatives, anthracene derivatives, naphthacene derivatives, pyrene derivatives, pentacene derivatives, etc. are preferable in view of luminous efficiency and emission life time.

In view of luminous efficiency, etc., the host material for the green, light emitting layer is preferably a diarylanthracene derivative, a triarylanthracene derivative or a tetraarylanthracene derivative, more preferably a naphthylanthracene derivative, and particularly preferably a naphthylanthracene derivative having a polyphenyl group as a substituent.

Here, the polyphenyl group is a substituent constituted from a biphenyl, terphenyl, quarterphenyl, quaterphenyl or quinquephenyl which may be substituted.

The dopant material for the green light emitting layer is not limited but aromatic amine derivatives are preferable in view of luminous efficiency, etc.

As the aromatic amine derivatives, fused aromatic ring derivatives having an arylamino group which may be substituted. Such compounds include pyrene, anthracene and chrysene which have an arylamino group. Particularly preferred is a pyrene compound having an arylamino group.

The dopant material for the green light emitting layer is preferably a styrylamine compound.

The styrylamine compound includes styrylamine, styryl diamine, styryl triamine and styryl tetraamine.

Here, the styrylamine is a compound in which at least one arylvinyl group is substituted to the arylamine which may be substituted. The arylvinyl group may be substituted, and such a substituent includes an aryl group, a silyl group, an alkyl group, a cycloalkyl group and an arylamino group. These substituents may further have a substituent.

The host material for the red light emitting layer includes naphthacene derivatives.

The dopant material for the red light emitting layer includes periflanthene derivatives and pyromethene derivatives.

(Electron-Injecting/Transporting Layer)

The hole-injecting/transporting layer is a layer for helping the injection of holes into the emitting layer to transport the holes to a light emitting region. The hole mobility thereof is large and the ionization energy thereof is usually as small as 5.6 eV or less. Such a hole-injecting/transporting layer is preferably made of a material which can transport holes to the emitting layer at a lower electric field intensity. The hole mobility thereof is preferably at least $10^{-4}$ cm$^2$/V-second when an electric field of, e.g., $10^4$ to $10^6$ V/cm is applied.

In the invention, the hole-injecting layer and the hole-transporting layer may be plural layers, respectively. The hole-transporting layer may be formed singularly of the compound represented by the formula (1) or (2) used in the device structures in the invention, or may be formed of a mixture thereof with other materials.

Any materials which have the above preferable properties can be used as the material for forming the hole-injecting/transporting layer without particular limitation. The material for forming the hole-injecting/transporting layer can be arbitrarily selected from materials which have been widely used as a material transporting carriers of holes in photoconductive materials and known materials used in a hole-injecting layer of organic EL devices. In addition to the aromatic amine derivative layer and the nitrogen-containing heterocyclic derivative layer, a layer constituting the hole-transport region may be provided. Any material used for forming such a layer can be selected from known materials as mentioned above. The aromatic amine derivative includes a compound represented by the following formula:

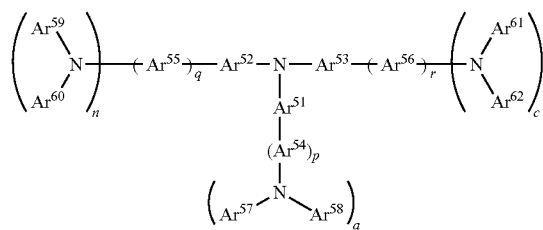

wherein $Ar^57$ to $Ar^{62}$, $Ar^{51}$ to $Ar^{53}$ and $Ar^{54}$ to $Ar^{56}$ are independently a substituted or unsubstituted aromatic group having 6 to 50 ring carbon atoms or a heteroaromatic group having 5 to 50 ring atoms, a to c and p to r are independently an integer of 0 to 3, and $Ar^{57}$ and $Ar^{58}$, $Ar^{59}$ and $Ar^{60}$, $Ar^{61}$ and $Ar^{62}$ are independently may bond to each other to form a saturated or unsaturated ring.

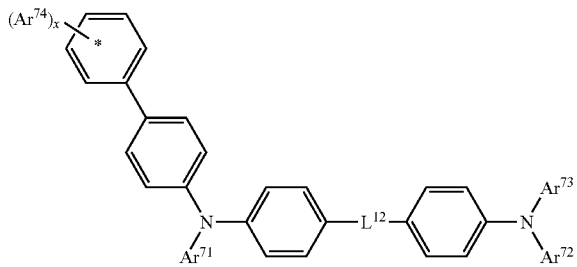

wherein $Ar^{71}$ to $Ar^{74}$ are a substituted or unsubstituted aromatic group having 6 to 50 ring carbon atoms or a heteroaromatic group having 5 to 50 ring atoms, $L^{12}$ is a linking group and represents a single bond, or a substituted or unsubstituted aromatic group having 6 to 50 ring carbon atoms or a heteroaromatic group having 5 to 50 ring carbon atoms, x is an integer of 0 to 5, and $Ar^{72}$ and $Ar^{73}$ may bond to each other to form a saturated or unsaturated ring.

Specific examples include triazole derivatives (see U.S. Pat. No. 3,112,197), oxadiazole derivatives (see U.S. Pat. No. 3,189,447), imidazole derivatives (see JP-B-S37-16096), polyarylalkane derivatives (see U.S. Pat. No. 3,615,402, U.S. Pat. No. 3,820,989, U.S. Pat. No. 3,542,544, JP-B-S45-555, JP-B-S51-10983, JP-A-S51-93224, JP-A-S55-17105, JP-A-S56-4148, JP-A-S55-108667, JP-A-S55-156953, JP-A-S56-36656), pyrazoline derivatives and pyrazolone derivatives (see U.S. Pat. No. 3,180,729, U.S. Pat. No. 4,278,746, JP-A-S55-88064, JP-A-S55-88065, JP-A-S49-105537, JP-A-S55-51086, JP-A-S56-80051, JP-A-S56-88141, JP-A-S57-45545, JP-A-S54-112637 and JP-A-S55-74546), phenylenediamine derivatives (see U.S. Pat. No. 3,615,404, JP-B-S51-10105, JP-B-S46-3712, JP-B-S47-25336 and JP-B-S54-119925), arylamine derivatives (see U.S. Pat. No. 3,567,450, U.S. Pat. No. 3,240,597, U.S. Pat. No. 3,658,520, U.S. Pat. No. 4,232,103, U.S. Pat. No. 4,175,961, U.S. Pat. No. 4,012,376, JP-B-S49-35702, JP-B-S39-27577, JP-A-S55-144250, JP-A-S56-119132, JP-A-S56-22437 and West Germany Patent No. 1,110,518), amino-substituted chalcone derivatives (see U.S. Pat. No. 3,526,501), oxazole derivatives (disclosed in U.S. Pat. No. 3,257,203), styryl anthracene derivatives (see JP-A-556-46234), fluorenone derivatives (see JP-A-S54-110837), hydrazone derivatives (see U.S. Pat. No. 3,717,462, JP-A-S54-59143, JP-A-555-52063, JP-A-555-52064, JP-A-S55-46760, JP-A-S57-11350, JP-A-S57-148749 and JP-A-H2-311591), stilbene derivatives (see JP-A-S61-210363, JP-A-S61-228451, JP-A-S61-14642, JP-A-S61-72255, JP-A-S62-47646, JP-A-S62-36674, JP-A-S62-10652, JP-A-S62-30255, JP-A-S60-93455, JP-A-S60-94462, JP-A-S60-174749 and JP-A-S60-175052), silazane derivatives (U.S. Pat. No. 4,950,950), polysilanes (JP-A-H2-204996), aniline-based copolymers (JP-A-H2-282263), and conducive high molecular oligomers (particularly thiophene oligomer).

The hole-injecting layer may contain an amino derivative represented by the following formula in addition to the above-mentioned compounds.

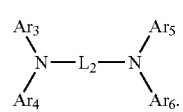

(2)

In the formula (2), $L_2$ is a substituted or unsubstituted arylene group having 10 to 40 carbon atoms.

Preferably, a biphenylene group, a terphenylene group, a quaterphenylene group, a naphthylene group, an anthracenylene group, a phenanthrylene group, a chrysenylene group, a pyrenylene group, a fluorenylene group, a 2,6-diphenylnaphthalene-4',4"-ene group, 2-phenylnaphthalene-2,4'-ene group, a 1-phenylnaphthalene-1,4'-ene group, a 2,7-diphenylfluorenylene-4'4"-ene group, a fluorenylene group, a 9,10-diphenylanthracenylene-4',4"-ene group, a 6,12-diphenylchrysenylen-4',4"-ene group and the like may be mentioned.

More preferably, a biphenylene group, a terphenylene group, a fluorenylene group, a 2-phenylnaphthalene-2,4'-ene group, a 1-phenylnaphthalene-1,4'-ene group and 6,12-diphenylchrysenylen-4',4"-ene group may be mentioned.

$Ar_3$ to $Ar_6$ in the formula (2) are independently a substituted or unsubstituted aromatic hydrocarbon ring group having 6 to 60 ring carbon atoms or a substituted or unsubstituted aromatic heterocyclic group having 6 to 60 ring atoms.

In $Ar_3$ to $Ar_6$ in the formula (2), the substituted or unsubstituted aromatic hydrocarbon ring group having 6 to 60 ring carbon atoms is the same as $Ar_1$ and $Ar_2$ in the formula (1).

The substituted or unsubstituted aromatic heterocyclic group having 6 to 60 ring atoms includes a 5- or 6-membered single ring or a fused ring composed of 2 to 5 5- or 6-membered rings. Specific examples include a pyridyl group, a triazinyl group, a pyrazinyl group, a quinoxalinyl group and a thienyl group.

The amine derivative represented by the formula (2) is preferably a compound represented by the following formula (3):

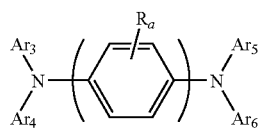
(3)

In the formula (3), $Ar_3$ to $Ar_6$ are the same as $Ar_3$ to $Ar_6$ in the formula (2).

In the formula (3), $R_a$ is a substituent. Specific examples of $R_a$ are the same as the substituents such as Z in the above-mentioned formula (1).

n is an integer of 2 to 4, preferably 2 or 3.

More preferably, the amine derivative represented by formula (2) is a compound represented by formula (4) or (5).

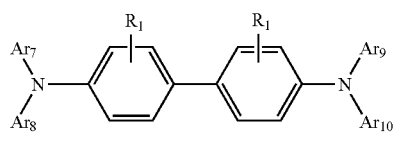
(4)

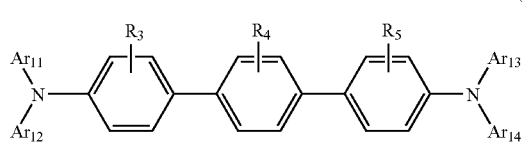
(5)

In the formula, $R_1$ to $R_5$ are substituents, and specific examples are the same as those for $R_a$ in the formula (3). $R_1$ and $R_2$, and $R_3$ to $R_5$ may bond to each other to form a saturated or unsaturated ring.

In the formula, $Ar_7$ to $Ar_{14}$ are independently a substituted or unsubstituted aromatic hydrocarbon ring group having 6 to 60 ring carbon atoms or a substituted or unsubstituted aromatic heterocyclic group having 6 to 60 ring atoms. Specific examples of $Ar_7$ to $Ar_{14}$ include the same groups as those for $Ar_1$ and $Ar_2$ in the formula (1).

The substituents of $Ar_7$ to $Ar_{14}$, and $R_1$ to $R_5$ are preferably the same substituents of $R_1$ to $R_{10}$ in the formulas (1) and (2). As the substituted or unsubstituted ring formed by bonding $R_1$ and $R_2$, the following structures may be mentioned. Also, in the case where $R_3$ to $R_5$ bond to each other to form a ring, the same is applicable.

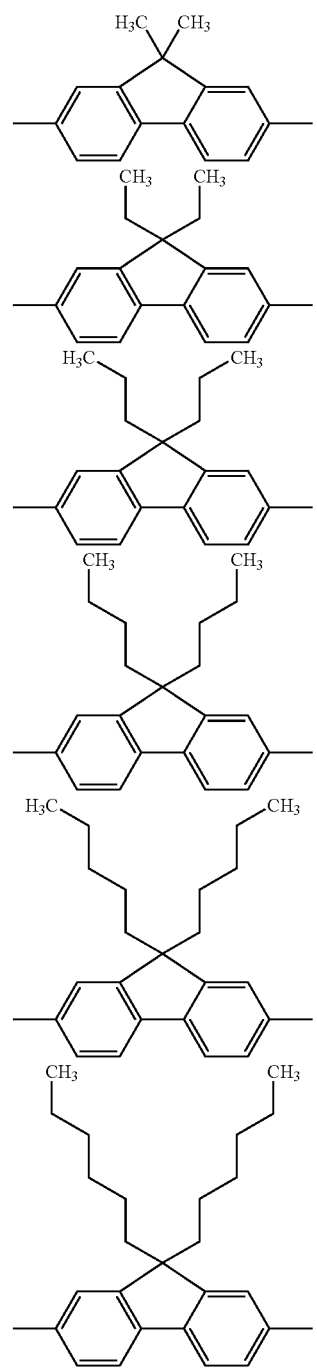

-continued
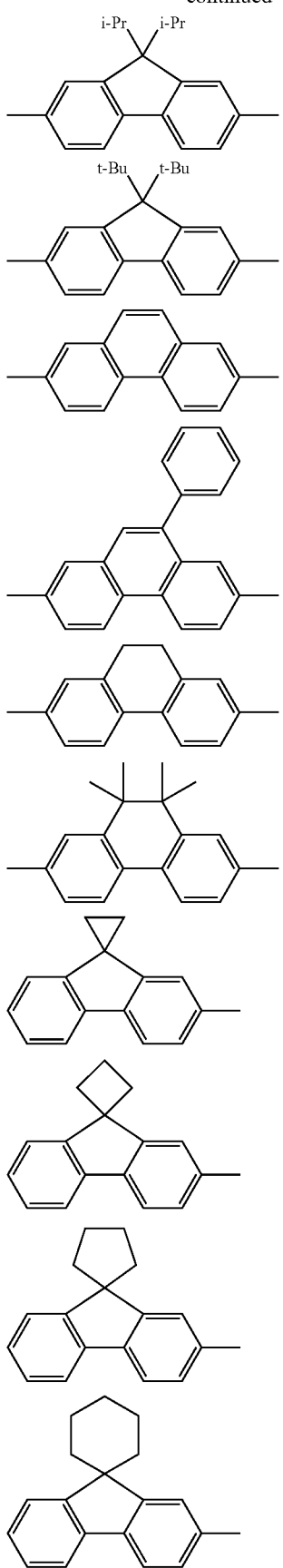
-continued
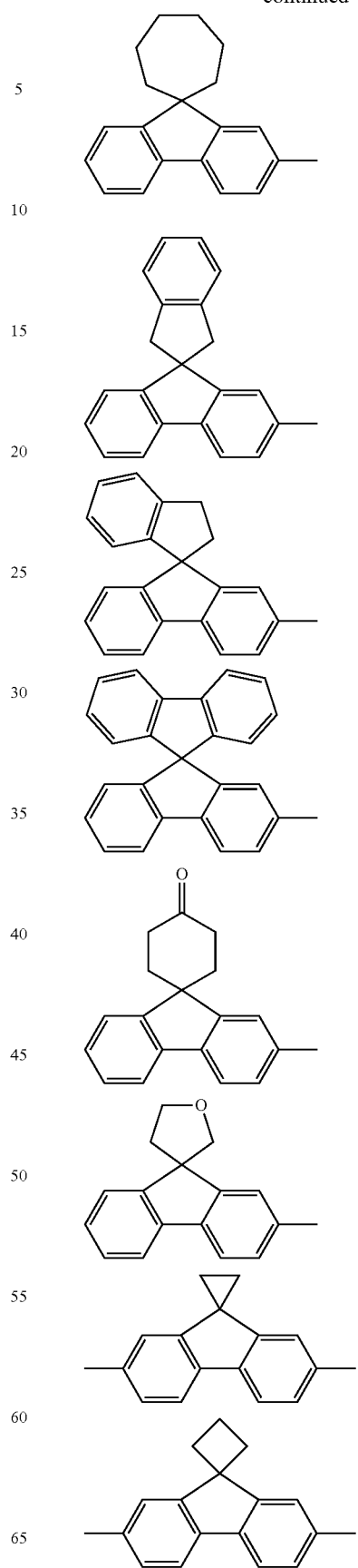

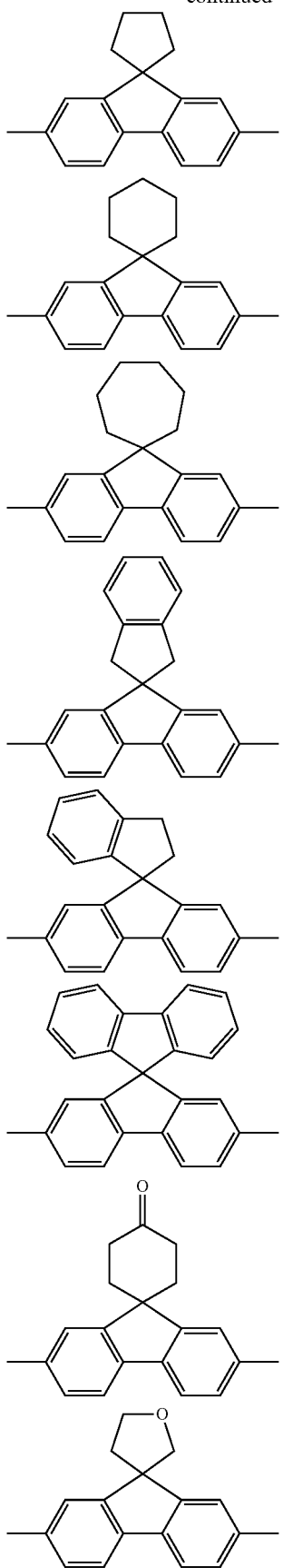
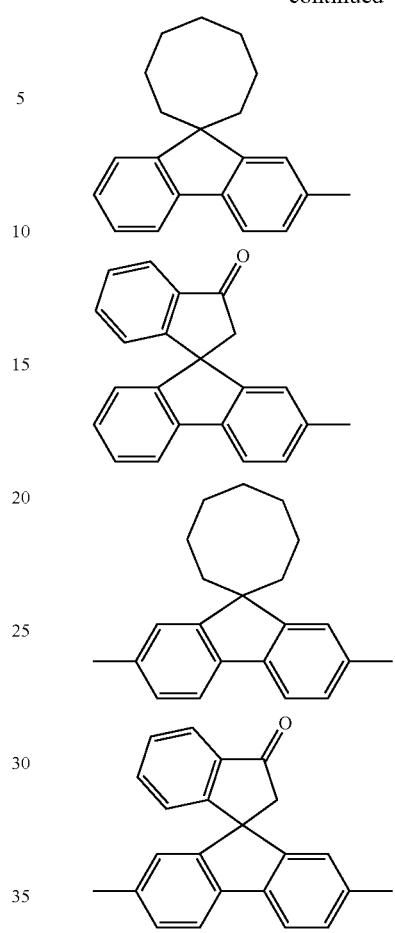
Preferable structures are as follows:
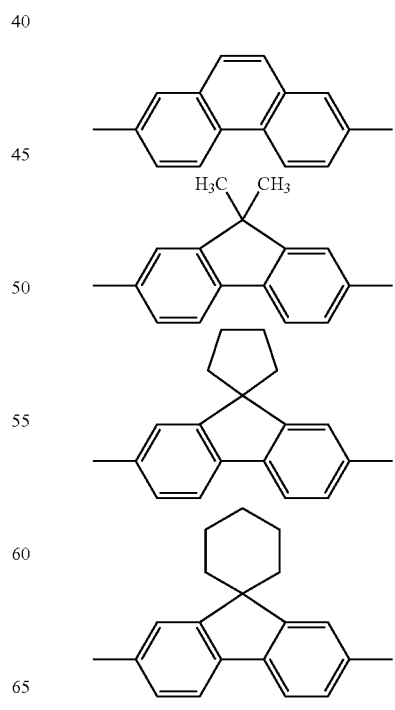

At least one of $Ar_7$ to $Ar_{10}$ in the formula (4) and at least one of $Ar_{11}$ to $Ar_{14}$ in the formula (5) are preferably a substituted or unsubstituted biphenyl group.

The substituted or unsubstituted biphenyl group includes a 2-biphenyl group, a 3-biphenyl group, a 4-biphenyl group, a p-terphenyl group, a m-terphenyl group, an o-terphenyl group, a 4'-methyl-biphenyl-4-yl group, a 4'-t-butyl-biphenyl-4-yl group, a 4'-(1-naphthyl)-biphenyl-4-yl group, a 4'-(2-naphthyl)-biphenyl-4-yl group, a 2-fluorenyl group and a 9,9-dimethyl-2-fluorenyl group.

Preferred are a 3-biphenyl group, a 4-biphenyl group, a p-terphenyl group, a m-terphenyl group and a 9,9-dimethyl-2-fluorenyl group.

At the terminal of the substituted or unsubstituted biphenyl group, an arylamino group may be substituted.

Specific examples of the amine derivatives are shown below:

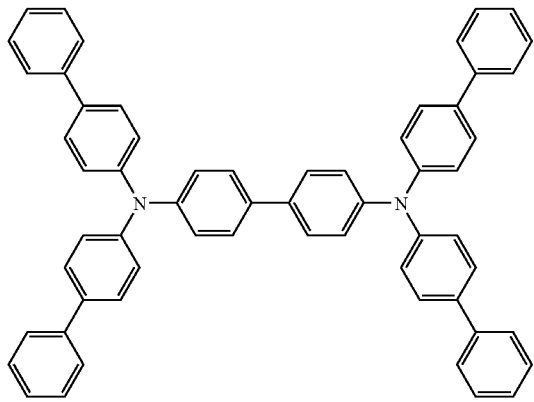

B-1

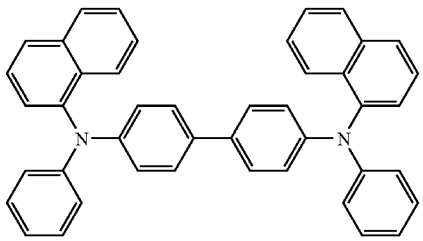

B-2

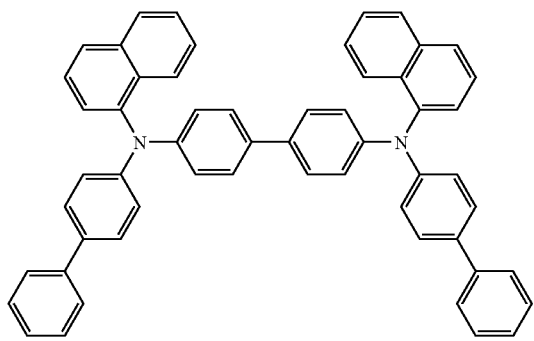

B-3

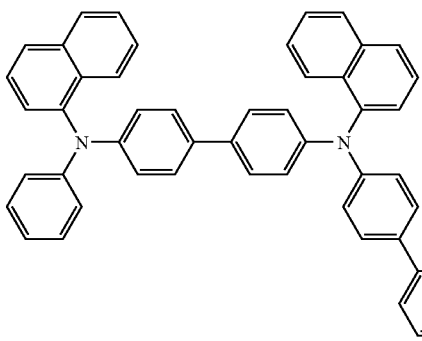

B-4

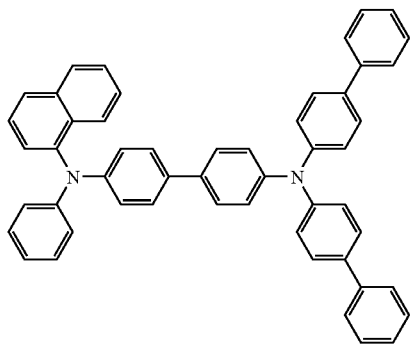

B-5

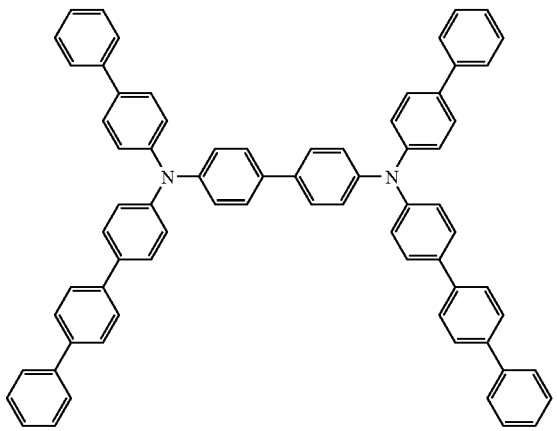

B-6

-continued
B-7
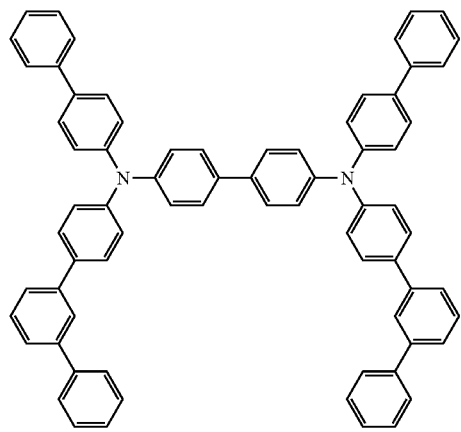
B-8
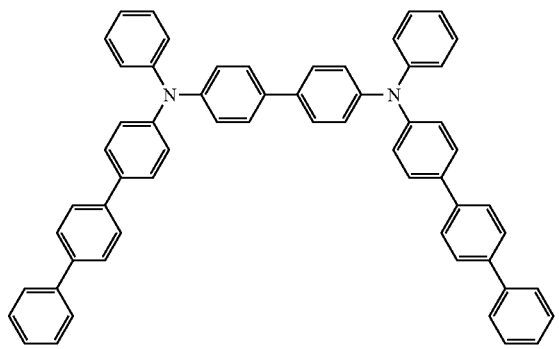
B-9
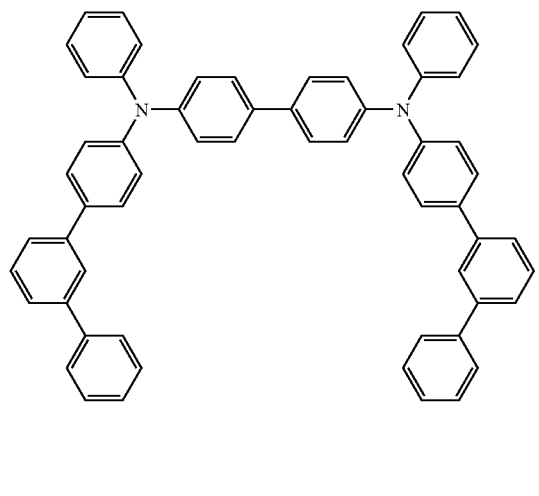
B-10
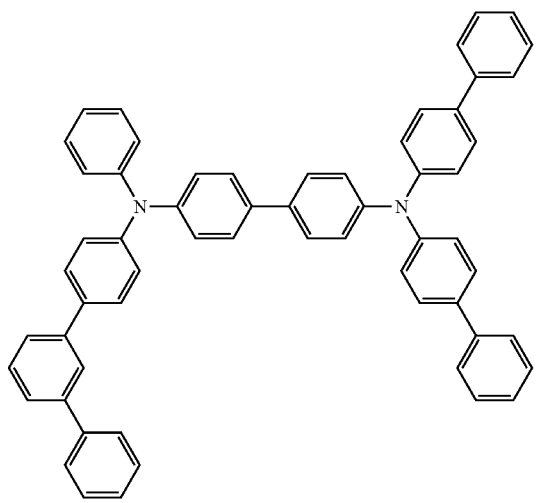
B-11
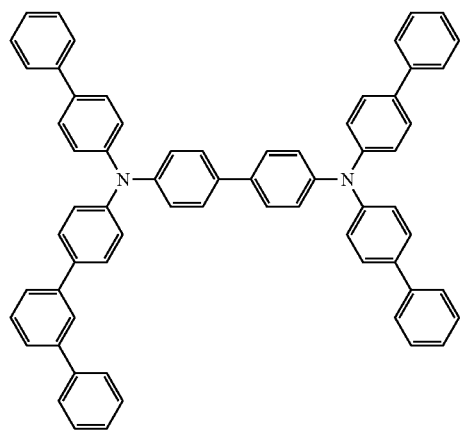
B-12
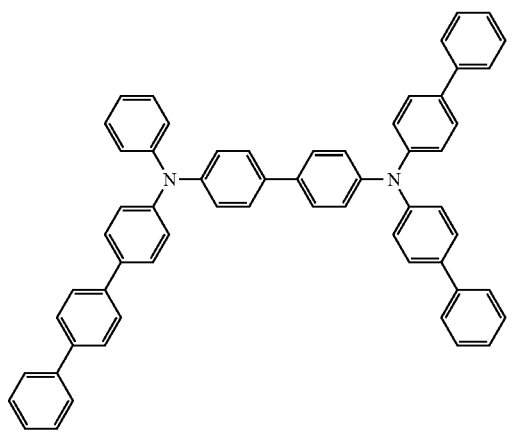

-continued
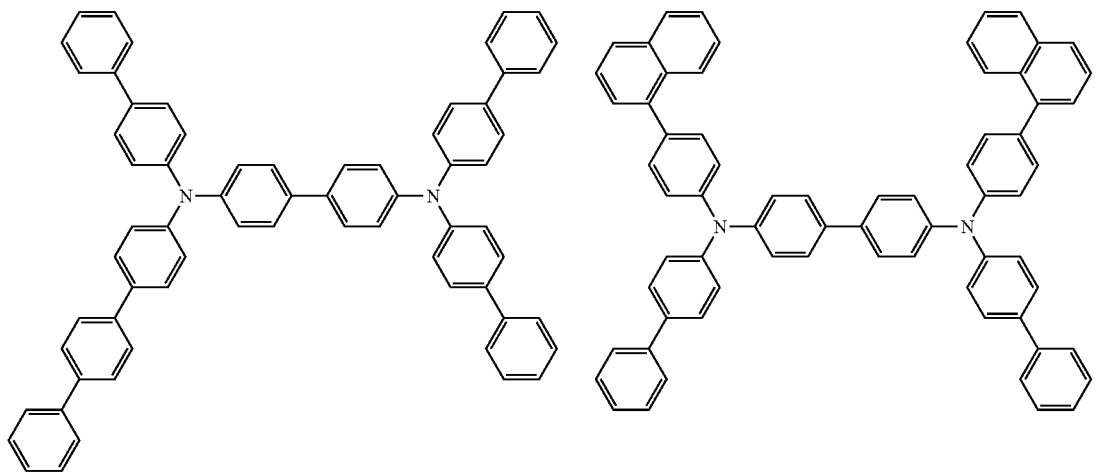
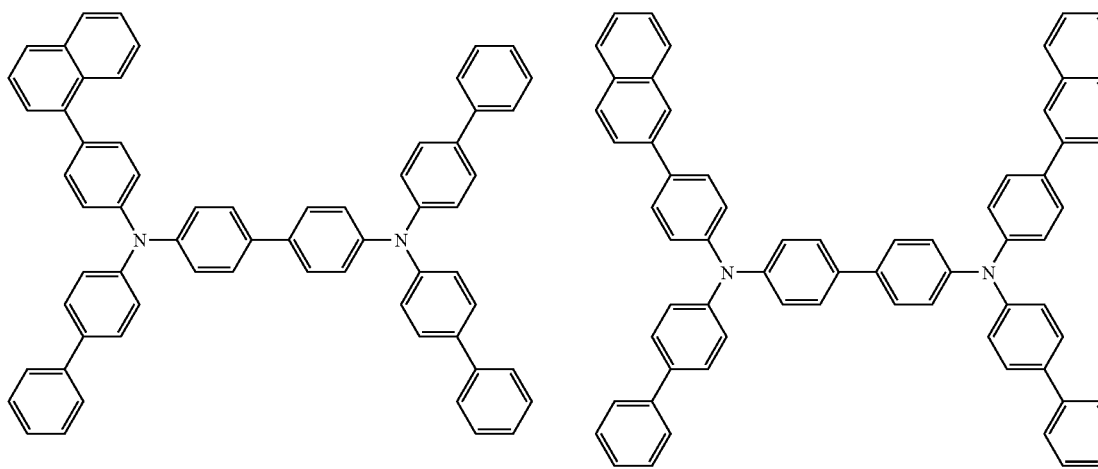
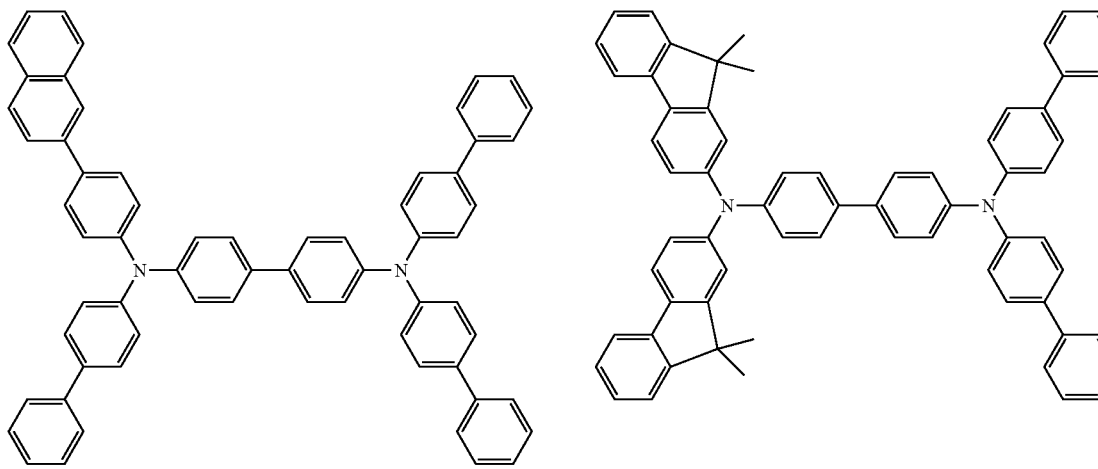

-continued
B-19
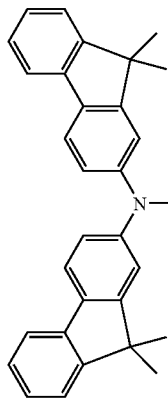
B-20
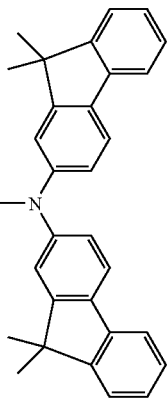
B-21
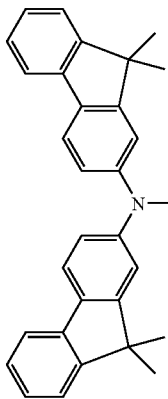
B-22
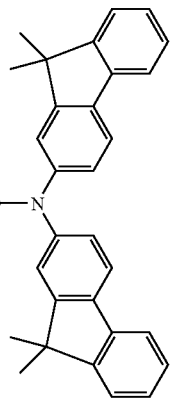
B-23
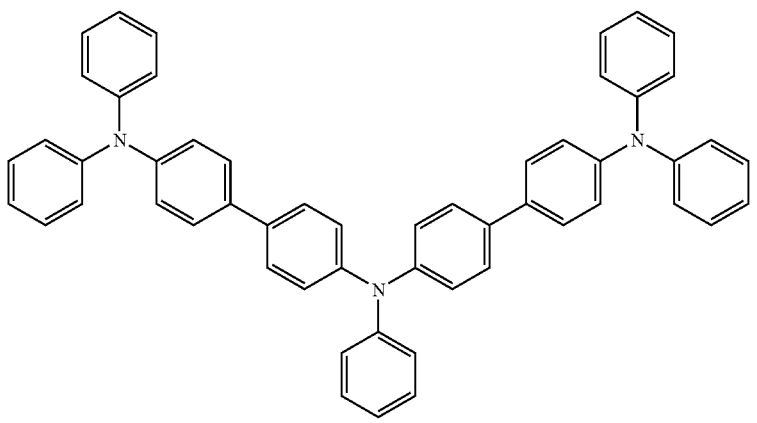

B-24
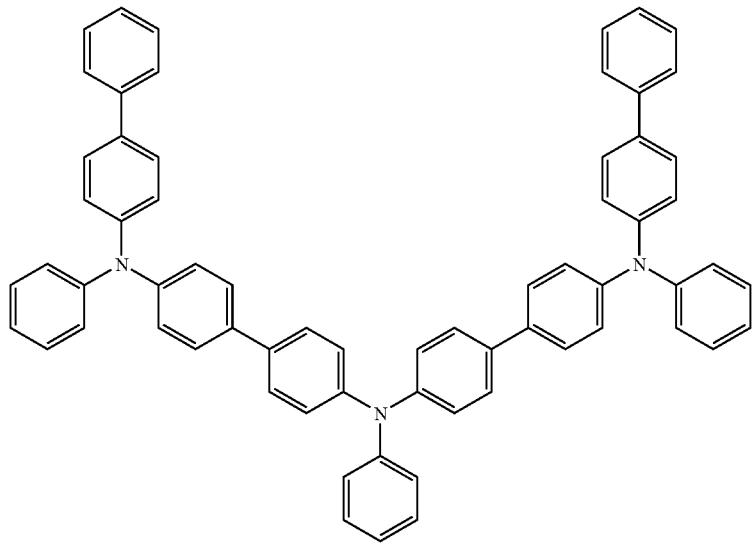
B-25
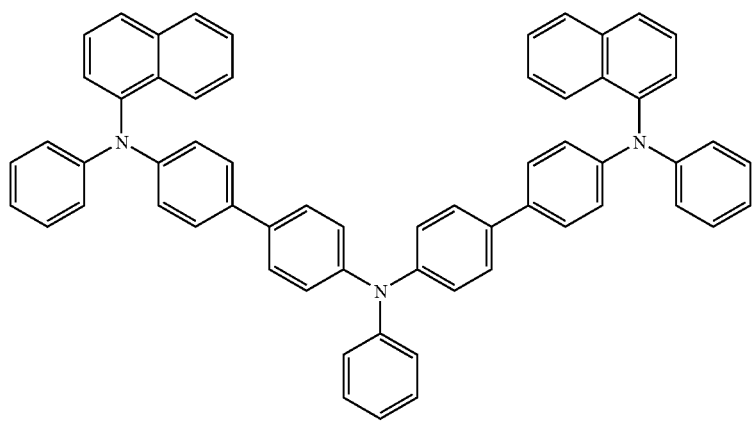
B-26
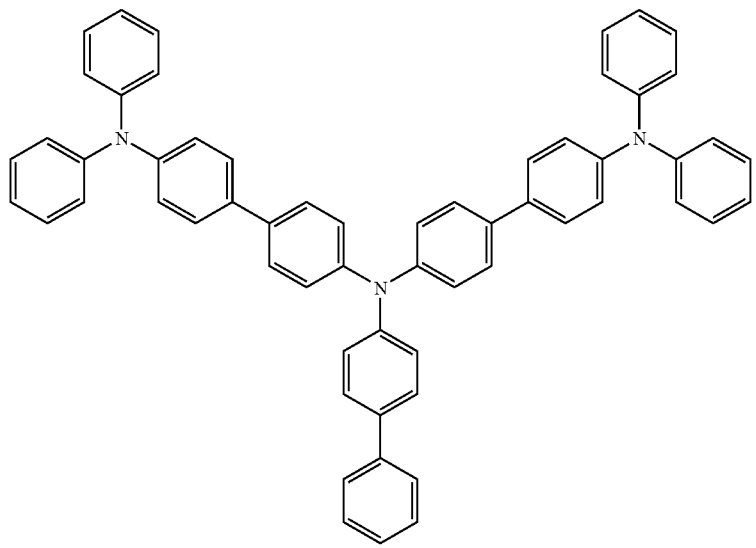

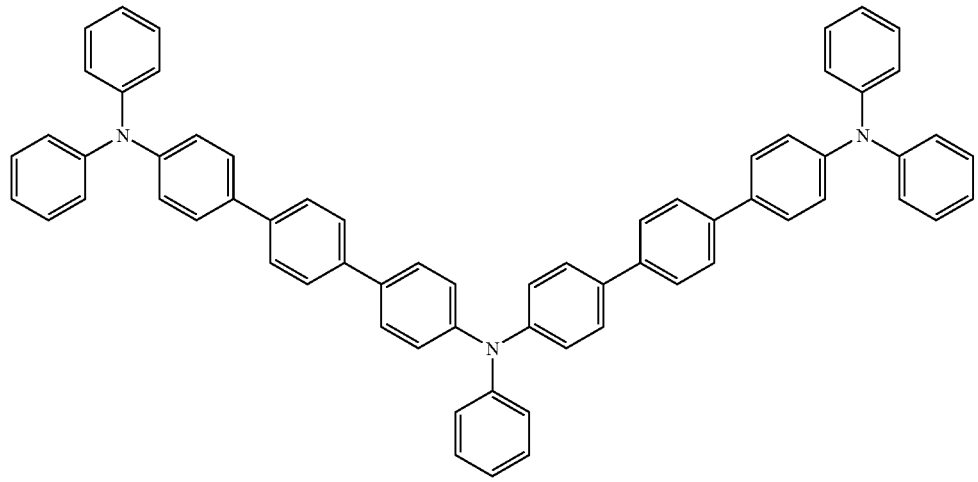
B-27
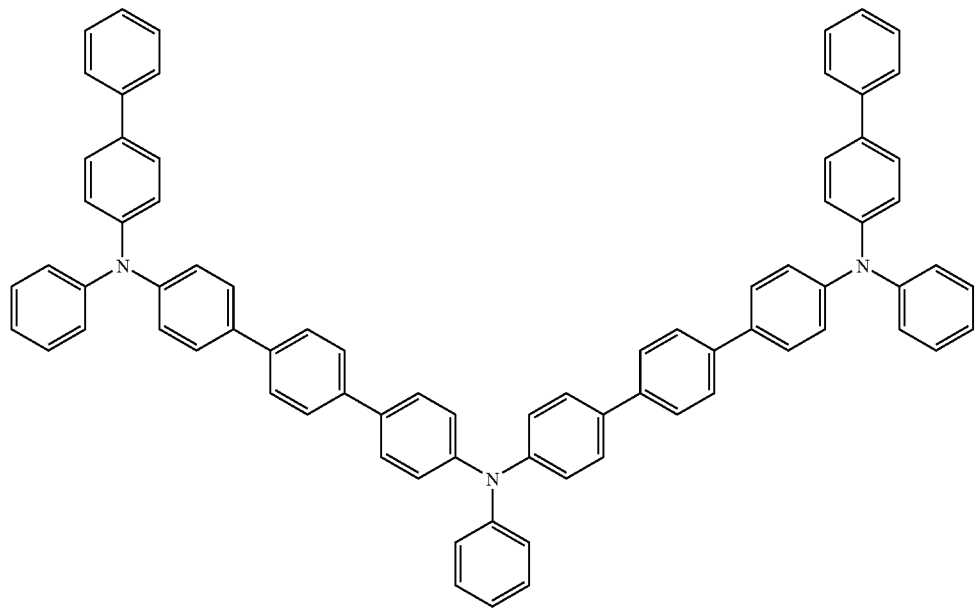
B-28

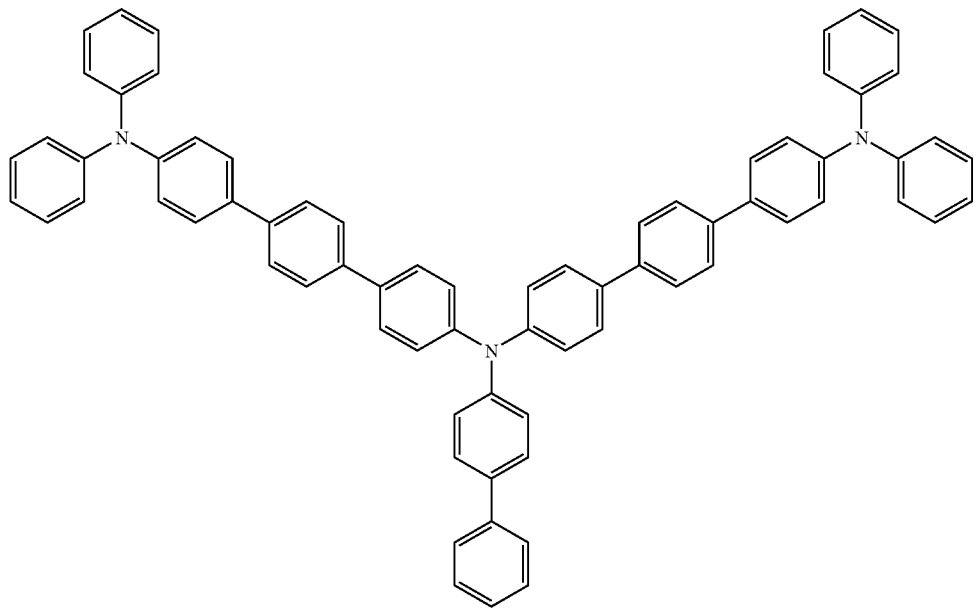
B-29
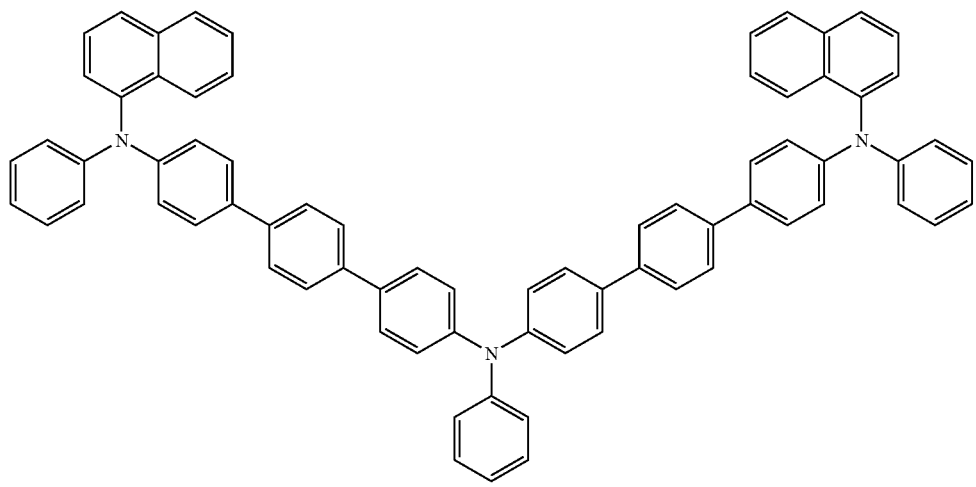
B-30
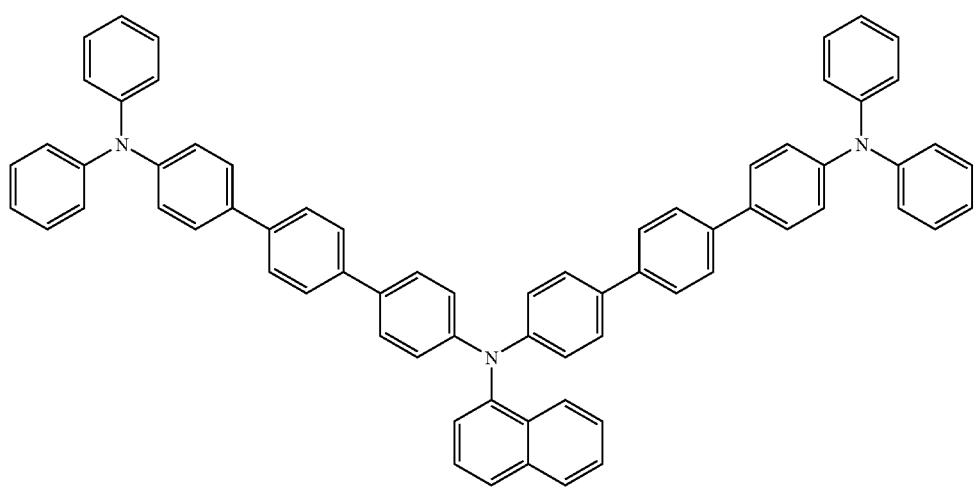
B-31

B-32
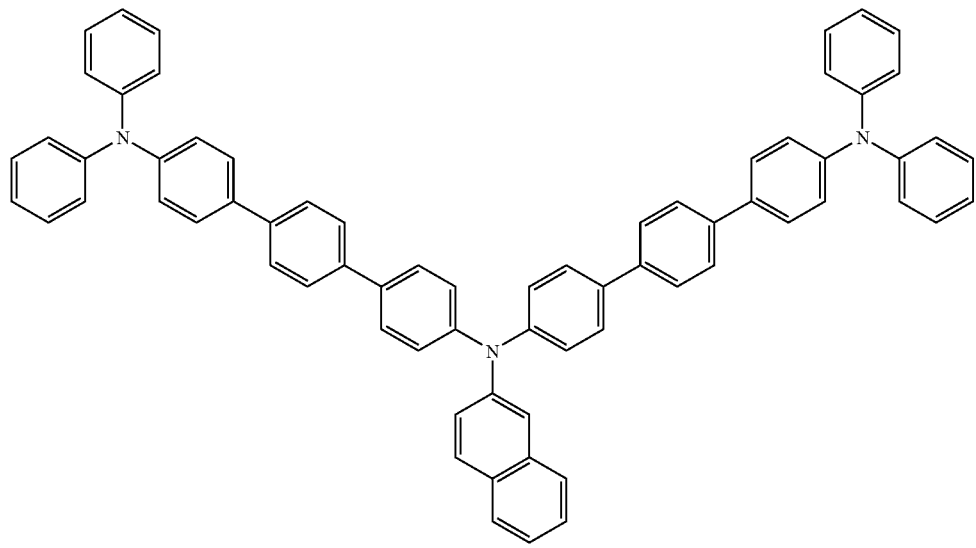
B-33
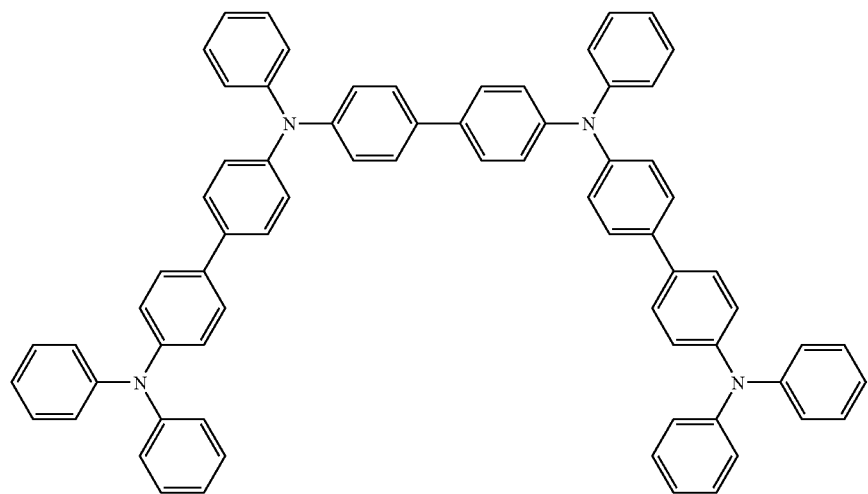
B-34
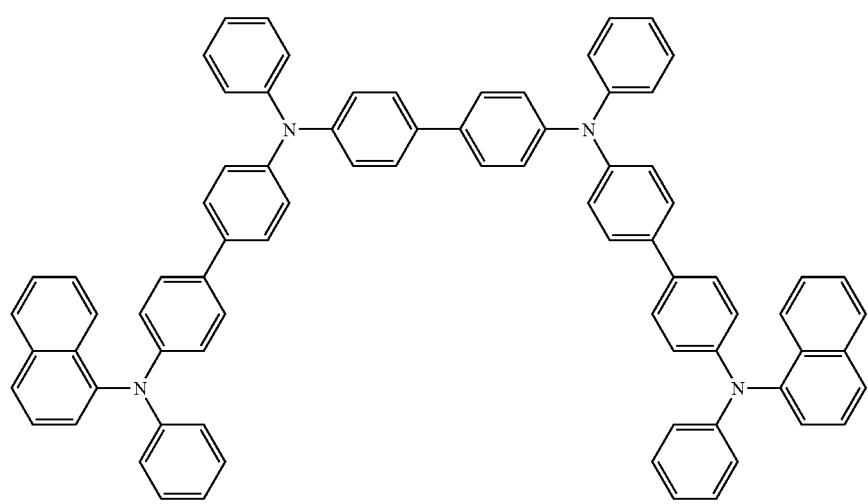

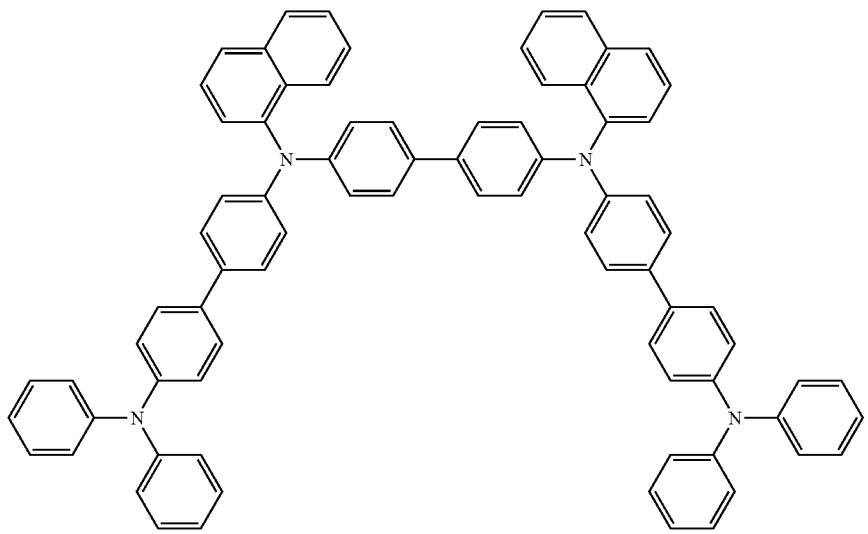
B-35
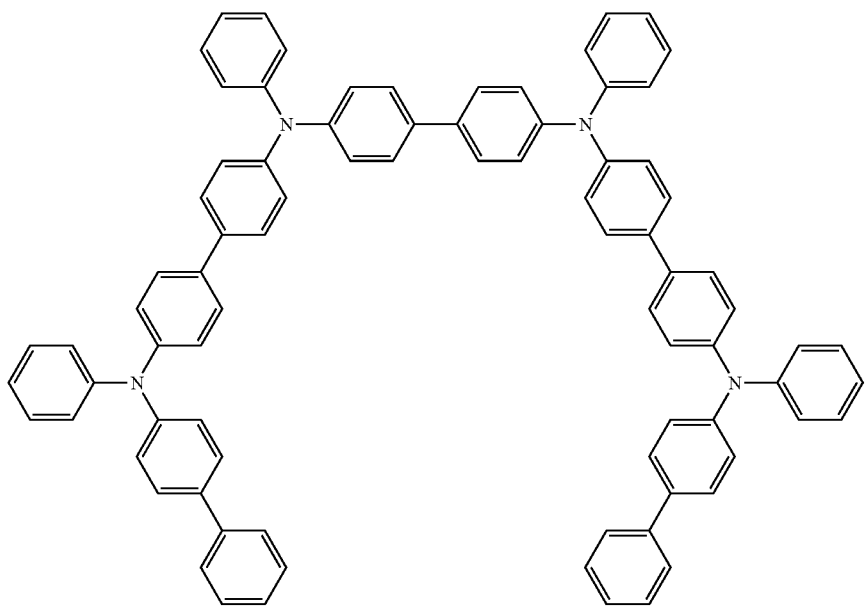
B-36
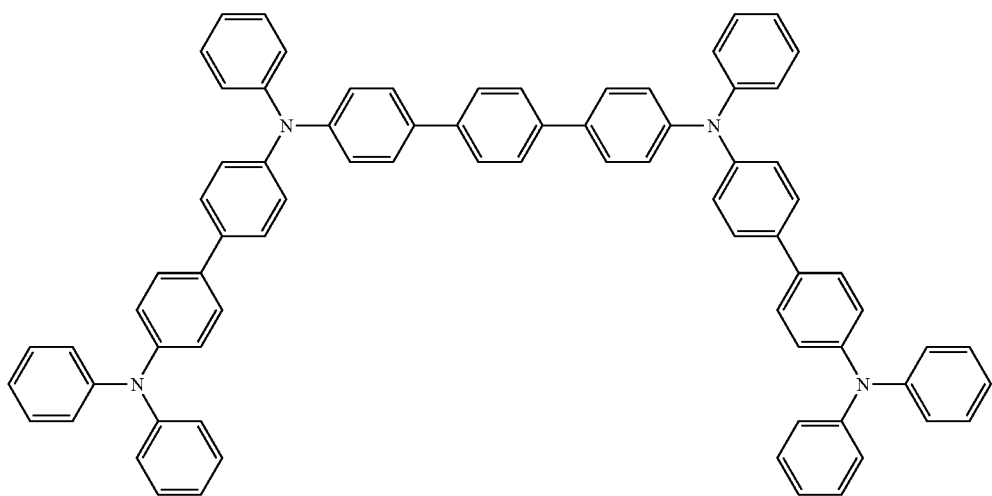
B-37

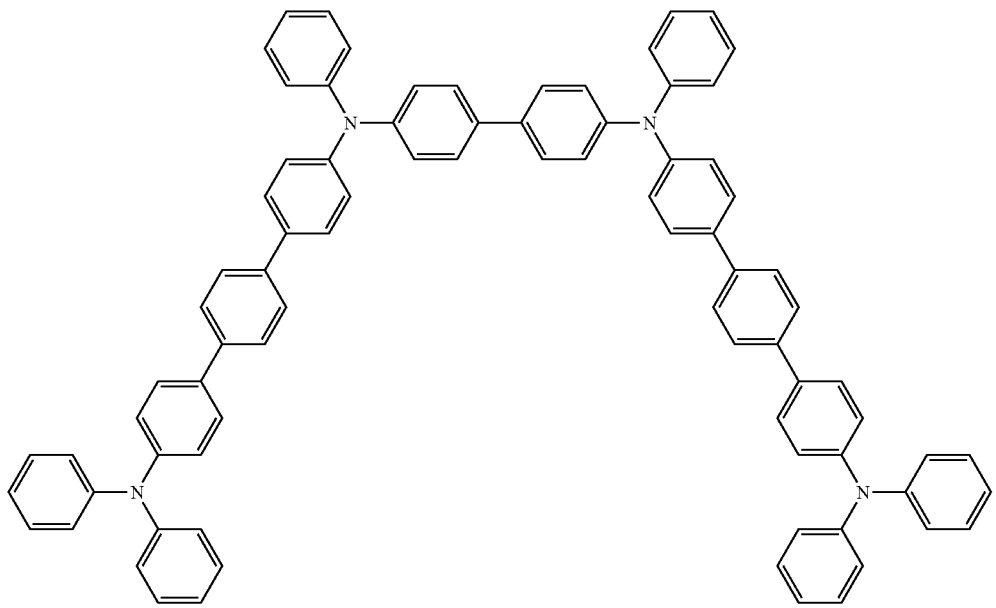

B-38

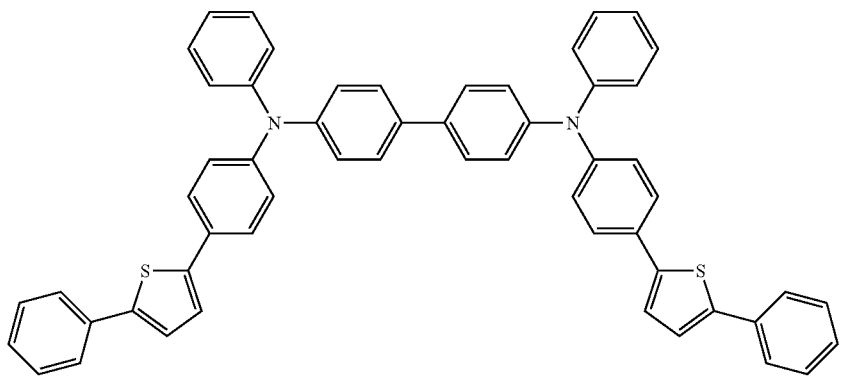

B-39

The hole-transporting layer may contain a fluorene-based compound represented by the following formula (9):

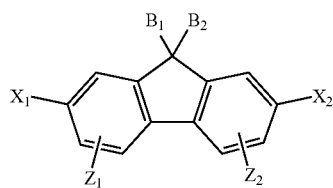

(9)

In the formula, $X_1$ is an N-carbazoyl group which may be substituted by single or plural substituents selected from a halogen atom, an alkyl group having 1 to 10 carbon atoms, an alkoxy group having 1 to 10 carbon atoms and an aryl group having 6 to 10 carbon atoms, an N-phenoxazyl which may be substituted by single or plural substituents selected from a halogen atom, an alkyl group having 1 to 10 carbon atoms, an alkoxy group having 1 to 10 carbon atoms and an aryl group having 6 to 10 carbon atoms, or an N-phenothiazyl group which may be substituted by single or plural substituents selected from a halogen atom, an alkyl group having 1 to 10 carbon atoms, an alkoxy group having 1 to 10 carbon atoms and an aryl group having 6 to 10 carbon atoms.

$X_2$ is an N-carbazoyl group which may be substituted by single or plural substituents selected from a halogen atom, an alkyl group having 1 to 10 carbon atoms, an alkoxy group having 1 to 10 carbon atoms and an aryl group having 6 to 10 carbon atoms, an N-phenoxazyl group which may be substitued by single or plural substituents selected from a halogen atom, an alkyl group having 1 to 10 carbon atoms, an alkoxy group having 1 to 10 carbon atoms or an aryl group having 6 to 10 carbon atoms, an N-phenothiazyl group which may be substituted by single or plural substituents selected from a halogen atom, an alkyl group having 1 to 10 carbon atoms, an alkoxy group having 1 to 10 carbon atoms and an aryl group having 6 to 10 carbon atoms, or a —$NAr^{21'}Ar^{22'}$ group (where $Ar^{21'}$ and $Ar^{22'}$ are a carbocyclic aromatic group having 6 to 20 carbon atoms in total or a heterocyclic aromatic group having 3 to 20 carbon atoms in total, which may be substituted by single or plural substituents selected from a halogen atom, an alkyl group, an alkoxy group and an aryl group).

$B_1$ and $B_2$ are a hydrogen atom, a straight, branched or cyclic alkyl group, a carbocyclic aromatic group having 6 to 20 carbon atom in total or a heterocyclic aromatic group having 3 to 20 carbon atoms in total, which may be substituted by single or plural substituents selected from a halogen atom, an alkyl group, an alkoxy group and an aryl group, or an aralkyl group which may be substituted by single or plural substituents selected from a halogen atom, an alkyl group, an alkoxy group and an aryl group;

$Z_1$ and $Z_2$ are a hydrogen atom, a halogen atom, a straight, branched or cyclic alkyl group, a straight, branched or cyclic alkoxy group or a carbocyclic aromatic group having 6 to 20 carbon atoms in total or a heterocyclic aromatic group having 3 to 20 carbon atoms in total, which may be substituted by single or plural substituents selected from a halogen atom, an alkyl group, an alkoxy group and an aryl group.

In the compound represented by the formula (9), X1 is a substituted or unsubstituted N-carbazoyl group, a substituted or unsubstituted N-phenoxazyl group or a substituted or unsubstituted N-phenothiazyl group, preferably an N-carbazoyl group, N-phenoxazyl group or an N-phenothiazyl group, which may be substituted by single or plural substituents selected from, for example, a halogen atom, an alkyl group having 1 to 10 carbon atoms, an alkoxy group having 1 to 10 carbon atoms and an aryl group having 6 to 10 carbon atoms, more preferably an N-carbazoyl group, an N-phenoxazyl group or an N-phenothiazyl group, which may be substituted by single or plural substituents selected from a halogen atom, an alkyl group having 1 to 4 carbon atoms, an alkoxy group having 1 to 4 carbon atoms and an aryl group having 6 to 10 carbon atoms, and further preferably an unsubstituted N-carbazoyl group, an unsubstituted N-phenoxazyl group or an unsubstituted N-phenothiazyl group.

Specific examples of the substituted or unsubstituted N-carbazoyl group, the substituted or unsubstituted N-phenoxazyl group or the substituted or unsubstituted N-phenothiazyl group for $X_1$ include an N-carbazoyl group, an 2-methyl-N-carbazoyl group, a 3-methyl-N-carbazoyl group, a 4-methyl-N-carbazoyl group, a 3-n-butyl-N-carbazoyl group, a 3-n-hexyl-N-carbazoyl group, a 3-n-octyl-N-carbazoyl group, a 3-n-decyl-N-carbazoyl group, a 3,6-dimethyl-N-carbazoyl group, a 2-methoxy-N-carbazoyl group, a 3-methoxy-N-carbazoyl group, a 3-ethoxy-N-carbazoyl group, a 3-isopropoxy-N-carbazoyl group, a 3-n-butoxy-N-carbazoyl group, a 3-n-octyloxy-N-carbazoyl group, a 3-n-decyloxy-N-carbazoyl group, a 3-phenyl-N-carbazoyl group, a 3-(4'-methylphenyl)-N-carbazoyl group, a 3-chloro-N-carbazoyl group, an N-phenoxazyl group, an N-phenothiazyl group and a 2-methyl-N-phenothiazyl group. In the compound represented by the general formula (1), $X_2$ is a substituted or unsubstituted N-carbazoyl group, a substituted or unsubstituted N-phenoxazyl group, a substituted or unsubstituted N-phenothiazyl group or a —$NAr^{21'}Ar^{22'}$ group (where $Ar^{21'}$ and $Ar^{22'}$ are a substituted or unsubstituted aryl group).

Specific examples of the substituted or unsubstituted N-carbazoyl group, the substituted or unsubstituted N-phenoxazyl group and the substituted or unsubstituted N-phenothiazyl group for $X_2$ include the substituted or unsubstituted N-carbazoyl group, the substituted or unsubstituted N-phenoxazyl group and the substituted or unsubstituted N-phenothiazyl group which are mentioned as the specific examples for $X_1$.

In the —$NAr^{21'}Ar^{22'}$ group, $Ar^{21'}$ and $Ar^{22'}$ are a substituted or unsubstituted aryl group. Here, the aryl group includes carbocyclic aromatic groups such as a phenyl group, a naphthyl group and an anthryl group, and heterocyclic aromatic groups such as a furyl group, a thienyl group and a pyridyl group. $Ar^{21'}$ and $Ar^{22'}$ are preferably a carbocyclic aromatic group having 6 to 20 carbon atoms in total or a heterocyclic aromatic group having 3 to 20 carbon atoms in total, which may be substituted by single or plural substituents selected from a halogen atom, an alkyl group, an alkoxy group and an aryl group, more preferably a carbocyclic aromatic group having 6 to 20 carbon atoms in total which may be substituted by single or plural substituents selected from a halogen atom, an alkyl group having 1 to 14 carbon atoms, an alkoxy group having 1 to 14 carbon atoms and an aryl group having 6 to 10 carbon atoms, and further preferably a carbocyclic aromatic group having 6 to 16 carbon atoms in total which may be substituted by single or plural substituents selected from a halogen atom, an alkyl group having 1 to 4 carbon atoms, an alkoxy group having 1 to 4 carbon atoms and an aryl group having 6 to 10 carbon atoms.

Specific examples of $Ar^{21'}$ and $Ar^{22'}$ include, though not limited to thereto, a phenyl group, 1-naphthyl group, 2-naphthyl group; 2-anthryl group, 9-anthryl group, 4-quinolyl group, 4-pyridyl group, 3-pyridyl group, 2-pyridyl group, 3-furyl group, 2-furyl group, 3-thienyl group, 2-thienyl group, 2-oxazolyl group, 2-thiazolyl group, 2-benzoxazolyl group, 2-benzothiazolyl group, 2-benzoimidazolyl group, 4-methylphenyl group, 3-methylphenyl group, 2-methylphenyl group, 4-ethylphenyl group, 3-ethylphenyl group, 2-ethylphenyl group, 4-n-propylphenyl group, 4-isopropylphenyl group, 2-isopropylphenyl group, 4-n-butylphenyl group, 4-isobutyl phenyl group, 4-sec-butylphenyl group, 2-sec-butylphenyl group, 4-tert-butylphenyl group, 3-tert-butylphenyl group, 2-tert-butylphenyl group, 4-n-pentylphenyl group, 4-isopentylphenyl group, 2-neopentylphenyl group, 4-tert-pentylphenyl group, 4-n-hexylphenyl group, 4-(2'-ethylbutyl)phenyl group, 4-n-heptylphenyl group, 4-n-octylphenyl group, 4-(2'-ethylhexyl)phenyl group, 4-tert-octylphenyl group, 4-n-decylphenyl group, 4-n-dodecylphenyl group, 4-n-tetradecylphenyl group, 4-cyclopentylphenyl group, 4-cyclohexylphenyl group, 4-(4'-methylcyclohexyl)phenyl group, 4-(4'-tert-butylcyclohexyl)phenyl group, 3-cyclohexylphenyl group, 2-cyclohexylphenyl group, 4-ethyl-1-naphthyl group, 6-n-butyl-2-naphthyl group, 2,4-dimethylphenyl group, 2,5-dimethylphenyl group, 3,4-dimethylphenyl group, 3,5-dimethylphenyl group, 2,6-dimethylphenyl group, 2,4-diethylphenyl group, 2,3,5-trimethylphenyl group, 2,3,6-trimethylphenyl group, 3,4,5-trimethylphenyl group, 2,6-diethylphenyl group, 2,5-diisopropylphenyl group, 2,6-diisobutylphenyl group, 2,4-di-tert-butylphenyl group, 2,5-di-tert-butylphenyl group, 4,6-di-tert-butyl-2-methylphenyl group, 5-tert-butyl-2-methylphenyl group, 4-tert-butyl-2,6-dimethylphenyl group, 4-methoxyphenyl group, 3-methoxyphenyl group, 2-methoxyphenyl group, 4-ethoxyphenyl group, 3-ethoxyphenyl group, 2-ethoxyphenyl group, 4-n-propoxyphenyl group, 3-n-propoxyphenyl group, 4-isopropoxyphenyl group, 2-isopropoxyphenyl group, 4-n-buthoxyphenyl group, 4-isobuthoxyphenyl group, 2-sec-buthoxyphenyl group, 4-n-pentyloxyphenyl group, 4-isopentyloxyphenyl group, 2-isopentyloxyphenyl group, 4-neopentyloxyphenyl, group, 2-neopentyloxyphenyl group, 4-n-hexyloxyphenyl group, 2-(2'-ethylbutyl)oxyphenyl group, 4-n-octyloxyphenyl group, 4-n-decyloxyphenyl group, 4-n-dodecyloxyphenyl group, 4-n-tetradecyloxyphenyl group, 4-cyclohexyloxyphenyl group, 2-cyclohexyloxyphenyl group, 2-methoxy-1-naphthyl group, 4-methoxy-1-naphthyl group, 4-n-buthoxy-1-naphthyl group, 5-ethoxy-1-naphthyl group, 6-methoxy-2-naphthyl group, 6-ethoxy-2-naphthyl group, 6-n-buthoxy-2-naphthyl group, 6-n-hexyloxy-2-naphthyl group, 7-methoxy-2-naphthyl group, 7-n-buthoxy-2-naphthyl group, 2-methyl-4-methoxyphenyl group, 2-methyl-5-methoxy phenyl group, 3-methyl-5-methoxyphenyl group, 3-ethyl-5-methoxyphenyl group, 2-methoxy-4-methylphenyl group, 3-methoxy-4-methylphenyl group, 2,4-dimethoxyphenyl group, 2,5-dimethoxyphenyl group, 2,6-dimethoxyphenyl group, 3,4-dimethoxyphenyl group, 3,5-dimethoxyphenyl group, 3,5- diethoxyphenyl group, 3,5-di-n-buthoxyphenyl group, 2-methoxy-4-ethoxyphenyl group, 2-methoxy-6-ethoxyphenyl group, 3,4,5-trimethoxyphenyl group, 4-phenylphenyl group, 3-phenylphenyl group, 2-phenylphenyl group, 4-(4'-methyl phenyl)phenyl group, 4-(3'-methylphenyl)phenyl group, 4-(4'-methoxyphenyl)phenyl group, 4-(4'-n-buthoxyphenyl)phenyl group, 2-(2'-methoxyphenyl)phenyl group, 4-(4'-chlorophenyl)phenyl group, 3-methyl-4-phenylphenyl group, 3-methoxy-4-phenylphenyl group,
4-fluorophenyl group, 3-fluorophenyl group, 2-fluorophenyl group, 4-chlorophenyl group, 3-chlorophenyl group, 2-chlorophenyl group, 4-bromophenyl group, 2-bromophenyl group, 4-chloro-1-naphthyl group, 4-chloro-2-naphthyl group, 6-bromo-2-naphthyl group, 2,3-difluorophenyl group, 2,4-difluorophenyl group, 2,5-difluorophenyl group, 2,6-difluorophenyl group, 3,4-difluorophenyl group, 3,5-difluorophenyl group, 2,3-dichlolrophenyl group, 2,4-dichlorophenyl group, 2,5-dichlorophenhyl group, 3,4-dichlorophenyl group, 3,5-dichlorophenyl group, 2,5-dibromophenyl group, 2,4,6-trichlorophenyl group, 2,4-dichloro-1-naphthyl group, 1,6-dichloro-2-naphthyl group, 2-fluoro-4-methylphenyl group, 2-fluoro-5-methylphenyl group, 3-fluoro-2-methylphenyl group, 3-fluoro-4-methylphenyl group, 2-methyl-4-fluorophenyl group, 2-methyl-5-fluorophenyl group, 3-methyl-4-fluorophenyl group, 2-chloro-4-methylphenyl group, 2-chloro-5-methylphenyl group, 2-chloro-6-methylphenyl group, 2-methyl-3-chlorophenyl group, 2-methyl-4-chlorophenyl group, 3-methyl-4-chlorophenyl group, 2-chloro-4,6-dimethylphenyl group, 2-methoxy-4-fluorophenyl group, 2-fluoro-4-methoxyphenyl group, 2-fluoro-4-ethoxyphenyl group, 2-fluoro-6-methoxy phenyl group, 3-fluoro-4-ethoxyphenyl group, 3-chloro-4-methoxy phenyl group, 2-methoxy-5-chlorophenyl group, 3-methoxy 6-chlorophenyl group and 5-chloro-2,4-dimethoxy phenyl group.

In the compound shown by the formula (9), $B_1$ and $B_2$ are a hydrogen atom, a linear, branched or cyclic aryl group, a substituted or unsubstituted aryl group or a substituted or unsubstituted aralkyl group. Preferably, $B_1$ and $B_1$ are a hydrogen atom, a linear, branched or cyclic alkyl group having 1 to 16 carbon atoms, a substituted or unsubstituted aryl group having 4 to 16 carbon atoms or a substituted or unsubstituted aralkyl group having 5 to 16 carbon atoms. More preferably, B1 and B2 are a hydrogen atom, a linear, branched or cyclic alkyl group having 1 to 8 carbon atoms, a substituted or unsubstituted aryl group having 6 to 12 carbon atoms or a substituted or unsubstituted aralkyl group having 7 to 12 carbon atoms. Further preferably, B1 and B2 are a linear, branched or cyclic alkyl group having 1 to 8 carbon atoms, a carbocyclic aromatic group having 6 to 10 carbon atoms or a carbocyclic aralkyl group having 7 to 10 carbon atoms.

Specific examples of the substituted or unsubstituted aryl group shown by $B_1$ and $B_2$, the substituted or unsubstituted aryl groups exemplified as specific examples of $Ar_1$ and $Ar_2$ can be given, for example. Specific examples of the linear, branched or cyclic alkyl group shown by $B_1$ and $B_2$ include, though not limited thereto, a methyl group, ethyl group, n-propyl group, isopropyl group, n-butyl group, isobutyl group, sec-butyl group, tert-butyl group, n-pentyl group, isopentyl group, neopentyl group, tert-pentyl group, cyclopentyl group, n-hexyl group, 2-ethylbutyl group, 3,3-dimethylbutyl group, cyclohexyl group, n-heptyl group, cyclohexylmethyl group, n-octyl group, tert-octyl group, 2-ethylhexyl group, n-nonyl group, n-decyl group, n-dodecyl group, n-tetradecyl group and n-hexadecyl group, for example.

Specific examples of the substituted or unsubstituted aralkyl group shown by $B_1$ and $B_2$ include, though not limited thereto, aralkyl groups such as a benzyl group, phenetyl group, α-methylbenzyl group, α,α-dimethylbenzyl group, 1-naphthylmethyl group, 2-naphthylmethyl group, furfuryl group, 2-methylbenzyl group, 3-methylbenzyl group, 4-methylbenzyl group, 4-ethylbenzyl group, 4-isopropylbenzyl group, 4-tert-butylbenzyl group, 4-n-hexylbenzyl group, 4-nonylbenzyl group, 3,4-dimethylbenzyl group, 3-methoxybenzyl group, 4-methoxybenzyl group, 4-ethoxybenzyl group, 4-n-buthoxybenzyl group, 4-n-hexyloxybenzyl group, 4-nonyloxybenzyl group, 4-fluorobenzyl group, 3-fluorobenzyl group, 2-cholorobenzyl group and 4-chlorobenzyl group.

$Z_1$ and $Z_2$ are a hydrogen atom, a halogen atom, a liner, branched or cyclic alkyl group, a linear, branched or cylic alkoxy group or a substituted or unsubstiuted aryl group. Preferably, $Z_1$ and $Z_2$ are a hydrogen atom, a linear, branched or cyclic alkyl group having 1 to 16 carbon atoms, a halogen atom, a linear, branched or cyclic alkoxy group having 1 to 16 carbon atoms, or a substituted or unsubstituted aryl group having 4 to 20 carbon atoms. More preferably, $Z_1$ and $Z_2$ are a hydrogen atom, a halogen atom, a linear, branched or cyclic alkyl group having 1 to 8 carbon atoms, a linear, branched or cyclic alkoxy group having 1 to 8 carbon atoms, or a substituted or unsubstituted aryl group having 6 to 12 carbon atoms. Further preferably, $Z_1$ and $Z_2$ are a hydrogen atom.

Specific examples of the substituted or unsubstituted alkyl group shown by $Z_1$ and $Z_2$, the linear, branched or cyclic alkyl groups exemplified as specific examples of $B_1$ and $B_2$ can be given, for example. Specific examples of the substituted or unsubstituted aryl group shown by $Z_1$ and $Z_2$, the substituted or substituted aryl groups exemplified as specific examples of $Ar^{21'}$ and $Ar^{22'}$ can be given, for example.

Specific examples of the halogen atom and the linear, branched or cyclic alkoxy group shown by $Z_1$ and $Z_2$ include halogen atoms such as a fluorine atom, chlorine atom and bromine atom, and alkoxy groups such as a methoxy group, ethoxy group, n-propoxy group, isopropoxy group, n-butoxy group, isobutoxy group, sec-butoxy group, n-pentyloxy group, isopentyloxy group, neopentyloxy group, cyclopentyloxy group, n-hexyloxy group, 2-ethylbuthoxy group, 3,3-dimethylbuthoxy group, cyclohexyloxy group, n-heptyloxy group, a cyclohexylmethyloxy group, n-octyloxy group, 2-ethylhexyloxy group, n-nonyloxy group, n-decycloxy group, n-dodecyloxy group, n-tetra-decyloxy group and n-hexadecyloxy group.

As specific examples of compound shown by the formula (9), following compounds (numbers 1 to 100) can be given, for example. However, the invention is not limited to these.
Exemplary Compounds
1. 7-(N'-carbazoyl)-N,N-diphenyl-9H-fluorene-2-amine
2. 7-(N'-carbazoyl)-N-phenyl-N-(4'-methylphenyl)-9-methyl-9H-fluorene-2-amine
3. 7-(N'-carbazoyl)-N,N-diphenyl-9,9-dimethyl-9H-fluorene-2-amine
4. 7-(N'-carbazoyl)-N-phenyl-N-(3'-methylphenyl)-9,9-dimethyl-9H-fluorene-2-amine
5. 7-(N'-carbazoyl)-N-phenyl-N-(4'-methylphenyl)-9,9-dimethyl-9H-fluorene-2-amine
6. 7-(N'-carbazoyl)-N-phenyl-N-(4'-ethylphenyl)-9,9-dimethyl-9H-fluorene-2-amine
7. 7-(N'-carbazoyl)-N-phenyl-N-(4'-tert-butylphenyl)-9,9-dimethyl-9H-fluorene-2-amine
8. 7-(N'-carbazoyl)-N-phenyl-N-(3',4'-dimethylphenyl)-9,9-dimethyl-9H-fluorene-2-amine
9. 7-(N'-carbazoyl)-N-phenyl-N-(3',5'-dimethylphenyl)-9,9-dimethyl-9H-fluorene-2-amine
10. 7-(N'-carbazoyl)-N,N-di(3'-methylphenyl)-9,9-dimethyl-9H-fluorene-2-amine 11. 7-(N'-carbazoyl)-N,N-di(4'-methylphenyl)-9,9-dimethyl-9H-fluorene-2-amine
12. 7-(N'-carbazoyl)-N,N-di(4'-ethylphenyl)-9,9-dimethyl-9H-fluorene-2-amine
13. 7-(N'-carbazoyl)-N-phenyl-N-(3'-methoxyphenyl)-9,9-dimethyl-9H-fluorene-2-amine
14. 7-(N'-carbazoyl)-N-phenyl-N-(4'-methoxyphenyl)-9,9-dimethyl-9H-fluorene-2-amine
15. 7-(N'-carbazoyl)-N-phenyl-N-(4'-ethoxyphenyl)-9,9-dimethyl-9H-fluorene-2-amine
16. 7-(N'-carbazoyl)-N-phenyl-N-(4'-n-butoxyphenyl)-9,9-dimethyl-9H-fluorene-2-amine
17. 7-(N'-carbazoyl)-N,N-di(4'-methoxyphenyl)-9,9-dimethyl-9H-fluorene-2-amine
18. 7-(N'-carbazoyl)-N-(3'-methylphenyl)-N-(4''-methoxyphenyl)-9,9-dimethyl-9H-fluorene-2-amine
19. 7-(N'-carbazoyl)-N-(4'-methylphenyl)-N-(4''-methoxyphenyl)-9,9-dimethyl-9H-fluorene-2-amine
20. 7-(N'-carbazoyl)-N-phenyl-N-(3'-fluorophenyl)-9,9-dimethyl-9H-fluorene-2-amine
21. 7-(N'-carbazoyl)-N-phenyl-N-(4'-chlorophenyl)-9,9-dimethyl-9H-fluorene-2-amine
22. 7-(N'-carbazoyl)-N-phenyl-N-(4'-phenylphenyl)-9,9-dimethyl-9H-fluorene-2-amine
23. 7-(N'-carbazoyl)-N-phenyl-N-(1-naphthylphenyl)-9,9-dimethyl-9H-fluorene-2-amine
24. 7-(N'-carbazoyl)-N-phenyl-N-(2'-naphthyl)-9,9-dimethyl-9H-fluorene-2-amine
25. 7-(N'-carbazoyl)-N-(4'-methylphenyl)-N-(2''-naphthyl)-9,9-dimethyl-9H-fluorene-2-amine
26. 7-(N'-carbazoyl)-N-phenyl-N-(2'-furyl)-9,9-dimethyl-9H-fluorene-2-amine
27. 7-(N'-carbazoyl)-N-phenyl-N-(2'-thienyl)-9,9-dimethyl-9H-fluorene-2-amine
28. 7-(N'-carbazoyl)-N,N-diphenyl-4-fluoro-9,9-dimethyl-9H-fluorene-2-amine
29. 7-(N'-carbazoyl)-N,N-diphenyl-3-methoxy-9,9-dimethyl-9H-fluorene-2-amine
30. 7-(N'-carbazoyl)-N,N-diphenyl-4-phenyl-9,9-dimethyl-9H-fluorene-2-amine
31. 7-(3'-methyl-N'-carbazoyl)-N,N-diphenyl-9,9-dimethyl-9H-fluorene-2-amine
32. 7-(3'-methoxy-N'-carbazoyl)-N,N-diphenyl-9,9-dimethyl-9H-fluorene-2-amine
33. 7-(3'-chloro-N'-carbazoyl)-N,N-diphenyl-9,9-dimethyl-9H-fluorene-2-amine
34. 2,7-di(N-carbazoyl)-9,9-dimethyl-9H-fluorene-2-amine
35. 7-(N'-phenoxazyl)-N,N-diphenyl-9,9-dimethyl-9H-fluorene-2-amine
36. 7-(N'-phenoxazyl)-N,N-di(4'-methylphenyl)-9,9-dimethyl-9H-fluorene-amine
37. 2,7-di(N-phenoxazyl)-9,9-dimethyl-9H-fluorene
38. 7-(N'-phenothiazyl)-N,N-diphenyl-9,9-dimethyl-9H-fluorene-2-amine
39. 7-(N'-phenothiazyl)-N-phenyl-N-(3'-methylphenyl)-9,9-dimethyl-9H-fluorene-2-amine
40. 7-(N'-phenothiazyl)-N-phenyl-N-(4'-methylphenyl)-9,9-dimethyl-9H-fluorene-2-amine
41. 7-(N'-phenothiazyl)-N,N-di(4'-methylphenyl)-9,9-dimethyl-9H-fluorene-2-amine
42. 7-(N'-phenothiazyl)-N-phenyl-N-(4'-methoxyphenyl)-9,9-dimethyl-9H-fluorene-2-amine
43. 7-(N'-phenothiazyl)-N-phenyl-N-(2'-naphthyl)-9,9-dimethyl-9H-fluorene-2-amine
44. 2,7-di(N-phenothiazyl)-9,9-dimethyl-9H-fluorene
45. 7-(N'-carbazoyl)-N,N-diphenyl-9,9-diethyl-9H-fluorene-2-amine
46. 7-(N'-carbazoyl)-N-phenyl-N-(4'-methylphenyl)-9,9-diethyl-9H-fluorene-2-amine
47. 7-(N'-carbazoyl)-N,N-di(4'-methylphenyl)-9,9-diethyl-9H-fluorene-2-amine
48. 7-(N'-carbazoyl)-N-phenyl-N-(3'-methoxyphenyl)-9,9-diethyl-9H-fluorene-2-amine
49. 7-(N'-carbazoyl)-N,N-diphenyl-4-methyl-9,9-diethyl-9H-fluorene-2-amine
50. 7-(N'-carbozoyl)-N,N-diphenyl-9-isopropyl-9H-fluorene-2-amine
51. 7-(N'-carbazoyl)-N,N-diphenyl-9,9-di-n-propyl-9H-fluorene-2-amine
52. 7-(N'-carbazoyl)-N-phenyl-N-(4'-methylphenyl)-9,9-di-n-propyl-9H-fluorene-2-amine
53. 7-(N'-carbazoyl)-N-phenyl-N-(4'-methoxyphenyl)-9,9-di-n-propyl-9H-fluorene-2-amine
54. 2,7-di(N-carbazoyl)-9,9-di-n-propyl-9H-fluorene
55. 2,7-di(N-phenoxazyl)-9,9-di-n-propyl-9H-fluorene
56. 7-(N'-carbazoyl)-N,N-diphenyl-9,9-di-n-butyl-9H-fluorene-2-amine
57. 7-(N'-carbazoyl)-N,N-di(4'-methylphenyl)-9,9-di-n-butyl-9H-fluorene-2-amine
58. 2,7-di(N'-carbazoyl)-9,9-di-n-butyl-9H-fluororene
59. 7-(N'-carbazoyl)-N-phenyl-N-(4'-methoxyphenyl)-9,9-di-n-pentyl-9H-fluorene-2-amine
60. 7-(N'-phenoxazyl)-N-phenyl-N-(3'-methoxyphenyl)-9,9-di-n-pentyl-9H-fluorene-2-amine
61. 7-(N'-carbazoyl)-N,N-di(4''-methoxyphenyl)-9,9-di-n-pentyl-9H-fluorene-2-amine
62. 2,7-di(N'-carbazoyl)-9,9-di-n-pentyl-9H-fluorene
63. 7-(N'-carbazoyl)-N,N-diphenyl-9,9-di-n-hexyl-9H-fluorene-2-amine
64. 7-(N'-carbazoyl)₇N,N-di(4'-methylphenyl)-9,9-di-n-hexyl-9H-fluorene-2-amine
65. 7-(N'-carbazoyl)-N,N-diphenyl-9-cyclohexyl-9H-fluorene-2-amine
66. 7-(N'-carbazoyl)-N,N-diphenyl-9,9-di-n-octyl-9H-fluorene-2-amine
67. 7-(N'-phenoxazyl)-N,N-di(4'-methylphenyl)-9,9-di-n-octyl-9H-fluorene-2-amine
68. 7-(N'-carbazoyl)-N,N-diphenyl-9-methyl-9-ethyl-9H-fluorene-2-amine
69. 7-(N'-carbazoyl)-N,N-diphenyl-9-methyl-9-n-propyl-9H-fluorene-2-amine
70. 7-(N'-phenothiazyl)-N,N-diphenyl-9-methyl-9-n-propyl-9H-fluorene-2-amine
71. 7-(N'-carbazoyl)-N,N-diphenyl-9-ethyl-9-n-hexyl-9H-fluorene-2-amine
72. 7-(N'-carbazoyl)-N,N-diphenyl-9-ethyl-9-cyclohexyl-9H-fluorene-2-amine
73. 7-(N'-carbazoyl)-N,N-diphenyl-9-benzyl-9H-fluorene-2-amine
74. 7-(N'-carbazoyl)-N,N-diphenyl-9,9-dibenzyl-9H-fluorene-2-amine
75. 7-(N'-carbazoyl)-N,N-diphenyl-9,9-di(4'-methylbenzyl)-9H-fluorene-2-amine
76. 7-(N'-carbazoyl)-N,N-diphenyl-9,9-di(4'-methoxybenzyl)-9H-fluorene-2-amine
77. 7-(N'-carbazoyl)-N-phenyl-N-(4'-methylphenyl)-9,9-dibenzyl-9H-fluorene-2-amine
78. 7-(N'-carbazoyl)-N,N-di(4'-methylphenyl)-9,9-dibenzyl-9H-fluorene-2-amine
79. 7-(N'-carbazoyl)-N-phenyl-N-(4'-methoxyphenyl)-9,9-dibenzyl-9H-fluorene-2-amine
80. 7-(N'-carbazoyl)-N-phenyl-N-(4'-phenylphenyl)-9,9-dibenzyl-9H-fluorene-2-amine 81. 7-(N'-carbazoyl)-N-phenyl-N-(2'-naphthyl)-9,9-dibenzyl-9H-fluorene-2-amine
82. 7-(N'-phenoxazyl)-N-phenyl-N-(4'-methylphenyl)-9,9-dibenzyl-9H-fluorene-2-amine
83. 7-(N'-phenothiazyl)-N,N-di(4'-methylphenyl)-9,9-dibenzyl-9H-fluorene-2-amine
84. 2,7-di(N-carbazoyl)-9,9-dibenzyl-9H-fluorene
85. 2,7-di(N-carbazoyl)-9,9-di(4'-methylbenzyl)-9H-fluorene
86. 2-(N-carbazoyl)-7-(N'-phenothiazyl)-9,9-dibenzyl-9H-fluorene
87. 7-(N'-carbazoyl)-N,N-diphenyl-9-methyl-9-benzyl-9H-fluorene-2-amine
88. 7-(N'-phenoxazyl)-N,N-diphenyl-9-ethyl-9-benzyl-9H-fluorene-2-amine
89. 7-(N'-carbazoyl)-N,N-diphenyl-9,9-diphenyl-9H-fluorene-2-amine
90. 7-(N'-carbazoyl)-N-phenyl-N-(4'-methylphenyl)-9,9-diphenyl-9H-fluorene-2-amine
91. 7-(N'-carbazoyl)-N,N-di(4'-methylphenyl)-9,9-diphenyl-9H-fluorene-2-amine
92. 7-(N'-carbazoyl)-N-phenyl-N-(3'-methylphenyl)-9,9-di(4''-methylphenyl)-9H-fluorene-2-amine
93. 7-(N'-carbazoyl)-N-phenyl-N-(3'-methylphenyl)-9,9-di(4''-methoxyphenyl)-9H-fluorene-2-amine
94. 7-(N'-phenoxazyl)-N,N-di(4'-methylphenyl)-9,9-diphenyl-9H-fluorene-2-amine
95. 7-(N'-phenothiazyl)-N,N-diphenyl-9,9-diphenyl-9H-fluorene-2-amine
96. 2,7-di(N'-carbazoyl)-9,9-di(4'-methylphenyl)-9H-fluorene
97. 2-(N-carbazoyl)-7-(N'-phenoxazyl)-9,9-diphenyl-9H-fluorene
98. 2-(N-phenoxazyl)-7-(N'-phenothiazyl)-9,9-diphenyl-9H-fluorene
99. 7-(N'-carbazoyl)-N-phenyl-N-(4'-methylphenyl)-9-methyl-9-phenyl-9H-fluorene-2-amine
100. 7-(N'-carbazoyl)-N,N-diphenyl-9-ethyl-9-phenyl-9H-fluorene-2-amine As the materials for the hole-injecting material and hole-transporting material, the above-mentioned substances can be used. The following can also be used: porphyrin compounds (disclosed in JP-A-63-295695 and others), aromatic tertiary amine compounds and styrylamine compounds (see U.S. Pat. No. 4,127,412, JP-A-53-27033, 54-58445, 55-79450, 55-144250, 56-119132, 61-295558, 61-98353 and 63-295695, and others). Aromatic tertiary amine compounds are particularly preferably used. The following can also be given as examples:
4,4'-bis(N-(1-naphthyl)-N-phenylamino)biphenyl (abbreviated by NPD, hereinafter), which has in the molecule thereof two fused aromatic rings, disclosed in U.S. Pat. No. 5,061,569, and 4,4',4''-tris(N-(3-methylphenyl)-N-phenylamino)triphenylamine (abbreviated by MTDATA, hereinafter) wherein three triphenylamine units are linked to each other in a star-burst form, disclosed in JP-A-H4-308688.

In addition to the aromatic dimethylidene type compounds mentioned above as the material for an emitting layer, inorganic compounds, p-type Si and p-type SiC can also be used as the material of the hole-injecting layer.

The hole-injecting/transporting layer can be formed from the above-mentioned compounds by a known method such as vacuum deposition, spin coating, casting or LB technique. The film thickness of the hole-injecting/transporting layer is not particularly limited, and is usually from 5 nm to 5 µm. The hole-injecting/transporting layer may be a single layer made of one, or two or more of the above-mentioned materials, or may be stacked hole-injecting/transporting layers made of different compounds, insofar as the compound of the invention is contained in the hole-transporting region.

Further, an organic semiconductor layer may be formed. The organic semiconductor layer is a layer for helping the injection of holes or electrons into the emitting layer, and is preferably a layer having an electric conductivity of $10^{-10}$ S/cm or more. As the material for the organic semiconductor layer, conductive oligomers such as an arylamine-containing oligomers such as those disclosed in JP-A-H8-193191, conductive dendorimers such as an arylamine-containing dendorimers, fullerene derivatives such as $C_{60}$, copper phthalocyanine (CuPc), $CF_x$, $MoO_3$ or the like can be used.

(Electron-Injecting/Transporting Layer)

The electron-injecting/transporting layer is a layer for helping the injection of electrons into the emitting layer, and has a large electron mobility. An adhesion-improving layer is one type of the electron-injecting layer which is formed of a material which exhibits excellent adhesion to the cathode.

In the invention, each of the electron-injecting layer and the electron-transporting layer may be formed of a plurality of layers The compound shown by the above formulas (3) and (4) used in the device configuration of the invention may form the electron-injecting/transporting layer alone, or may be used in the form of a mixture with other materials.

The material used in the electron-injecting/transporting layer is preferably a metal complex of 8-hydroxyquinoline or a derivative thereof. As specific examples of a metal complex of an 8-hydroxyquinoline or a derivative thereof, metal chelate oxynoid compounds including a chelate of oxine (generally, 8-quinolinol or 8-hydroxyquinoline) can be given.

For example, Alq described as the emitting material can be used for the electron-injecting layer.

An electron-transporting compound of the following formula can be given as the oxadiazole derivative.

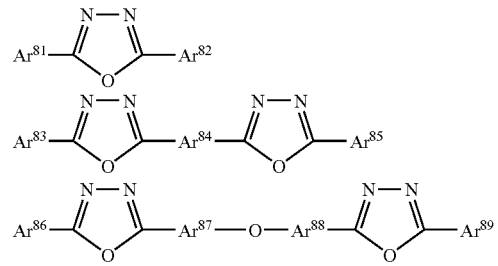

wherein $Ar^{81}$, $Ar^{82}$, $Ar^{83}$, $Ar^{85}$, $Ar^{86}$, and $Ar^{89}$ are independently a substituted or unsubstituted aryl group and may be the same or different. $Ar^{84}$, $Ar^{87}$, and $Ar^{88}$ are independently a substituted or unsubstituted arylene group and may be the same or different.

As examples of the aryl group, a phenyl group, a biphenyl group, an anthranyl group, a perylenyl group, and a pyrenyl group can be given. As examples of the arylene group, a phenylene group, a naphthylene group, a biphenylene group, an anthranylene group, a perylenylene group, a pyrenylene group, and the like can be given. As the substituent, an alkyl group having 1 to 10 carbon atoms, an alkoxy group having 1 to 10 carbon atoms, a cyano group, and the like can be given. The electron transporting compound is preferably one from which a thin film can be formed.

The following compounds can be given as specific examples of the electron transporting compound.

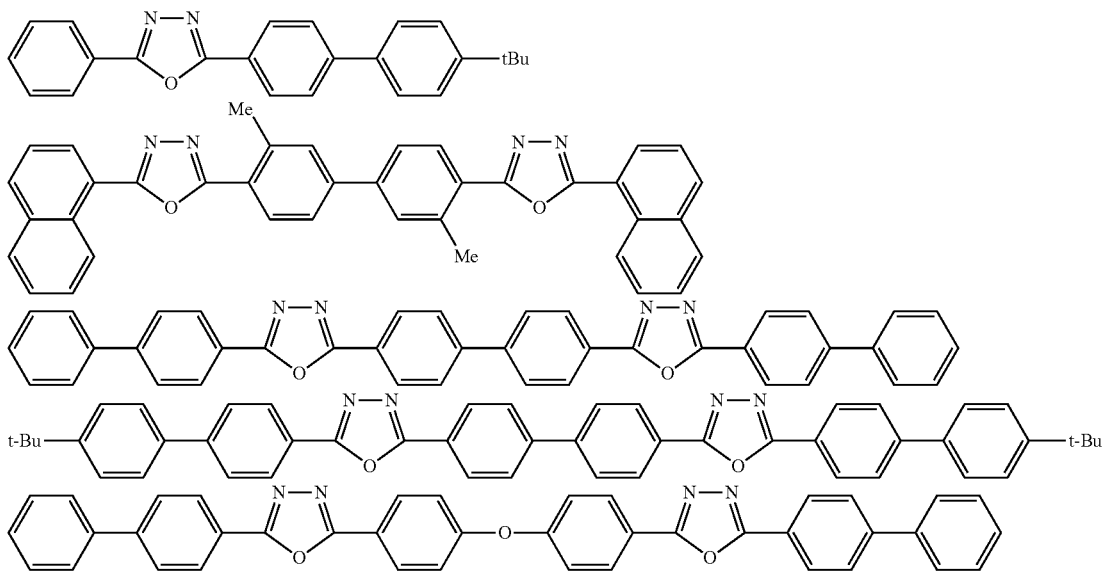

As the material used in the electron-injecting layer and the electron-transporting layer, compounds shown by the following formulas (C) to (G) can be used.

$$HAr\text{-}L^{14}\text{-}Ar^{24}\text{—}Ar^{25} \tag{C}$$

Nitrogen-containing heterocyclic derivatives represented by the formula (C) wherein HAr is a nitrogen-containing heterocycle with 3 to 40 carbon atoms which may have a substituent; $L^{14}$ is a single bond, an arylene group with 6 to 60 carbon atoms which may have a substituent, a heteroarylene group with 3 to 60 carbon atoms which may have a substituent or a fluorenylene group which may have a substituent; $Ar^{24}$ is a divalent aromatic hydrocarbon group with 6 to 60 carbon atoms which may have a substituent; and $Ar^{25}$ is an aryl group with 6 to 60 carbon atoms which may have a substituent or a heteroaryl group with 3 to 60 carbon atoms which may have a substituent.

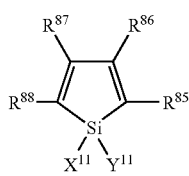 (D)

Silacyclopentadiene derivatives represented by the formula (D) wherein $X^{11}$ and $Y^{11}$ are independently a saturated or unsaturated hydrocarbon group having 1 to 6 carbon atoms, an alkoxy group, an alkenyloxy group, an alkynyloxy group, a hydroxyl group, a substituted or unsubstituted aryl group, or a substituted or unsubstituted hetero ring, or $X^{11}$ and $Y^{11}$ are bonded to form a saturated or unsaturated ring, and $R^{85}$ to $R^{88}$ are independently hydrogen, halogen, a substituted or unsubstituted alkyl group having 1 to 6 carbon atoms, an alkoxy group, an aryloxy group, a perfluoroalkyl group, a perfluoroalkoxy group, an amino group, an alkylcarbonyl group, an arylcarbonyl group, an alkoxycarbonyl group, an aryloxycarbonyl group, an azo group, an alkylcarbonyloxy group, an arylcarbonyloxy group, an alkoxycarbonyloxy group, an aryloxycarbonyloxy group, a sulfinyl group, a sulfonyl group, a sulfonyl group, a silyl group, a carbamoyl group, an aryl group, a heterocyclic group, an alkenyl group, an alkynyl group, a nitro group, a formyl group, a nitroso group, a formyloxy group, an isocyano group, a cyanate group, an isocyanate group, a thiocyanate group, an isothiocyanate group, or a cyano group, or adjacent groups of $R^{85}$ to $R^{88}$ from a substituted or unsubstituted fused ring.

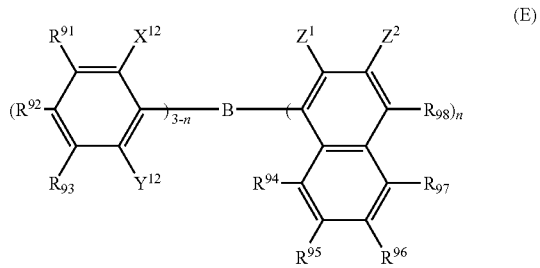 (E)

Borane derivatives represented by the formula (E) wherein $R^{91}$ to $R^{98}$ and $Z^2$ are independently a hydrogen atom, a saturated or unsaturated hydrocarbon group, an aromatic group, a heterocyclic group, a substituted amino group, a substituted boryl group, an alkoxy group, or an aryloxy group, $X^{12}$, $Y^{12}$, and $Z^1$ are independently a saturated or unsaturated hydrocarbon group, an aromatic group, a heterocyclic group, a substituted amino group, an alkoxy group, or an aryloxy group, the substituents for $Z^1$ and $Z^2$ may be bonded to form a fused ring, n is an integer of 1 to 3, provided that the $Z^1$'s may differ when n is 2 or more, and a case in which n is 1, $X^{12}$, $Y^{12}$, and $R^{92}$ are methyl groups, and $R^{98}$ is a hydrogen atom or a substituted boryl group, and a case in which n is 3 and $Z^1$ is a methyl group are excluded.

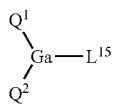 (F)

wherein Q¹ and Q² are independently ligands represented by the following formula (G) and L¹⁵ is a halogen atom, a substituted or unsubstituted alkyl group, a substituted or unsubstituted cycloalkyl group, a substituted or unsubstituted aryl group, a substituted or unsubstituted heterocyclic group, —OR' (R' is a hydrogen atom, a substituted or unsubstituted alkyl group, a substituted or unsubstituted cycloalkyl group, a substituted or unsubstituted aryl group, or a substituted or unsubstituted heterocyclic group) or a ligand represented by —O—Ga-Q³(Q⁴)(Q³ and Q⁴ have the same meanings as Q¹ and Q²).

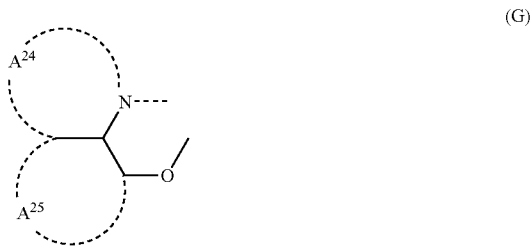

(G)

wherein rings $A^{24}$ and $A^{25}$ are fused a 6-membered aryl ring structures which may have a substituent.

The metal complexes have the strong nature of an n-type semiconductor and large ability of injecting electrons. Further the energy generated at the time of forming a complex is small so that a metal is then strongly bonded to ligands in the complex formed and the fluorescent quantum efficiency becomes large as the emitting material.

Specific examples of the substituents for the rings $A^{24}$ and $A^{25}$ forming the ligand of the above formula (G) include halogen atoms such as chlorine, bromine, iodine, and fluorine, substituted or unsubstituted alkyl groups such as a methyl group, ethyl group, propyl group, butyl group, sec-butyl group, tert-butyl group, pentyl group, hexyl group, heptyl group, octyl group, stearyl group, and trichloromethyl group, substituted or unsubstituted aryl groups such as a phenyl group, naphthyl group, 3-methylphenyl group, 3-methoxyphenyl group, 3-fluorophenyl group, 3-trichloromethylphenyl group, 3-trifluoromethylphenyl group, and 3-nitrophenyl group, substituted or unsubstituted alkoxy groups such as a methoxy group, n-butoxy group, tert-butoxy group, trichloromethoxy group, trifluoroethoxy group, pentafluoropropoxy group, 2,2,3,3-tetrafluoropropoxy group, 1,1,1,3,3,3-hexafluoro-2-propoxy group, and 6-(perfluoroethyl)hexyloxy group, substituted or unsubstituted aryloxy groups such as a phenoxy group, p-nitrophenoxy group, p-tert-butylphenoxy group, 3-fluorophenoxy group, pentafluorophenyl group, and 3-trifluoromethylphenoxy group, substituted or unsubstituted alkylthio groups such as a methylthio group, ethylthio group, tert-butylthio group, hexylthio group, octylthio group, and trifluoromethylthio group, substituted or unsubstituted arylthio groups such as a phenylthio group, p-nitrophenylthio group, p-tert-butylphenylthio group, 3-fluorophenylthio group, pentafluorophenylthio group, and 3-trifluoromethylphenylthio group, a cyano group, a nitro group, an amino group, mono- or di-substituted amino groups such as a methylamino group, diethylamino group, ethylamino group, diethylamino group, dipropylamino group, dibutylamino group, and diphenylamino group, acylamino groups such as a bis(acetoxymethyl)amino group, bis(acetoxyethyl)amino group, bis(acetoxypropyl) amino group, and bis(acetoxybutyl)amino group, a hydroxyl group, a siloxy group, an acyl group, substituted or unsubstituted carbamoyl groups such as a carbamoyl group, a methylcarbamoyl group, dimethylcarbamoyl group, ethylcarbamoyl group, diethylcarbamoyl group, propylcarbamoyl group, butylcarbamoyl group, and phenylcarbamoyl group, a carboxylic acid group, a sulfonic acid group, an imido group, cycloalkyl groups such as a cyclopentane group and a cyclohexyl group, aryl groups such as a phenyl group, naphthyl group, biphenyl group, anthryl group, phenanthryl group, fluorenyl group, and pyrenyl group, heterocyclic groups such as a pyridinyl group, pyrazinyl group, pyrimidinyl group, pyridazinyl group, triazinyl group, indolinyl group, quinolinyl group, acridinyl group, pyrrolidinyl group, dioxanyl group, piperidinyl group, morpholidinyl group, piperazinyl group, triazinyl group, carbazolyl group, furanyl group, thiophenyl group, oxazolyl group, oxadiazolyl group, benzooxazolyl group, thiazolyl group, thiadiazolyl group, benzothiazolyl group, triazolyl group, imidazolyl group, and benzimidazolyl group, and the like. The above substituents may be bonded to form a six-membered aryl ring or heterocyclic ring.

Polymer compounds containing a nitrogen-containing heterocyclic group or nitrogen-containing heterocyclic derivative may be used.

In addition to the above-mentioned compounds, the electron-injecting layer or the electron-transporting layer may contain phosphine oxide compounds (JP-A-2004-203828) or phenanthroline derivatives (JP-A-H05-331459, JP-A-H07-82551, JP-A-H10-79297, JP-A-2001-267080, JP-A-20001-131174).

A preferred embodiment of the invention is a device containing a reducing dopant in an electron-transferring region or in an interfacial region between the cathode and the organic layer. The reducing dopant is defined as a substance which can reduce an electron-transferring compound. Accordingly, various substances which have given reducing properties can be used. For example, at least one substance can be preferably used which is selected from the group consisting of alkali metals, alkaline earth metals, rare earth metals, alkali metal oxides, alkali metal halides, alkaline earth metal oxides, alkaline earth metal halides, rare earth metal oxides, rare earth metal halides, alkali metal organic complexes, alkaline earth metal organic complexes, and rare earth metal organic complexes.

More specific examples of the preferred reducing dopants include at least one alkali metal selected from the group consisting of Na (work function: 2.36 eV), K (work function: 2.28 eV), Rb (work function: 2.16 eV) and Cs (work-function: 1.95 eV), and at least one alkaline earth metal selected from the group consisting of Ca (work function: 2.9 eV), Sr (work function: 2.0 to 2.5 eV), and Ba (work function: 2.52 eV). Metals having a work function of 2.9 eV or less are particularly preferred. Among these, a more preferable reducing dopant is at least one alkali metal selected from the group consisting of K, $R^b$ and Cs. Even more preferable is Rb or Cs. Most preferable is Cs. These alkali metals are particularly high in reducing ability. Thus, the addition of a relatively small amount thereof to an electron-injecting zone improves the luminance of the organic EL device and make the lifetime thereof long. As a reducing dopant having a work function of 2.9 eV or less, combinations of two or more alkali metals are preferable, and particularly combinations including Cs, such as Cs and Na, Cs and K, Cs and Rb, or Cs, Na and K are preferable. The combination containing Cs makes it possible to exhibit the reducing ability efficiently. The luminance of the organic EL device can be improved and the lifetime thereof can be made long by the addition thereof to its electron-injecting zone.

In the invention, an electron-injecting layer made of an insulator or a semiconductor may further be provided between a cathode and an organic layer. By forming the electron-injecting layer, a current leakage can be effectively prevented and electron-injecting properties can be improved. As the insulator, at least one metal compound selected from the group consisting of alkali metal calcogenides, alkaline earth metal calcogenides, halides of alkali metals and halides of alkaline earth metals can be preferably used. When the electron-injecting layer is formed of the alkali metal calcogenide or the like, the injection of electrons can be preferably further improved.

Specifically preferable alkali metal calcogenides include $Li_2O$, LiO, $Na_2S$, $Na_2Se$ and NaO and preferable alkaline earth metal calcogenides include CaO, BaO, SrO, BeO, BaS and CaSe. Preferable halides of alkali metals include LiF, NaF, KF, LiCl, KCl and NaCl. Preferable halides of alkaline earth metals include fluorides such as $CaF_2$, $BaF_2$, $SrF_2$, $MgF_2$ and $BeF_2$ and the other halides corresponding to the fluorides.

Semiconductors forming an electron-transporting layer include one or combinations of two or more of oxides, nitrides, and oxidized nitrides containing at least one element of Ba, Ca, Sr, Yb, Al, Ga, In, Li, Na, Cd, Mg, Si, Ta, Sb and Zn. An inorganic compound forming an electron-transporting layer is preferably a microcrystalline or amorphous insulating thin film: When the electron-transporting layer is formed of the insulating thin films, more uniformed thin film is formed whereby pixel defects such as a dark spot are decreased. Examples of such an inorganic compound include the above-mentioned alkali metal calcogenides, alkaline earth metal calcogenides, halides of alkali metals, and halides of alkaline earth metals.

(Cathode)

For the cathode, the following may be used: an electrode substance made of a metal, an alloy or an electroconductive compound, or a mixture thereof which has a small work function (4 eV or less). Specific examples of the electrode substance include sodium, sodium-potassium alloy, magnesium, lithium, magnesium/silver alloy, aluminum/aluminum oxide, aluminum/lithium alloy, indium, and rare earth metals.

This cathode can be formed by making the electrode substances into a thin film by vapor deposition, sputtering or some other method.

In the case where light is emitted from the emitting layer through the cathode, the cathode preferably has a light transmittance of larger than 10%.

The sheet resistance of the cathode is preferably several hundreds Ω/□ or less, and the film thickness thereof is usually from 5 nm to 1 μm, preferably from 5 to 200 nm.

By adjusting the thickness of the above-mentioned material, the cathode can be used as a semi-transparent and semi-light reflecting electrode.

(Insulating Layer)

In the organic EL device, pixel defects based on leakage or a short circuit are easily generated since an electric field is applied to the ultrathin film. In order to prevent this, it is preferred to insert an insulative thin layer between the pair of electrodes.

Examples of the material used in the insulating layer include aluminum oxide, lithium fluoride, lithium oxide, cesium fluoride, cesium oxide, magnesium oxide, magnesium fluoride, calcium oxide, calcium fluoride, cesium fluoride, cesium carbonate, aluminum nitride, titanium oxide, silicon oxide, germanium oxide, silicon nitride, boron nitride, molybdenum oxide, ruthenium oxide, and vanadium oxide. A mixture or laminate thereof may be used.

(Example of Fabricating Organic EL Device)

The organic EL device can be fabricated by forming an anode, an emitting layer, optionally a hole-injecting layer, optionally an electron-injecting layer, and further forming a cathode using the materials and methods exemplified above. The organic EL device can be fabricated in the order reverse to the above, i.e., the order from a cathode to an anode.

An example of the fabrication of the organic EL device will be described below which has a structure wherein the following are successively formed on a transparent substrate: anode/hole-injecting layer/hole-transporting layer/emitting layer/electron-transporting layer/cathode.

First, a thin film made of an anode material is formed in a thickness of 1 μm or less, preferably 10 to 200 nm on an appropriate transparent substrate by vapor deposition, sputtering or some other method, thereby forming an anode.

Next, a hole-transporting layer is formed on this anode. As described above, the hole-transporting layer can be formed by vacuum vapor deposition, spin coating, casting, LB technique, or some other method. Vacuum vapor deposition is preferred since a homogenous film is easily obtained and pinholes are not easily generated. In the case where the hole-injecting layer is formed by vacuum deposition, conditions for the deposition vary depending upon a compound used (a material for the hole-injecting layer), a desired crystal structure or recombining structure of the hole-injecting layer, and others. In general, the conditions are preferably selected from the following: deposition source temperature of 50 to 450° C., vacuum degree of $10^{-7}$ to $10^{-3}$ torr, vapor deposition rate of 0.01 to 50 nm/second, substrate temperature of −50 to 300° C., and film thickness of 5 nm to 5 μm.

On this hole-injecting layer, the hole-transporting layer formed of the compound shown by the above formula (1) and/or the above formula (2) is formed. The method or conditions for forming the layer are the same as those for forming the hole-injecting layer.

Next, an emitting layer is formed on the hole-transporting layer. The emitting layer can also be formed by making a desired organic luminescent material into a thin film by vacuum vapor deposition, sputtering, spin coating, casting or some other method. Vacuum vapor deposition is preferred since a homogenous film is easily obtained and pinholes are not easily generated. In the case where the emitting layer is formed by vacuum vapor deposition, conditions for the deposition, which vary depending on a compound used, can be generally selected from conditions similar to those for the hole-transporting layer.

Subsequently, on this emitting layer, the electron-transporting layer formed of the compounds shown by the above formula (3) and/or the above formula (4) is provided. Like the hole-transporting layer and the emitting layer, the layer is preferably formed by vapor vacuum deposition because a homogenous film is required. Conditions for the deposition can be selected from conditions similar to those for the hole-transporting layer and the emitting layer.

Lastly, a cathode is stacked thereon to obtain an organic EL device.

The cathode is made of a metal, and vapor deposition or sputtering may be used. However, vapor vacuum deposition is preferred in order to protect underlying organic layers from being damaged when the cathode film is formed.

For the organic EL device fabrication that has been described above, it is preferred that the formation from the anode to the cathode is continuously carried out, using only one vacuuming operation.

The method for forming each of the layers in the organic EL device of the invention is not particularly limited. Conventional film-forming methods such as vacuum vapor deposition and spin coating which are known in the art can be used. For example, the organic thin film layer which contains the compounds shown by the above formula (1) and/or the above formula (2) used in the organic EL device of the invention can be formed by known methods such as the vacuum vapor deposition method, the molecular beam epitaxy (MBE) deposition method or coating methods in which a solution which is obtained by dissolving the compound in a solvent is applied by dipping, spin coating, casting, bar coating, roll coating or the like.

The film thickness of each of the organic layers in the organic EL device of the invention is not particularly limited. In general, defects such as pinholes are easily generated when the film thickness is too small. Conversely, when the film thickness is too large, a high applied voltage becomes necessary, leading to a low efficiency. Usually, the film thickness is preferably in the range of several nanometers to one micrometer.

If a DC voltage is applied to the organic EL device, emission can be observed when the polarities of the anode and the cathode are positive and negative, respectively, and a voltage of 5 to 40 V is applied. When a voltage with an opposite polarity is applied, no electric current flows and hence, emission does not occur. If an AC voltage is applied, uniform emission can be observed only when the cathode and the anode have a positive polarity and a negative polarity, respectively. The waveform of the AC applied may be arbitrary.

EXAMPLES

The invention will be explained in detail with reference to Examples given below, which should not be construed as limiting the scope of the invention.

Examples will be explained below, but the invention is not limited to these Examples. The methods for evaluating organic EL devices are as follows.

(1) Initial performance:
A device was allowed to emit light by a DC current of 10 mA/cm². A voltage (V) which as applied at the time of emission and a luminous efficiency (L/J) was measured.

(2) Life:
A device was driven with a constant current at an initial luminance of 5000 cd/m². A life was determined as a half life (LT50) of luminance.

Compounds used in Examples 1 to 8, and Comparative Examples 1 to 3 were as follows.

Compound (HI1)

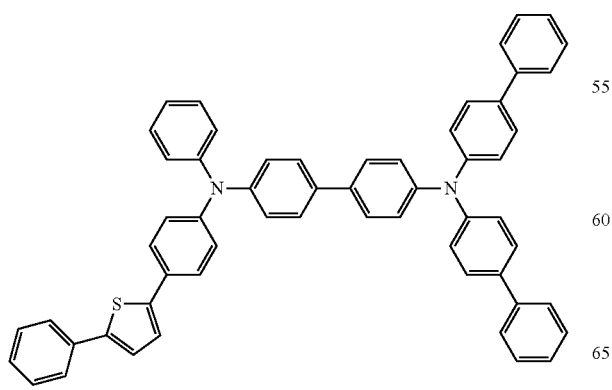

Compound (HI2)

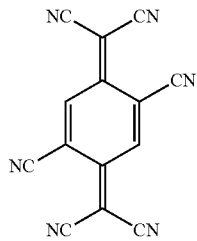

Compound (HT1)

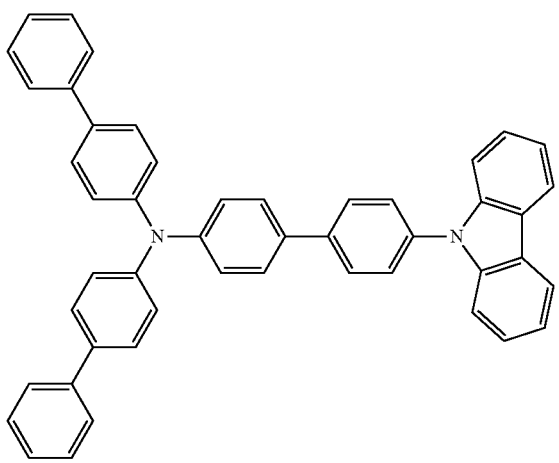

Compound (HT2)

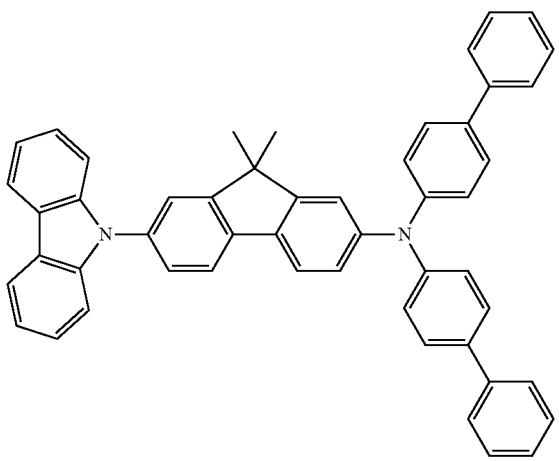

Compound (L1)

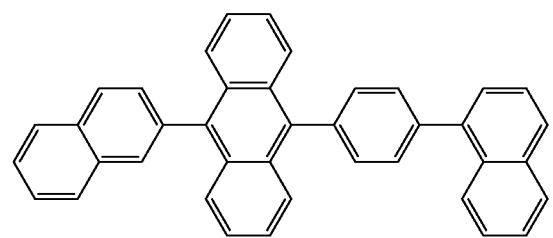

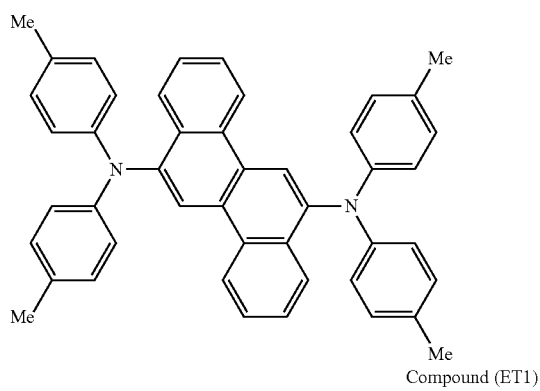

Compound (L2)

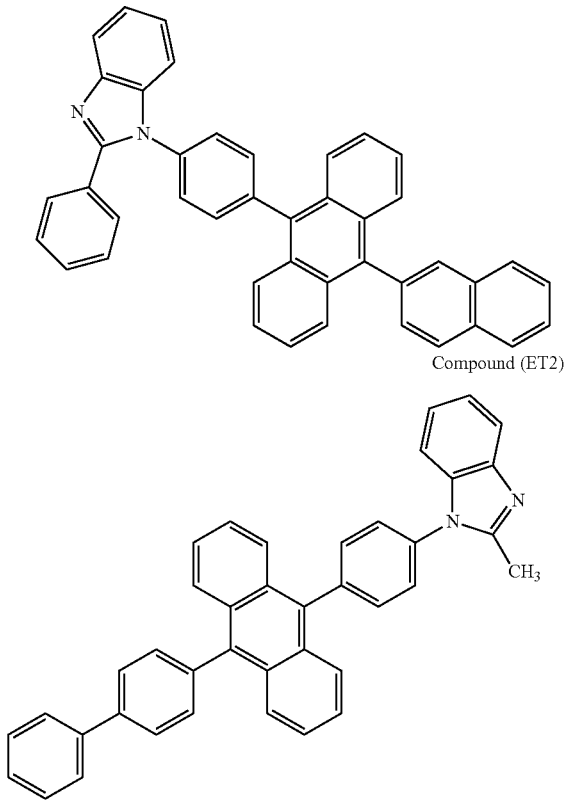

Compound (ET1)

Compound (ET2)

Example 1

A glass substrate of 25 mm by 75 mm by 1.1 mm thick with an ITO transparent electrode (GEOMATEC Co., LTD.) was subjected to ultrasonic cleaning with isopropyl alcohol for 5 minutes, and cleaned with ultraviolet rays and ozone for 30 minutes. The resultant substrate with transparent electrode lines was mounted on a substrate holder in a vacuum vapor deposition device. First, as a hole-injecting layer, compound HI1 film was formed into a film at a film-forming rate of 1 Å/s in a thickness of 10 nm so as to cover the surface of the transparence electrode on which the transparence electrode lines were formed. On the film of the compound H1, as a hole-transporting layer, a 35 nm-thick film of compound HT1 was formed at 1 Å/s.

Furthermore, on the film of the compound H1, compound L1 and compound L2 were formed into a 20 nm-thick film such that the thickness ratio became 18:2. This film functioned as a blue emitting layer. The film-forming rate was 1 Å/s and 0.11 Å/s, respectively.

On this film, as an electron-transporting layer, compound ET1 was formed into a 30 nm-thick film at a film-forming rate of 0.1 Å/s. After that, LiF was formed into a 0.5 nm-thick film at a film-forming rate of 0.1 Å/s. On the LiF film, metal Al was deposited in a thickness of 100 nm as a metal cathode at a film-forming rate of 1 Å/s, thereby fabricating an organic EL device.

Example 2

An organic EL device was fabricated in the same manner as in Example 1, except that compound HT2 was stacked in a film thickness of 35 nm as a hole-transporting layer.

Example 3

An organic EL device was fabricated in the same manner as in Example 1, except that compound ET2 was stacked in a film thickness of 30 nm as an electron-transporting layer.

Example 4

An organic EL device was fabricated in the same manner as in Example 1, except that compound HI2 was stacked in a film thickness of 5 nm as a hole-injecting layer, and compound HT2 was stacked in a film thickness of 40 nm as a hole-transporting layer.

Example 5

An organic EL device was fabricated in the same manner as in Example 1, except that $MoO_3$ was stacked in a film thickness of 3 nm as a hole-injecting layer, and compound HT2 was stacked in a film thickness of 42 nm as a hole-transporting layer.

Example 6

An organic EL device was fabricated in the same manner as in Example 1, except that $C_{60}$ was stacked in a film thickness of 3 nm as a hole-injecting layer, and compound HT2 was stacked in a film thickness of 42 nm as a hole-transporting layer.

Example 7

An organic EL device was fabricated in the same manner as in Example 1, except that PEDOT:PSS was stacked in a film thickness of 30 nm as a hole-injecting layer, and compound HT2 was stacked in a film thickness of 15 nm as a hole-transporting layer.

Example 8

An organic EL device was fabricated in the same manner as in Example 1, except that $CF_x$ was stacked in a film thickness of 3 nm as a hole-injecting layer, and compound HT2 was stacked in a film thickness of 42 nm as a hole-transporting layer.

Comparative Example 1

An organic EL device was fabricated in the same manner as in Example 1, except that 4,4'-bis[N(1-naphthyl)-N-phenylamino]biphenyl film (will be abbreviated as "NPD film" below) was stacked in a film thickness of 35 nm as a hole-transporting layer.

Comparative Example 2

An organic EL device was fabricated in the same manner as in Example 1, except that Alq (aluminum complex of 8-hydroxyquinoline) film was stacked in a film thickness of 30 nm as an electron-transporting layer.

Comparative Example 3

An organic EL device was fabricated in the same manner as in Example 1, except that N,N'-bis(N,N'-diphenyl-4-aminophenyl)-N,N-diphenyl-4,4'-diamino-1,1'-biphenyl film (will be abbreviated as "TPD232 film" below) was stacked in a film thickness of 10 nm as an electron-injecting layer.

For the fabricated organic EL devices in Examples and Comparative Examples, the half life of luminance and variation in driving voltage were measured. The results are shown in Table 1. It was confirmed from Table 1 that the organic EL devices in Examples 1 to 8 had a low driving voltage, high luminous efficiency and long half life of luminance.

TABLE 1

|  | Voltage (V) | Luminous efficiency (cd/A) | LT50 (hr) |
| --- | --- | --- | --- |
| Ex. 1 | 3.3 | 10.2 | 1360 |
| Ex. 2 | 3.4 | 9.8 | 1300 |
| Ex. 3 | 3.5 | 9.5 | 1520 |
| Ex. 4 | 3.3 | 8.2 | 1280 |
| Ex. 5 | 3.5 | 8.8 | 1420 |
| Ex. 6 | 3.8 | 7.9 | 1100 |
| Ex. 7 | 4.4 | 9 | 1190 |
| Ex. 8 | 3.7 | 9.2 | 1460 |
| Comp. Ex. 1 | 3.4 | 7.9 | 400 |
| Comp. Ex. 2 | 7.3 | 7.6 | 1200 |
| Comp. Ex. 3 | 6.1 | 8 | 570 |

Compounds used in Examples 9 to 11 and Comparative Examples 4 and 5 were as follows.

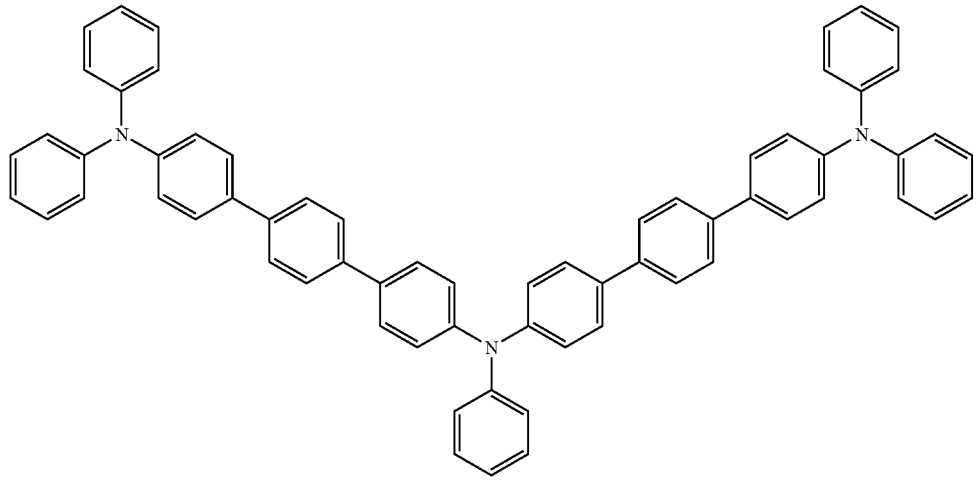

Compound (HI3)

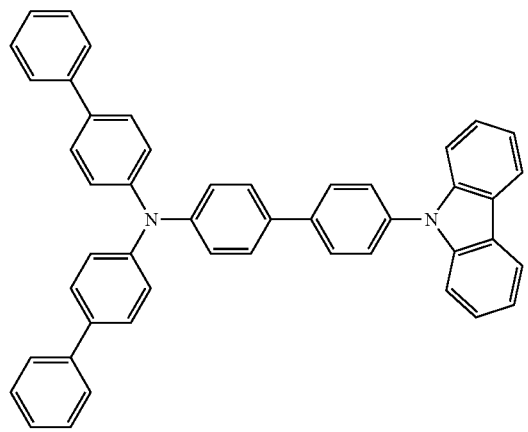

Compound (HT1)

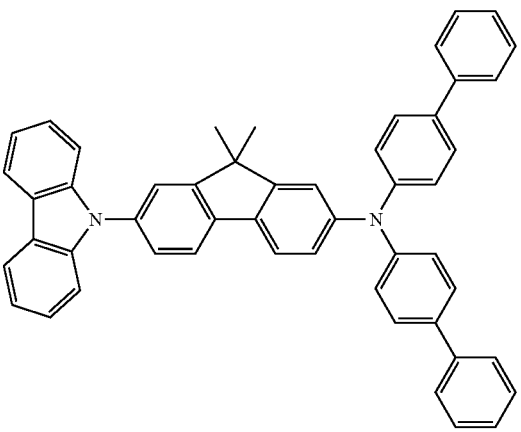

Compound (HT2)

-continued
Compound (L1)
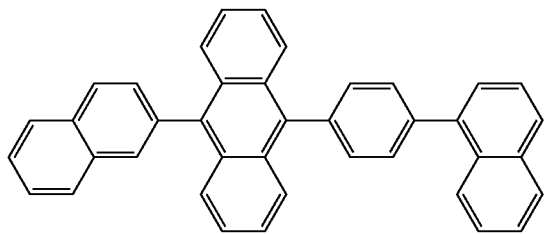
Compound (I2)
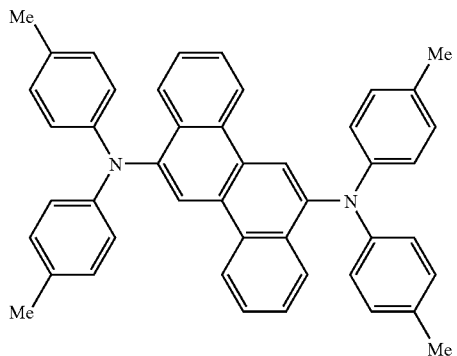
Compound (ET1)
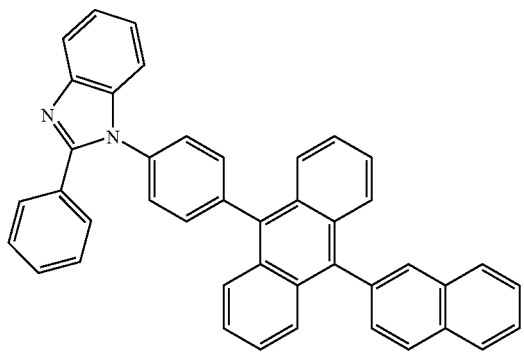
Compound (ET2)
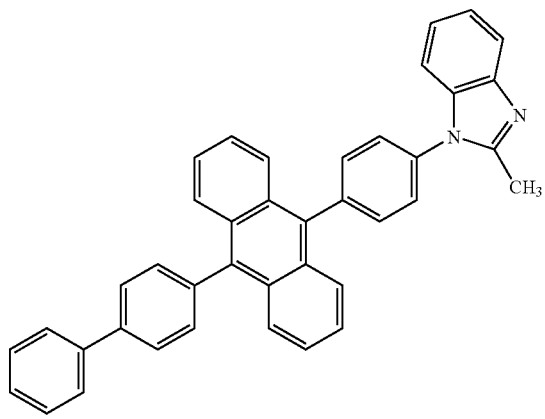
Compound (RD)
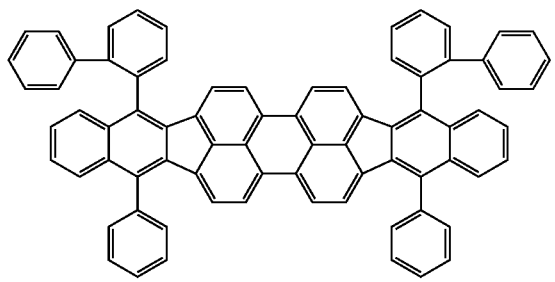
Compound (RH)
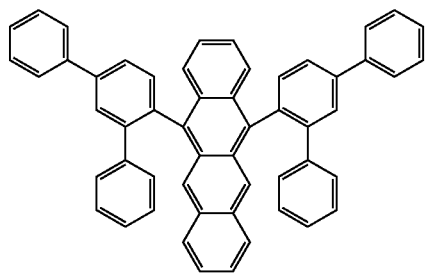
Compound (GD)
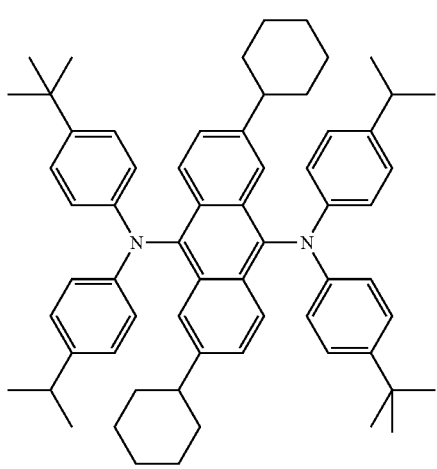

Example 9

A glass substrate of 25 mm by 75 mm by 1.1 mm thick with an ITO transparent electrode (anode) (GEOMATEC Co., LTD.) was subjected to ultrasonic cleaning with isopropyl alcohol for 5 minutes, and cleaned with ultraviolet rays and ozone for 30 minutes. The resultant substrate with transparent electrode lines was mounted on a substrate holder in a vacuum deposition device. First, as a hole-injecting layer, compound HI3 was formed into a film at a film-forming rate of 0.1 Å/s in a thickness of 10 nm so as to cover the surface of the transparence electrode on which the transparence electrode lines were formed. On this film of compound HI3, as a hole-transporting layer, a 25 nm-thick film of compound HT1 was formed at 1 Å/s.

Subsequent to formation of HT1 film, compound RH and compound RD were deposited in a thickness of 5 nm such that the amount of compound RD becomes 0.5 wt %. This film functioned as a first emitting layer. The first emitting layer emits red light. Then, as a charge blocking layer, a HT1 film was formed in a thickness of 5 nm. On the charge-blocking layer, compound L1 and compound L2 were deposited such that the amount of the compound L2 becomes 7.5 wt %. This functioned as a blue emitting layer (a second emitting layer) with a film thickness of 10 nm.

As a third emitting layer, compound L1 and compound GD were deposited in a thickness of 30 nm such that the amount of the compound GD becomes 10 wt % as a green emitting layer. On this film, as an electron-transporting layer, compound ET1 was formed into a 20 nm-thick film. Thereafter, an LiF film was formed in a thickness of 1.6 nm as an electron-injecting layer. Metal Al was deposited in a thickness of 150 nm as a metal cathode, thereby fabricating an organic EL device.

For the fabricated organic EL device, the initial performance and life were evaluated in the above-mentioned method.

In addition, when applying a voltage to the organic EL device obtained, the emitting color was white.

Example 10

An organic EL device was fabricated and evaluated in the same manner as in Example 9, except that compound HT2 was stacked in a film thickness of 25 nm as a hole-transporting layer, and compound HT2 was stacked in a film thickness of 5 nm as a charge-blocking layer.

A voltage was applied to the organic EL device obtained. The color of emitted light was white.

Example 11

An organic EL device was fabricated and evaluated in the same manner as in Example 10, except that compound ET2 was stacked in a film thickness of 20 nm as an electron-transporting layer.

A voltage was applied to the organic EL device obtained. The color of emitted light was white.

Comparative Example 4

An organic EL device was fabricated in the same manner as in Example 10, except that 4,4'-bis[N(1-naphthyl)-N-phenylamino]biphenyl film (will be abbreviated as "NPD film" below) was stacked in a film thickness of 25 nm as a hole-transporting layer, and NPD film was stacked in a film thickness of 5 nm as a charge-blocking layer.

Comparative Example 5

An organic EL device was fabricated in the same manner as in Example 10, except that 4,4'-bis[N(1-naphthyl)-N-phenylamino]biphenyl film (will be abbreviated to "NPD film" below) was stacked in a film thickness of 25 nm as a hole-transporting layer, and Alq (aluminum complex of 8-hydroxyquinoline) film was stacked in a film thickness of 20 nm as an electron-transporting layer.

TABLE 2

|  | Voltage (V) | Luminous efficiency (cd/A) | LT50 (hr) |
| --- | --- | --- | --- |
| Ex. 9 | 3.9 | 19.1 | 6800 |
| Ex. 10 | 3.8 | 19.6 | 7000 |
| Ex. 11 | 3.7 | 20.8 | 6500 |
| Comp. Ex. 4 | 3.7 | 19.5 | 3800 |
| Comp. Ex. 5 | 6.1 | 16.2 | 6000 |

INDUSTRIAL APPLICABILITY

The organic EL device of the invention can be used as organic EL materials for various colors including blue. The device can be used in fields such as various display devices, displays, back lights, light sources, signs, signboards, and interior lights, and is especially suitable as a display device for color displays.

The white light-emitting organic EL device of the invention has a high luminance, high efficiency and long life, and hence, it is significantly practical and usual as a full-color display, an information display, an in-vehicle display and an illuminator.

The documents described in the specification are incorporated herein by reference in its entirety.

The invention claimed is:

1. An organic electroluminescence device comprising:
   an anode,
   a cathode
   an emitting layer comprising an organic compound, which is between the anode and the cathode,
   two or more layers arranged in a hole injection and transport region which is between the anode and the emitting layer, and
   one or more layers arranged in an electron injection and transport region which is between the emitting layer and the cathode,
   wherein a layer in the hole injection and transport region, which is in contact with the emitting layer, comprises an aromatic amine derivative that has one carbazole skeleton,
   one of the layers other than the layer in contact with the emitting layer in the hole injection and transport region comprises an acceptor material that is an organic compound having a cyano group, and
   a layer in the electron injection and transport region comprises a benzimidazole derivative represented by the following formula (4):

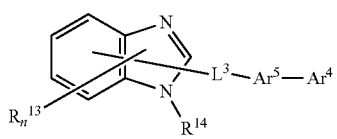

(4)

wherein Ar⁴ is a substituted fused ring group having 10 to 60 ring carbon atoms, Ar⁵ is a substituted or unsubstituted arylene group having 6 to 60 carbon atoms, L³ is a single bond, a substituted or unsubstituted arylene group having 6 to 60 ring carbon atoms, or a substituted or unsubstituted fluorenylene group, R¹³ is a hydrogen atom, a substituted or unsubstituted aryl group having 6 to 60 ring carbon atoms, a substituted or unsubstituted alkyl group having 1 to 20 carbon atoms, or a substituted or unsubstituted alkoxy group having 1 to 20 carbon atoms, n is an integer of 0 to 5, when n is 2 or more, plural R¹³s may be the same or different, and adjacent R¹³s may bond to each other to form a carbocyclic aliphatic ring or a carbocyclic aromatic ring, and R¹⁴ is a hydrogen atom, a substituted or unsubstituted aryl group having 6 to 60 ring carbon atoms, a substituted or unsubstituted alkyl group having 1 to 20 carbon atoms, a substituted or unsubstituted alkoxy group having 1 to 20 carbon atoms, or -L³-Ar⁵—Ar⁴, provided that the benzimidazole derivative having a carbazole skeleton is excluded.

2. The organic electroluminescence derivative according to claim 1, wherein the aromatic amine derivative having a carbazole skeleton is a compound represented by the following formula (1):

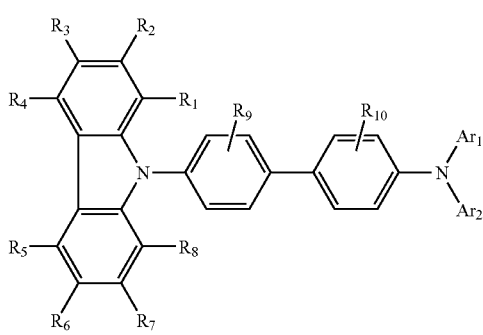

(1)

wherein Ar₁ and Ar₂ are independently an aromatic hydrocarbon ring group or an aromatic heterocyclic group which may be substituted, R₁ to R₁₀ are independently a hydrogen atom, a halogen atom, an alkyl group, an aralkyl group, an alkenyl group, a cyano group, an amino group, an acyl group, an alkoxycarbonyl group, a carboxy group, an alkoxy group, an aryloxy group, an alkylsulfonyl group, a hydroxy group, an amido group, an aromatic hydrocarbon ring group or an aromatic heterocyclic group which may be substituted, and adjacent groups of R₁ to R₁₀ may form a ring.

3. The organic electroluminescence derivative according to claim 1, wherein the aromatic amine derivative having a carbazole skeleton is a compound represented by the following formula (2):

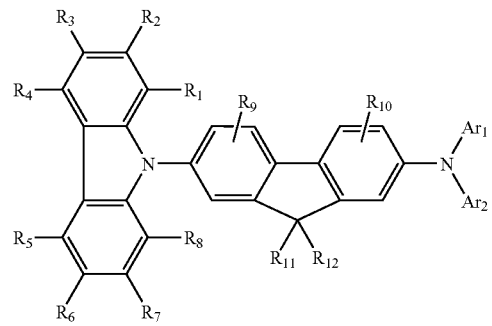

(2)

wherein Ar₁ and Ar₂ are independently an aromatic hydrocarbon ring group or an aromatic heterocyclic group which may be substituted, R₁ to R₁₂ are independently a hydrogen atom, a halogen atom, an alkyl group, an aralkyl group, an alkenyl group, a cyano group, an amino group, an acyl group, an alkoxycarbonyl group, a carboxyl group, an alkoxy group, an aryloxy group, alkylsulfonyl group, a hydroxy group, an amido group, an aromatic hydrocarbon ring group or an aromatic heterocyclic group which may be substituted, and adjacent groups of R₁ to R₁₂ may from a ring.

4. The organic electroluminescence device according to claim 1, wherein the carbazole skeleton of the aromatic amine derivative is a monocarbazolyl group.

5. The organic electroluminescence device according to claim 1, which emits blue light.

6. A display comprising the organic electroluminescence device according to claim 1.

7. The organic electroluminescence device according to claim 1, wherein
the Ar⁵ is an unsubstituted arylene group having 6 to 60 carbon atoms, and
the L³ is a single bond, an unsubstituted arylene group having 6 to 60 ring carbon atoms, or a substituted or unsubstituted fluorenylene group.

8. The organic electroluminescence device according to claim 1, wherein the aromatic amine derivative that has one carbazole skeleton is an aromatic monoamine derivative that has one carbazole skeleton.

9. The organic electroluminescence device according to claim 5, wherein the aromatic amine derivative that has one carbazole skeleton is an aromatic monoamine derivative that has one carbazole skeleton.

10. The organic electroluminescence device according to claim 7, wherein the aromatic amine derivative that has one carbazole skeleton is an aromatic monoamine derivative that has one carbazole skeleton.

* * * * *